(12) United States Patent
Watkins

(10) Patent No.: US 11,181,535 B2
(45) Date of Patent: Nov. 23, 2021

(54) ISOTOPICALLY-LABELED CHOLESTERYL ESTER INTERNAL STANDARD COMPOSITION AND KIT

(71) Applicant: Metabolon, Inc., Morrisville, NC (US)

(72) Inventor: Steven Watkins, Davis, CA (US)

(73) Assignee: Metabolon, Inc., Morrisville, NC (US)

( * ) Notice: Subject to any disclaimer, the term of this patent is extended or adjusted under 35 U.S.C. 154(b) by 0 days.

(21) Appl. No.: 15/251,579

(22) Filed: Aug. 30, 2016

(65) Prior Publication Data

US 2017/0192023 A1 Jul. 6, 2017

Related U.S. Application Data

(63) Continuation of application No. PCT/US2015/042904, filed on Jul. 30, 2015.

(60) Provisional application No. 62/031,099, filed on Jul. 30, 2014.

(51) Int. Cl.
*G01N 33/92* (2006.01)
*G01N 30/04* (2006.01)

(52) U.S. Cl.
CPC ....... *G01N 33/92* (2013.01); *G01N 2030/045* (2013.01); *G01N 2496/80* (2013.01); *G01N 2560/00* (2013.01); *Y10T 436/104165* (2015.01)

(58) Field of Classification Search
CPC .............. G01N 33/92; G01N 2030/045; G01N 2496/80; Y10T 436/104165
See application file for complete search history.

(56) References Cited

U.S. PATENT DOCUMENTS

| 4,224,031 A | 9/1980 | Mee et al. |
| 8,263,413 B1 * | 9/2012 | Hansen .............. G01N 33/6851 436/173 |
| 10,705,100 B1 * | 7/2020 | Hansen .................. G01N 33/92 |
| 2004/0063118 A1 | 4/2004 | Gross et al. |
| 2005/0048567 A1 * | 3/2005 | Winchester ............ G01N 33/58 435/7.1 |

(Continued)

FOREIGN PATENT DOCUMENTS

| CN | 101824064 A * | 9/2010 |
| EP | 2345897 A1 | 7/2011 |

(Continued)

OTHER PUBLICATIONS

Hsu, F.-F. et al. "Structural determination of sphingomyelin by tandem mass spectrometry with electrospray ionization," Journal of the American Society for Mass Spectrometry, vol. 11, Issue 5, May 2000, pp. 437-449 (Year: 2000).*

(Continued)

*Primary Examiner* — Christopher Adam Hixson
*Assistant Examiner* — Michelle Adams
(74) *Attorney, Agent, or Firm* — NK Patent Law

(57) ABSTRACT

Methods are provided for synthesizing mixtures of lipids that are representative of the structural diversity of the lipids present in samples of interest. The complex mixtures of lipids produced according to the methods of the present disclosure can be used as internal standards for detecting and quantifying the lipids in samples of interest. Kits including the internal standards and instructions for their use in the detection and quantification of lipids in samples of interest are also provided.

4 Claims, 22 Drawing Sheets

(56) References Cited

U.S. PATENT DOCUMENTS

| | | | |
|---|---|---|---|
| 2006/0084129 | A1 | 4/2006 | Watkins |
| 2007/0082399 | A1 | 4/2007 | Egorova-Zachernyuk |
| 2010/0159540 | A1 | 6/2010 | Rodriguez et al. |

FOREIGN PATENT DOCUMENTS

| | | | |
|---|---|---|---|
| JP | 2005512061 | A | 4/2005 |
| JP | 2013506142 | A | 2/2013 |
| WO | 03048784 | A2 | 6/2003 |
| WO | 2011038509 | A1 | 4/2011 |
| WO | 2014016586 | A1 | 1/2014 |

OTHER PUBLICATIONS

Koc, H. et al. "Quantitation of Choline and Its Metabolites in Tissues and Foods by Liquid Chromatography/Electrospray Ionization-Isotope Dilution Mass Spectrometry," Anal. Chem., 2002, 74 (18), pp. 4734-4740 (Year: 2002).*

Brown, R.J. et al. "Cholesterol efflux analyses using stable isotopes and mass spectrometry," Anal. Biochem. 433 (2013) 56-64. Available online Oct. 13, 2012. (Year: 2012).*

Weir, J.M. et al. "Plasma lipid profiling in a large population-based cohort," J Lipid Res. 2013; 54(10): 2898-2908. Published JLR Papers in Press, Jul. 18, 2013 (Year: 2013).*

Byrdwell, W.C. et al. "Quantitative Analysis of Triglycerides Using Atmospheric Pressure Chemical Ionization-Mass Spectrometry," Lipids, vol. 31, No. 9 (1996) 919-935 (Year: 1996).*

Bleijerveld, O.B. et al. "The CDP-ethanolamine Pathway and Phosphatidylserine Decarboxylation Generate Different Phosphatidylethanolamine Molecular Species," Journal of Biological Chemistry, vol. 282, Issue 39, 2007, pp. 28362-28372 (Year: 2007).*

1-Palmitoyl(D31)-2-Oleoyl-sn-Glycero-3-Phosphocholine (860399). Avanti Polar Lipids (Mar. 16, 2006) downloaded from <https://web.archive.org/web/20060316024103/http://www.avantilipids.com/ProductInfo.asp?ProdNum=860399> on Aug. 3, 2021 (Year: 2006).*

N-Palmitoyl(D31)-D-erythro-Sphingosylphosphorylcholine (Palmitoyl D31Sphingomyelin) (868584) Avanti Polar Lipids (Mar. 16, 2006) downloaded from <hhttps://web.archive.org/web/20060316001047/http://www.avantilipids.com/ProductInfo.asp?ProdNum=868584 on Aug. 3, 2021 (Year: 2006).*

ISA/US, International Search Report and Written Opinion for PCT Patent Application No. PCT/US15/42904, dated Dec. 23, 2015.

Murphy et al.: "Mass Spectrometric Analysis of Long-Chain Lipids", Mass Spectrom Rev. Jul. 2011, vol. 30, Issue 4.

Cyr D, et al. A GCIMS validated method for the nanomolar range determination of succinylacetone in amniotic fluid and plasma: an analytical tool for tyrosinemia type I. J Chromatogr B Analyt Techno Biomed Life Sci. Feb. 17, 2006;832(1):24-9.

Vogeser M. Liquid chromatography-tandem mass spectrometry-application in the clinical laboratory. Clin Chern Lab Med. Feb. 2003;41(2):117-26.

Khalil PN, et al. Validation and application of a high-performance liquid chromatographic-based assay for determination of the inosine 5'-monophosphate dehydrogenase activity in erythrocytes. J Chromatogr B Analyt Techno Biomed Life Sci. May 23, 2006.

Fouassier M, et al. Determination of serotonin release from platelets by HPLC and ELISA in the diagnosis of heparin-induced thrombocytopenia: comparison with reference method by [C)-serotonin release assay; J Thromb Haemost. May 2006;4(5): 1136-9.

Badiou S, et al. Determination of plasma amino acids by fluorescent derivatization and reversed-phase liquid chromatographic separation. Clin Lab. 2004;50(3-4): 153-8 (Abstract).

Brunelli T, et al. Comparison of three methods for total homocysteine plasma determination. Clin Lab. 200 I ;47(7-8):393-7 (Abstract).

Zinellu A, et al. Assay for the simultaneous determination of guanidinoacetic acid, creatinine and creatine in plasma and urine by capillary electrophoresis UV -detection. J Sep Sci. Mar. 2006;29(5):704-8.

Jabeen R, et al. Capillary electrophoresis and the clinical laboratory. Electrophoresis. May 23, 2006.

Gao P, et al. Rapid detection of *Staphylococcus aureus* by a combination of monoclonal antibody-coated latex and capillary electrophoresis. Electrophoresis. May 2006;27(9):1784-9.

Johannessen EA, et al. A suspended membrane nanocalorimeter for ultralow volume bioanalysis. IEEE Trans Nanobioscience. Mar. 2002;I(I):29-36.

Herrmann M, et al. Enzymatically-generated fluorescent detection in micro-channels with internal magnetic mixing for the development of parallel microfluidic ELISA; Lab Chip. Apr. 2006;6(4):555-60. Epub Mar. 3, 2006.

Yang S, et al. Blood plasma separation in microfluidic channels using flow rate control. ASAIO J. Sep.-Oct. 2005;51(5):585-90.

Dupuy AM, et al. Protein biochip systems for the clinical laboratory; Clin Chern Lab Med. 2005;43{12):1291-302.

Paterson S, et al. Validation of techniques to detect illicit heroin use in patients prescribed pharmaceutical heroin for the management of opioid dependence. Addiction. Dec. 2005; 1 00( 12): 1832-9.

Böttcher M, et al. Evaluation of buprenorphine CEDIA assay versus GC-MS and ELISA using urine samples from patients in substitution treatment. J Anal Toxicol. Nov.-Dec. 2005;29(8):769-76.

Julak J. Chromatographic analysis in bacteriologic diagnostics of blood cultures, exudates, and bronchoalveolar lavages. Prague Med Rep. 2005; 1 06(2): 175-94.

Boettcher M, et al. Precision and comparability of Abuscreen OnLine assays for drugs of abuse screening in urine on Hitachi 917 with other immunochemical tests and with GC/MS. Clin Lab 2000;46(1-2):49-52 (Abstract).

Westermann J, et al. Simple, rapid and sensitive determination of epinephrine and norepinephrine in urine and plasma by non-competitive enzyme immunoassay, compared with HPLC method. Clin Lab. 2002;48(1-2):61-71 (Abstract).

Aoyagi K, et al. Performance of a conventional enzyme immunoassay for hepatitis C virus core antigen in the early phases of hepatitis C infection. Clin Lab. 200 I ;47(3-4): 119-27 (Abstract).

Hubl W, et al. A multi-center quality control study of different CA 15-3 immunoassays. Clin Lab. 2005;51(11-12):641-5 (Abstract).

Haller CA, et al. Comparison of an automated and point-of-care immunoassay to GC-MS for urine oxycodone testing in the clinical laboratory. J Anal Toxicol. Mar. 2006;30(2): 106-11.

Bayer M, et al. Evaluation of a new enzyme-linked immunosorbent assay for the determination of neopterin. Clin Lab. 2005 ;51 (9-1 0):495-504 (Abstract).

Groche D, et al. Standardization of two immunological HbA 1 c routine assays according to the new IFCC reference method. Clin Lab. 2003;49( 11-12):657-61 (Abstract).

Ivan D, et al.; German KIMS Board. Applicability of recently established reference values for serum insulin-like growth factor I: A comparison of two assays—an (automated) chemiluminescence immunoassay and an enzyme-linked mmunosorbent assay. Clin Lab. 2005;51(7-8):381-7 (Abstract).

Kramer KA, et al. Automated spectrophotometric analysis of mitochondrial respiratory chain complex enzyme activities in cultured skin fibroblasts. Clin Chern. Nov. 2005;51(11):2110-6.

Wolf PL. History of diagnostic enzymology: A review of significant investigations. Clin Chim Acta. Mar. 24, 2006.

Mutch DM, et al. An integrative metabolism approach identifies stearoyi-CoA desaturase as a target for an arachidonate-enriched diet. FASEB J. Apr. 2005;19(6):599-601.

Stone SJ, et al. Lipopenia and skin barrier abnormalities in DGAT2-deficient mice. J Bioi Chern. Mar. 19, 2004;279(12):11767-76.

Watkins SM, et al. Phosphatidylethanolamine-N-methyltransferase activity and dietary choline regulate liver-plasma lipid flux and essential fatty acid metabolism in mice.J Nutr. Nov. 2003; 133(11 ):3386-91.

Watkins SM, et al. Lipid metabolome-wide effects of the PPARgamma agonist rosiglitazone. Lipid Res. Nov. 2002;43(11):1809-17.

(56) References Cited

OTHER PUBLICATIONS

EOP, Supplemental European Search Report for European Patent Application No. 15 82 7995 dated Jan. 3, 2018.

Moore, Jeff D., et al., Quantitation and Standardization of Lipid Internal Standards for Mass Spectrosopy, Methods in Enzymology, Academic Press, US, Jan. 1, 2007, pp. 351-367, vol. 432, XP009122880, ISSN: 0076-6879.

Stephens, Daren, Fatty Acid Mass Spectrometry Protocol, Oct. 11, 2017, XP55426096, pp. 1-6.

Ekroos, Kim et al., "Quantitative Profiling of Phospholipids by Multiple Precursor Ion Scanning on a Hybrid Quadrupole Time-of-Flight Mass Spectrometer", Analytical Chemistry, Mar. 1, 2002, pp. 941-949, vol. 74, No. 5.

Khalil, Maroun Bou et al., "Lipidomics Era: Accomplishments and Challenges", Mass Spectrometry Reviews, 2010, pp. 877-929, vol. 29.

IP Australia, Examination Report for Australian Patent Application No. 2015296304, dated Oct. 10, 2018.

EPO, Examination Report for European Patent Application No. 15 827 995.0, dated Nov. 22, 2018.

Paddy, Michael R., "Simultaneous Observation of Order and Dynamics at Several Defined Positions in Single Acyl Chain Using 2H NMR of Single Acyl Chain Perdeuterated Phosphatidylcholines", Biochemistry, Oct. 1, 1985, pp. 5988-5995, vol. 24, No. 21.

IP Australia; Examination Report for Australian Patent Application No. 2015296304 dated May 15, 2019, 5 pages.

JPO; Office Action for Japanese Patent Application No. 2017-505546 dated Aug. 6, 2019, 8 pages.

Tulloch, A.P., "Synthesis, Analysis and Application of Specifically Deuterated Lipids", Prog. Lipid Red., vol. 22, 1983, pp. 235-256.

Lam, Sin Man, et al., "Extensive characterization of human tear fluid collected using different techniques unravels the presence of novel lipid amphiphiles", Journal of Lipid Research, vol. 55, 2014, pp. 289-298.

EPO; Exam Report for European Patent Application No. 15827995.0 dated Dec. 5, 2019, 11 pages.

EPO; Office Action for European Patent Application No. 15827995.0 dated Oct. 14, 2020, 10 pages.

Harkewicz, Richard, et al., "Applications of Mass Spectrometry to Lipids and Membranes", Annual Review of Biochemistry, vol. 80, No. 7, Jul. 2011, 29 pages.

JPO; Office Action for Japanese Patent Application No. 2017-505546 dated May 26, 2020, 8 pages.

CNIPA; Office Action for Chinese Patent Application No. 201580040519.5 dated Jun. 17, 2020, 9 pages.

CPO; Office Action for Canadian Patent Application No. 2,955,204 dated Apr. 27, 2021, 10 pages.

CNIPA; Office Action for Chinese Patent Application No. 201580040519.5 dated May 11, 2021, 6 pages.

CNIPA; Office Action for Chinese Patent Application No. 201580040519.5 dated Dec. 2, 2020, 19 pages.

\* cited by examiner

PC(16:0-d9/R)

PC(16:0-d9/18:1n9)

PE(18:0-d9/R)

PE(18:0-d9/18:1n9)

TG(16:0-d9/18:1n9/R)

TG(16:0-d9/18:1n9/16:0)

DG(16:0-d9/R)

DG(16:0-d9/16:0)

ISOTOPICALLY-LABELED CHOLESTERYL ESTER INTERNAL STANDARD COMPOSITION AND KIT

CROSS REFERENCE TO RELATED APPLICATIONS

This application is a continuation of PCT patent application number PCT/US15/42904 filed Jul. 30, 2015, which claims the benefit of U.S. provisional patent application No. 62/031,099 filed Jul. 30, 2014, the disclosure of which is hereby incorporated by reference in its entirety.

TECHNICAL FIELD

The presently disclosed subject matter relates to methods, compositions, and kits for synthesizing and using mixtures of complex lipids as internal standards for analysis of biological samples and other samples containing mixtures of complex lipids.

BACKGROUND

Using an internal standard to calibrate the concentration of a target compound in a sample is a well-accepted method of quantification. In short, a compound is added that is not present in the sample to be tested that satisfies two criteria: (1) that the internal standard act similarly to the target compound at all stages of sample preparation (e.g. extraction, chromatography, etc) and that (2) it is distinguishable from the target compound by the detection method of choice. Thus, if one knows the concentration of the internal standard added to the sample, and the relative response of the detector (e.g. peak area) to both the target compound and the internal standard, one can calculate the amount of target compound that must have been in the original sample.

Lipids in biological samples are problematic targets for quantification by internal standard because they have a diverse array of chemical properties, even within a given lipid class. The lipids also have combinatorial complexity, for example, several of many potential fatty acids are acylated onto one of a dozen or so backbones. Thus a small number of internal standards cannot meet the first of the above two criteria. Generally, analysts use few internal standard compounds, and most often choose only a single compound to represent a broad class of lipid (e.g., phospholipids, neutral lipids) to use as an internal standard. The choice of the standard for the broad class has historically related more to the absence of the compound in biological samples and the ease of synthesis of the synthetic compound than to the similarity of the standard to the chemical properties of the target analytes. Most lipid internal standards are constructed from a single odd-chain or short-chain fatty acid (e.g. PC12:0/12:0 or TAG17:0/17:0/17:0). Most mixtures of internal standards use a single internal standard per broad lipid class. However, current approaches for developing internal standards are limited because: 1) short chain fatty acids or completely saturated fatty acid internal standards do not act like the target compounds in the assay and 2) it is difficult to represent the combinatorial complexity of lipids using simple internal standard strategies.

There is a need for a structurally diverse set of standards with appropriate chemical properties for each lipid class for use as internal standards. Such a set of internal standards provides broad chemical diversity and thus better coverage for analysis.

SUMMARY

Described herein are methods, kits, and compositions relating to internal standards for use in mass spectrometry analysis. Complex lipids are classes of lipids with a diverse array of fatty acids attached to them. Methods of synthesizing and using compositions and kits that include mixtures of lipid molecules as internal standards with a sufficiently diverse composition to effectively represent the fatty acids of the complex lipid class(es) in samples of interest are provided herein. The internal standards are synthesized to contain the characteristics described herein. The synthesized internal standards may then be packaged in a kit and used for lipid analysis. The lipid internal standards described herein may be used in any application including, for example, mass spectrometry.

In one embodiment of the present disclosure, a method is provided for synthesizing one or more mixtures of lipid molecules representative of the composition of lipid molecular species present in one or more corresponding lipid classes in a sample of interest, the method comprising: attaching an isotopically-labeled fatty acid at a first position on a lipid backbone through an acylation reaction for a lipid class having at least two acyl groups; and attaching a mixture of at least two different fatty acids to the lipid backbone at a separate position through an acylation reaction, wherein the mixture of fatty acids is representative of the fatty acids that occur in the corresponding lipid class in the sample of interest, and wherein each of the fatty acids in the mixture is present at a ratio representative of the ratio of occurrence of the fatty acid in the lipid molecular species present in the corresponding lipid class in the sample of interest.

In one embodiment of the present disclosure, a method is provided for synthesizing one or more mixture of lipid molecules representative of the composition of lipid molecular species present in one or more corresponding lipid classes in a sample of interest, the method comprising: attaching a mixture of at least two different fatty acids to an isotopically-labeled lipid backbone at a single position through an acylation reaction for a lipid class having at least one acyl group, wherein the mixture of fatty acids is representative of the fatty acids that occur in the corresponding lipid class in the sample of interest, and wherein each of the fatty acids in the mixture is present at a ratio representative of the ratio of occurrence of the fatty acid in the lipid molecular species present in the corresponding lipid class in the sample of interest.

In one embodiment of the present disclosure, a composition is provided for use as an internal standard comprising one or more mixtures of lipid molecules representative of the composition of lipid molecular species present in one or more corresponding lipid classes in a sample of interest, each mixture of lipid molecules comprising: a lipid backbone having an isotopically-labeled fatty acid at a first position on the lipid backbone, wherein the lipid backbone is for a lipid class having at least two acyl groups; and a mixture of at least two different fatty acids present at a separate position on the lipid backbone, wherein the mixture of fatty acids is representative of the fatty acids that occur in the lipid class in the sample of interest, and wherein each of the fatty acids in the mixture is present at a ratio representative of the ratio of occurrence of the fatty acid in the lipid molecular species present in the corresponding lipid class in the sample of interest.

In one embodiment of the present disclosure, a composition is provided for use as an internal standard comprising one or more mixtures of lipid molecules representative of the composition of lipid molecular species present in one or more corresponding lipid classes in a sample of interest, each mixture of lipid molecules comprising: a lipid backbone having one or more isotopic labels, wherein the lipid backbone is for a lipid class having at least one acyl group; and a mixture of at least two different fatty acids present at a single position on the lipid backbone, wherein the mixture of fatty acids is representative of the fatty acids that occur in the lipid class in the sample of interest, and wherein each of the fatty acids in the mixture is present at a ratio representative of the ratio of occurrence of the fatty acids in the lipid molecular species present in the corresponding lipid class in the sample of interest.

In one embodiment of the present disclosure, a kit is provided comprising: i) one or more mixtures of lipid molecules for use as an internal standard, wherein each mixture of lipid molecules is representative of the composition of lipid molecular species present in each of one or more corresponding lipid classes in a sample of interest, each mixture of lipid molecules comprising: a lipid backbone having an isotopically-labeled fatty acid at a first position on the lipid backbone and a mixture of at least two different fatty acids present at a separate position on the lipid backbone, wherein the lipid backbone is for a lipid class having at least two acyl groups, or a lipid backbone having one or more isotopic labels and a mixture of at least two different fatty acids present at a single position on the lipid backbone, wherein the lipid backbone is for a lipid class having at least one acyl group, wherein the mixture of fatty acids is representative of the fatty acids that occur in the corresponding lipid class in the sample of interest, and wherein each of the fatty acids in the mixture is present at a ratio representative of the ratio of occurrence of the fatty acids in the lipid molecular species present in the lipid class in the sample of interest; and ii) instructions for using the one or more mixtures of lipid molecules as the internal standard for one of detecting and quantifying the lipid molecular species present in the corresponding lipid class in the sample of interest.

In one embodiment of the present disclosure, a method is provided for one of detecting and quantifying lipid molecules present in a sample of interest, comprising: adding to a sample of interest a known amount of a composition having one or more mixtures of lipid molecules representative of the composition of lipid molecular species present in one or more corresponding lipid classes in the sample of interest, wherein each mixture of lipid molecules comprises i) a lipid backbone having an isotopically-labeled fatty acid at a first position on the lipid backbone, wherein the lipid backbone is for a lipid class having at least two acyl groups; and ii) a mixture of at least two different fatty acids present at a separate position on the lipid backbone, wherein the mixture of fatty acids is representative of the fatty acids that occur in the corresponding lipid class in the sample of interest, and wherein each of the fatty acids in the mixture is present at a ratio representative of the ratio of occurrence of the fatty acid in the lipid molecular species present in the corresponding lipid class in the sample of interest; and one of detecting and quantifying the lipid molecular species present in the corresponding lipid class in the sample of interest by using the representative mixture of lipid molecules as an internal standard.

In one embodiment of the present disclosure, a method is provided for one of detecting and quantifying lipid molecules present in a sample of interest, comprising: adding to a sample of interest a known amount of a composition having one or more mixtures of lipid molecules representative of the composition of lipid molecular species present in one or more corresponding lipid classes in the sample of interest, wherein each mixture of lipid molecules comprises i) a lipid backbone having one or more isotopic labels, wherein the lipid backbone is for a lipid class having at least one acyl group; and ii) a mixture of at least two different fatty acids present at a single position on the lipid backbone, wherein the mixture of fatty acids is representative of the fatty acids that occur in the corresponding lipid class in the sample of interest, and wherein each of the fatty acids in the mixture is present at a ratio representative of the ratio of occurrence of the fatty acids in the lipid molecular species present in the corresponding lipid class in the sample of interest; and one of detecting and quantifying the lipid molecular species present in the corresponding lipid class in the sample of interest by using the representative mixture of lipid molecules as an internal standard.

In one embodiment of the present disclosure, a method is provided for synthesizing one or more mixtures of lipid molecules for use as an internal standard representative of the composition of lipid molecular species present in one or more corresponding lipid classes in a sample of interest, the method comprising one or more of: attaching a mixture of at least two different isotopically-labeled fatty acids to a lipid backbone at a single position through an acylation reaction for a lipid class having at least one acyl group; attaching a mixture of at least two different fatty acids to an isotopically-labeled lipid backbone at a single position through an acylation reaction for a lipid class having at least one acyl group; or attaching a single isotopically-labeled fatty acid to a lipid backbone at a first position through an acylation reaction for a lipid class having at least two fatty acids and attaching a mixture of at least two different fatty acids to a separate position on the lipid backbone through an acylation reaction, wherein the mixture of the at least two different fatty acids is representative of the fatty acids that occur in the corresponding lipid class in the sample of interest, and wherein each of the fatty acids in the mixture is present at a ratio representative of the ratio of occurrence of the fatty acid in the lipid molecular species present in the corresponding lipid class in the sample of interest.

In one embodiment of the present disclosure, a composition is provided for use as an internal standard comprising one or more mixtures of lipid molecules representative of the composition of lipid molecular species present in one or more corresponding lipid classes in a sample of interest, each mixture of lipid molecules comprising one or more of: a lipid backbone having a mixture of at least two different isotopically-labeled fatty acids at a single position on the lipid backbone, wherein the lipid backbone is for a lipid class having at least one acyl group; an isotopically-labeled lipid backbone having a mixture of at least two different fatty acids at a single position on the lipid backbone, wherein the lipid backbone is for a lipid class having at least one acyl group; or a lipid backbone having a single isotopically-labeled fatty acid at a first position on the lipid backbone and having a mixture of at least two different fatty acids at a separate position on the lipid backbone, wherein the lipid backbone is for a lipid class having at least two fatty acids, wherein the mixture of the at least two fatty acids is representative of the fatty acids that occur in the corresponding lipid class in the sample of interest, and wherein each of the fatty acids in the mixture is present at a ratio representative of the ratio of occurrence of the fatty acids in the lipid molecular species present in the corresponding lipid class in the sample of interest.

In one embodiment of the present disclosure, a kit is provided comprising: i) one or more mixtures of lipid molecules for use as an internal standard, wherein each of the one or more mixtures of lipid molecules is representative of the composition of lipid molecular species present in one or more corresponding lipid classes in a sample of interest, each mixture of lipid molecules comprising one or more of: a lipid backbone having a mixture of at least two different isotopically-labeled fatty acids at a single position on the lipid backbone, wherein the lipid backbone is for a lipid class having at least one acyl group; an isotopically-labeled lipid backbone having a mixture of at least two different fatty acids at a single position on the lipid backbone, wherein the lipid backbone is for a lipid class having at least one acyl group; or a lipid backbone having a single isotopically-labeled fatty acid at a first position on the lipid backbone and having a mixture of at least two different fatty acids at a separate position on the lipid backbone, wherein the lipid backbone is for a lipid class having at least two acyl groups, wherein the mixture of at least two different fatty acids is representative of the fatty acids that occur in the lipid class in the sample of interest, and wherein each of the fatty acids in the mixture is present at a ratio representative of the ratio of occurrence of the fatty acids in the lipid molecular species present in the corresponding lipid class in the sample of interest; and ii) instructions for using the one or more mixtures of lipid molecules as the internal standard for one of detecting and quantifying the lipid molecular species present in the corresponding lipid class in the sample of interest.

In one embodiment of the present disclosure, a method is provided for one of detecting and quantifying lipid molecules present in a sample of interest, the method comprising: i) adding to a sample of interest a known amount of a composition having one or more mixtures of lipid molecules representative of the composition of lipid molecular species present in one or more corresponding lipid classes in the sample of interest, the composition comprising one or more of: a) a lipid backbone having a mixture of at least two different isotopically-labeled fatty acids at a single position on the lipid backbone, wherein the lipid backbone is for a lipid class having at least one acyl group; b) an isotopically-labeled lipid backbone having a mixture of at least two different fatty acids at a single position on the lipid backbone, wherein the lipid backbone is for a lipid class having at least one acyl group; or c) a lipid backbone having a single isotopically-labeled fatty acid at a first position on the lipid backbone and having a mixture of at least two different fatty acids at a separate position on the lipid backbone, wherein the lipid backbone is for a lipid class having at least two fatty acids, wherein the mixture of the at least two fatty acids is representative of the fatty acids that occur in the lipid class in the sample of interest, and wherein each of the fatty acids in the mixture is present at a ratio representative of the ratio of occurrence of the fatty acids in the lipid molecular species present in the lipid class in the sample of interest; and ii) one of detecting and quantifying the lipid molecular species present in each of the one or more corresponding lipid classes in the sample of interest by using the composition having the one or more representative mixtures of lipid molecules as an internal standard.

DETAILED DESCRIPTION

Figure 1:
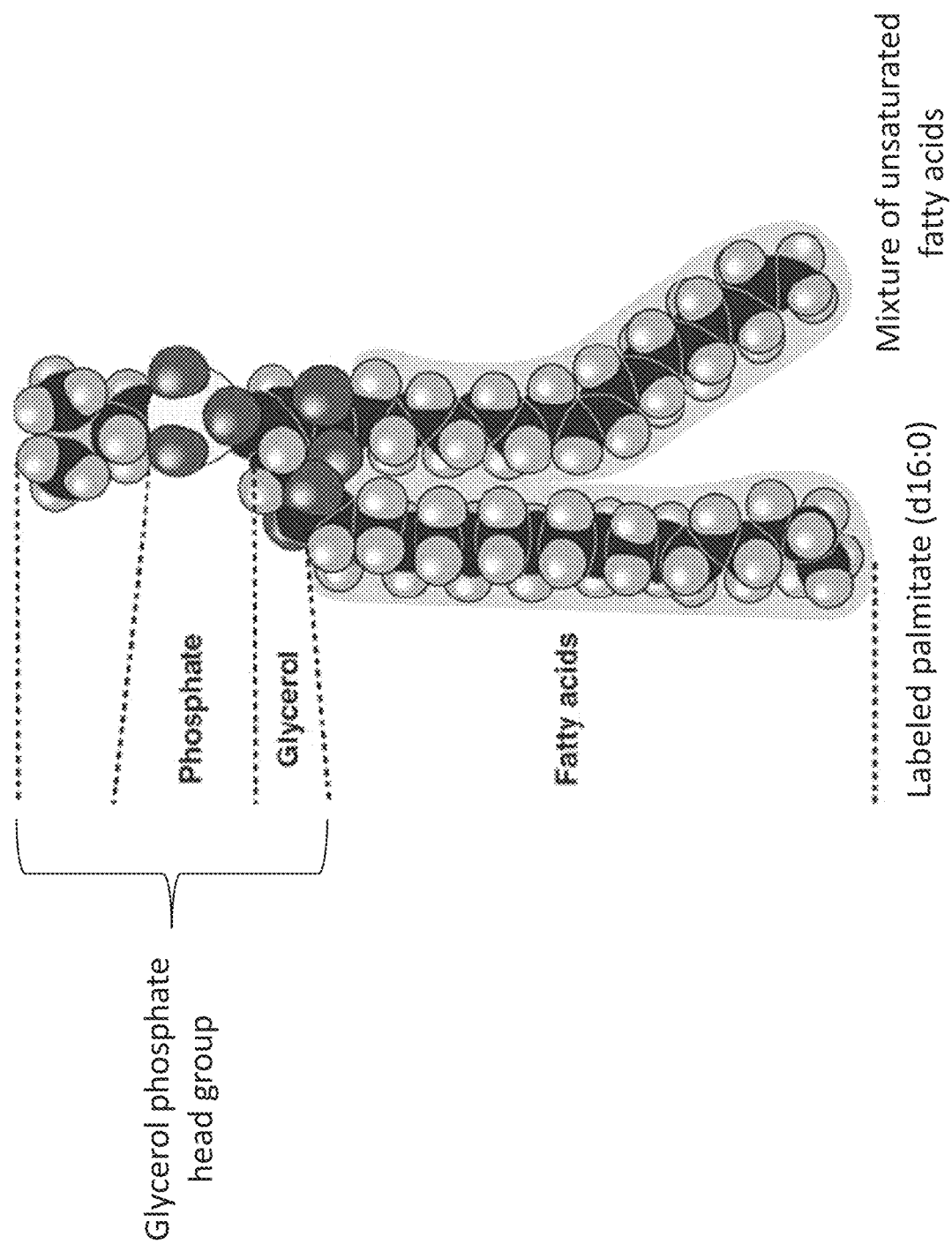
FIG. 1 is a schematic of a phospholipid showing a general strategy for producing phospholipid internal standards according to one or more embodiments of the present disclosure.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Lipids are problematic targets for quantification by internal standards because they have a diverse array of chemical properties, even within a given lipid class. The lipids also have combinatorial complexity, for example, several of many potential fatty acids are acylated onto one of a dozen or so backbones. Thus a small number of internal standards cannot meet the first of the above two criteria. What is needed is a way to make a set of internal standards that (1) represents the chemical diversity of complex lipids and (2) creates a mixture of these standards in a relative abundance, representing the expected composition of lipids in a sample, which makes the compounds useful as internal standards. The presently disclosed subject matter provides methods and compositions for internal standards that are representative of the chemical diversity of complex lipids.

Described herein are reagents and kits for a structurally diverse set of lipid standards with appropriate chemical properties and/or analytical properties for each lipid class. With respect to the nomenclature for fatty acid "lipid metabolites" (or otherwise referred to herein as "lipid molecules") used herein, fatty acids labeled with a prefix "CE" (cholesteryl esters), "DG" (diacylglycerols or diglycerides), "FA" (free fatty acids), "PC" (phosphatidylcholines), "PE" (phosphatidylethanolamines), "LPC" (lysophosphatidylcholines), "LPE" (lysophosphatidylethanolamines), "O-PC" (1-ether linked phosphatidylcholines), "P-PE" (1-vinyl ether linked phosphatidylethanolamines), "SM" (sphingomyelins), "TG" (triacylglycerols or triglycerides), or "CER" (ceramides) refer to the indicated fatty acids present within cholesteryl esters, diacylglycerols (diglycerides), free fatty acids, phosphatidylcholines, phosphatidylethanolamines, lysophosphatidylcholines, lysophosphatidylethanolamines, 1-ether linked phosphatidylcholines, 1-vinyl ether linked phosphatidylethanolamines (plasmalogens), sphingomyelins, triacylglycerols (triglycerides), and ceramides, respectively, in a sample. In some embodiments, the indicated fatty acid components are quantified as a proportion of total fatty acids within the lipid class indicated by the prefix. References to fatty acids without a prefix or other indication of a particular lipid class generally indicate fatty acids present within total lipids in a sample. The term "LC" following a prefix "CE" (cholesteryl ester), "DG" (diacylglycerol), "FA" (free fatty acid), "PC" (phosphatidylcholine), "PE" (phosphatidylethanolamine), "LPC" (lysophosphatidylcholine), "LPE" (lysophosphatidylethanolamine), "O-PC" (1-ether linked phosphatidylcholine), "P-PE" (1-vinyl ether linked phosphatidylethanolamine), "SM" (sphingomyelin), "TG" (triacylglycerol), or "CER" (ceramide) refers to the amount of the total lipid class indicated by the prefix in the sample (e.g., the concentration of lipids of that class expressed as nMoles per gram of serum or plasma). For example, with respect to a measurement taken from plasma or serum, in some embodiments, the abbreviation "PC 18:2n6" indicates the percentage of plasma or serum phosphatidylcholine comprised of linoleic acid (18:2n6), and the term "TGLC" indicates the absolute amount (e.g., in nMoles per gram) of triglyceride present in plasma or serum. "MUFA", "PUFA", and "SFA" refer to monounsaturated fatty acid, polyunsaturated fatty acid, and saturated fatty acid, respectively.

As used herein, "lipid backbone" refers to the portion of the lipid molecule that excludes the fatty acid groups or acyl groups. As used herein, the terms "fatty acids" and "acyl groups" are used interchangeably. As used herein, "lipid molecular species" or "molecular species" refers to a lipid molecule comprised of a specific fatty acid or acyl group attached to a specific lipid backbone (e.g., PC 18:2n6, CE 16:1n6, etc.).

As used herein, "isotopically labeled" refers to an internal standard or any portion of an internal standard marked for determination using any suitable moiety (e.g., deuterium ($^2$H, $^{13}$C, $^{15}$N). Any atom or any number of atoms of the internal standard may be labeled with the isotope. For example, the isotope may be deuterium, and the internal standard may contain 9 deuterium atoms. In another example, the isotope may be deuterium and the internal standard may contain 11, 13, 15, 17, 19, 21, 23, 25, 27, 29, or 31 deuterium atoms.

One use of the methods described herein is for calibrating or aiding in calibrating mass spectrometry instruments or multiple mass spectrometry instruments run in tandem (i.e., a "platform"). In one example, two types of calibration are required: one for lipid class concentrations and one for fatty acid composition of the class. The results of the platform calibration may be computationally calibrated using either the control samples or comparison to a quantitative database of results.

The methods described herein to generate an internal standard mixture may be applied to any lipid or class of lipid The term "lipid class" as used herein is meant to refer to a class of lipid including, for example, triacylglycerols, diacylglycerols, cholesteryl esters, free fatty acids, phosphatidylcholine, o-phosphatidylcholine, phosphatidylethanolamine, p-phosphatidylethanolamine, lysophosphatidylcholine, lysophosphatidylethanolamine, sphingomyelin, cardiolipin, phosphatidylserine, lysophosphatidylserine, phosphatidylinositol, lysophosphatidylinositol, phosphatidylglycerol, lysophosphatidylglycerol, phosphatidic acid, lysophosphatidic acid, cytidine diphosphate (CDP)-diacylglycerol, lyso CDP-diacylglycerol, ceramide, lactosylceramide, glucosylceramide, phytoceramide, 6-hydroxyceramide, cerebroside, ganglioside, wax esters, wax diesters, and 1-monoacylglycerol. The triacylglycerols, diacylglycerols, cholesteryl esters, free fatty acids are broadly as neutral lipids. The phosphatidylcholine, o-phosphatidylcholine, phosphatidylethanolamine, p-phosphatidylethanolamine, lysophosphatidylcholine, lysophosphatidylethanolamine, sphingomyelin, cardiolipin, phosphatidylserine, lysophosphatidylserine, phosphatidylinositol, lysophosphatidylinositol, phosphatidylglycerol, lysophosphatidylglycerol, phosphatidic acid, lysophosphatidic acid, CDP-diacylglycerol, lyso CDP-diacylglycerol are broadly as phospholipids.

The internal standard mixture may include a phospholipid wherein each phospholipid head group (e.g., PC, PE, SM) contains a) an isotopically-labeled fatty acid wherein the isotopically-labeled fatty acid is at the sn-1 or sn-2 position; and b) an acylated mixture of fatty acids, wherein the acylated mixture of fatty acids is at a separate position (i.e., the position not occupied by the isotopically-labeled fatty acid), and wherein the acylated mixture of fatty acids approximates the concentration of fatty acids in the target complex lipid.

In one example, the isotopically-labeled fatty acid is a saturated fatty acid, and the acylated mixture of fatty acids is a pre-defined mixture of unsaturated and polyunsaturated fatty acids. In one example, the isotopically-labeled saturated fatty acid is palmitate (16:0) at the sn-1 position, and the acylated mixture of unsaturated and polyunsaturated fatty acids is a pre-defined mixture at the sn-2 position. In one example, the acylated mixture is comprised of unsaturated fatty acids. In one example, the phospholipid is lysophosphatidylcholine, and the phospholipid head group contains isotopically-labeled palmitate (16:0) at the sn-1 position. In another example, the phospholipid is lysophosphatidylethanolamine, and the phospholipid head group contains isotopically-labeled stearate (18:0) at the sn-1 position. The method for producing the mixture of fatty acids is as follows: 1) determine the concentration of fatty acids in the given sample type, the concentration may be already known or may be determined by fatty acid composition analysis; 2) select a fatty acid from one or more representative degrees of unsaturation (e.g., monoene, diene, triene, tetraene, pentaene, hexaene), wherein the most abundant fatty acid in the lipid class is selected; 3) based upon the concentration of the fatty acid in the sample type, assign each fatty acid in the mixture as "high" or "low" abundance; 4) assign a percentage value of the mixture corresponding to the high and low abundance (e.g., a fatty acid with "high" abundance would comprise 20% of the mixture and a fatty acid with "low" abundance would comprise 5%); and 5) for the remaining percentage of the mixture, determine the most abundant fatty acids among unsaturated fatty acids and assign a high or low abundance as described above to complete the mixture.

The internal standard mixture may include a phospholipid wherein the head group of each phospholipid class (e.g., PC, PE, SM) contains a) an unlabeled fatty acid, wherein the unlabeled fatty acid is at the sn-1 or sn-2 position; and b) a MUFA or PUFA, wherein the MUFA or PUFA is at the position not occupied by the unlabeled fatty acid. In one example, the head group contains a) an unlabeled odd chain saturated fatty acid, wherein the unlabeled odd chain saturated fatty acid is at the sn-1 position; and b) an odd chain MUFA or PUFA, wherein the odd chain MUFA or PUFA is at the sn-2 position.

The internal standard mixture may include neutral lipids wherein the neutral lipids include mixtures of isotopically-labeled MUFA or odd-chain MUFA (e.g., 17:1, 19:1, etc.).

In some embodiments, a quantitative fatty acid analysis may determine the exact composition of the internal standard mixture. In one example for phospholipids, the sn-1 position of each phospholipid head group is completely labeled with a single deuterated saturated fatty acid (e.g. d16:0), therefore the remainder of the fatty acids are present in the sn-2 position. The equation is as follows: 1=A/X+B/X+C/X, etc., where X is the percent of the single deuterated saturated fatty acid in the mixture; where A, B, C, etc. are fatty acids in the mixture; and where the percent of the fatty acids A, B, C, etc. in the internal standard mixture is known relative to X. Further, A/X=amount of the mixture comprised of A. For example, if the composition of the internal standard mixture for PC as determined by FAME analysis is: d16:0-50%, 18:1n9-10%, 18:2n6-20%, and 20:4n6-20%, then 1=(0.1/0.5)+(0.2/0.5)+(0.2/0.5) and 0.1/0.5=0.2; 0.2/.5=0.4; and 0.2/0.5=0.4, then the mixture is comprised of 20% PCd16:0/18:1n9, 40% PCd16:0/18:2n6, and 40% PCd16:0/20:4n6.

A free fatty acid is one type of neutral lipid that may comprise the internal standard mixture. The free fatty acid may be any free fatty acid including, for example, a single odd-chain fatty acid (e.g. 17:1, 17:2, 17:0) and/or an isotopically-labeled fatty acid (e.g. 16:0, 16:1, 17:0). The free fatty acid may be a MUFA or the fatty acid may be a PUFA.

A cholesteryl ester is one type of neutral lipid that may comprise the internal standard mixture. The cholesteryl ester may be any cholesteryl ester including, for example a cholesteryl ester comprised of a labeled cholesterol molecule, esterified to a mixture of fatty acids representing the expected composition of cholesteryl esters in the sample (see the Table 1).

Diacylglycerols are one type of neutral lipid that may comprise the internal standard mixture. The diacylglycerol may be any diacylglycerol including, for example, a single odd-chain fatty acid or an isotopically-labeled fatty acid. The fatty acid chains of the diacylglycerol may contain a) an isotopically-labeled fatty acid wherein the isotopically labeled fatty acid is at the sn-1 or sn-2 position (a first position); and b) an acylated mixture of fatty acids, wherein the acylated mixture of fatty acids is at a separate position (i.e., the position not occupied by the isotopically-labeled fatty acid). In one example, the isotopically-labeled fatty acid is a saturated fatty acid. In one example, the isotopically-labeled fatty acid is palmitate (16:0) at the first position, and the acylated mixture of fatty acids is at the separate position and may comprise 16:0, 18:0, 18:1n9, 18:2n6, 18:3n3, 20:4n6, 20:5n3, and 22:6n3. In one example, the isotopically-labeled fatty acid is palmitate (16:0) at the first position and the acylated mixture of fatty acids at the separate position is a mixture of unsaturated and polyunsaturated fatty acids. In another example, the fatty acid chains of the diacylglycerol in the internal standard mixture may contain a) an unlabeled odd chain saturated fatty acid, wherein the unlabeled odd chain saturated fatty acid is at the first position; and b) an odd chain MUFA or PUFA, wherein the odd chain MUFA or PUFA is at the separate position. The diacylglycerol in the internal standard mixture may use multiple homogenous internal standards (e.g. DG17:0/17:0 and DG17:1/17:1).

A triacylglycerol is one type of neutral lipid that may comprise the internal standard mixture. The triacylglycerol may be any triacylglycerol including, for example, a mixture of an odd-chain fatty acid and/or an isotopically-labeled fatty acid to make a mixed standard. The fatty acid chains of the triacylglycerol may contain a) a labeled fatty acid at one position; b) an unlabeled fatty acid at a separate position; and c) an acylated mixture of fatty acids at another separate position. In one example, the labeled fatty acid may be a saturated fatty acid, and the unlabeled fatty acid may be an unsaturated fatty acid. In one example, the label may be a deuterium label. In one example, the fatty acid chains of the triacylglycerol in the internal standard mixture contain a) isotopically-labeled palmitate (16:0) at one position (e.g., the sn-1 position); b) oleate (18:1n9) at a separate, or second, position (e.g., the sn-2 position); and c) an acylated mixture of fatty acids at another separate, or third, position (e.g., the sn-3 position). The acylated mixture of fatty acids at the third (e.g., sn-3) position may comprise, for example, 16:0, 18:0, 18:1n9, 18:2n6, 18:3n3, 20:3n6, 20:4n6 and 22:6n3.

The internal standard mixture may comprise: a) phosphatidylcholine lipid class with isotopically-labeled palmitate (16:0) in the sn-1 position and a mixture of MUFA and PUFA in the sn-2 position; b) phosphatidylethanolamine lipid class with isotopically-labeled palmitate (16:0) or stearate (18:0) in the sn-1 position, and a mixture of MUFA and PUFA in the sn-2 position; c) lysophosphatidylcholine lipid class with isotopically-labeled palmitate (16:0) in the sn-1 position; d) lysophosphatidylethanolamine lipid class with isotopically-labeled palmitate (16:0) or stearate (18:0) in the sn-1 position; e) sphingomyelin lipid class with an isotopically-labeled sphingoid backbone and a mixture of fatty acids in the sn-2 position; f) triacylglycerol lipid class with isotopically-labeled palmitate in the sn-1 position, unlabeled oleate (or other fatty acid) in the sn-2 position, and a mixture of fatty acids in the sn-3 position; g) cholesteryl ester lipid class with isotopically-labeled cholesterol headgroup acylated to a mixture of fatty acids; h) diacylglycerol lipid class with isotopically-labeled palmitate (16:0) in the sn-1 position and a mixture of fatty acids in the sn-2 position; i) free fatty acid lipid class with isotopically-labeled fatty acids or 15:1 or 17:1; and/or j) ceramide lipid classes with an isotopically-labeled sphingolipid backbone and a fatty acid mixture appropriate to the ceramide class.

In one example, the ceramide lipid class may be comprised of the following sphingolipid backbones: sphingosine, dihydrosphingosine, phytosphingosine, or 6-hydroxysphingosine.

The reagents described herein may be combined as an article of manufacture, for example, as a kit.

Complex lipids are categorized by classes; each class is defined by the head group moiety on the lipid (e.g. PC has a phosphocholine headgroup, CE has a cholesterol headgroup). Within a lipid class, there are many molecular species that are defined by the fatty acids that are linked to the headgroup. Because fatty acids have diverse chemical structures, each lipid class is comprised of a large number of diverse components which results in distinct lipid molecular species. To quantify a lipid class, one needs to quantify each of these molecular species and sum them accurately.

In contrast to traditional lipidomic strategies which typically use only a single internal standard per broad lipid class (e.g., phospholipids), here, methods are provided for synthesizing internal standards containing a mixture of fatty acids (up to 10 fatty acids per lipid class). In the methods, the fatty acids in the internal standard mixture (IS mixture) are selected to represent the diversity of chemical structures (lipid molecular species) found in the lipid classes present in the sample type to be analyzed. Table 1 shows the concentration of each fatty acid measured for each corresponding lipid class according to the methods of the present disclosure, and the remaining fatty acids in each lipid class were assigned to the closest internal standard analogue and assigned that measured value; the total concentration for each lipid class was calculated by adding the values (measured and assigned) of all molecular species for that lipid class.

In one embodiment, internal standards are provided for each of 10 lipid classes according the composition of fatty acids shown in Table 1. The lipid classes for the internal standards are shown in the first row of Table 1, and the fatty acid "R" groups are listed in column 1 of Table 1. In Table 1, "d" refers to the addition of a deuterium label. For example, 16:0-d9 refers to palmitate with 9 deuterium atoms added

TABLE 1

Composition of fatty acid mixtures for synthesizing lipid internal standards

| | PC | O-PC | LPC | PE | P-PE | LPE | TG | DG | CE | SM |
|---|---|---|---|---|---|---|---|---|---|---|
| R | 16:0-d9/R | O-16:0-d9/R | 16:0-d9 | 18:0-d9/R | P-18:0-d9/R | 18:0-d9 | 16:0-d9/18:1n9/R | 16:0-d9/R | CE-d6/R | 18:1n9-d9/R |
| d | — | — | 100% | — | — | 100% | — | — | — | — |
| FA14:0 | — | — | — | — | — | — | — | — | — | — |
| FA16:0 | — | — | — | — | — | — | 20% | 20% | 5% | 25% |
| FA18:0 | — | — | — | — | — | — | 20% | 20% | — | — |
| FA24:0 | — | — | — | — | — | — | — | — | — | 25% |
| FA16:1n7 | 5% | 5% | — | — | — | — | — | — | 5% | — |
| FA18:1n9 | 20% | 20% | — | 20% | 20% | — | 20% | 20% | 20% | 25% |
| FA24:1n9 | — | — | — | — | — | — | — | — | — | 25% |
| FA18:2n6 | 20% | 20% | — | 20% | 20% | — | 20% | 20% | 50% | — |
| FA18:3n3 | 5% | 5% | — | 5% | 5% | — | 5% | 5% | — | — |
| FA20:3n6 | 5% | 5% | — | 5% | 5% | — | 5% | — | 5% | — |
| FA20:4n6 | 20% | 20% | — | 20% | 20% | — | 5% | 5% | 5% | — |
| FA20:5n3 | 5% | 5% | — | 5% | 5% | — | — | 5% | 5% | — |
| FA22:4n6 | 5% | 5% | — | — | — | — | — | — | — | — |
| FA22:5n3 | 5% | 5% | — | 5% | 5% | — | — | — | — | — |
| FA22:6n3 | 10% | 10% | — | 20% | 20% | — | 5% | 5% | 5% | — |
| FA17:1n7 | — | — | — | — | — | — | — | — | — | — |
| Sum | 100% | 100% | 100% | 100% | 100% | 100% | 100% | 100% | 100% | 100% |
| Count | 10 | 10 | 1 | 8 | 8 | 1 | 8 | 8 | 8 | 4 |

Figure 2A:
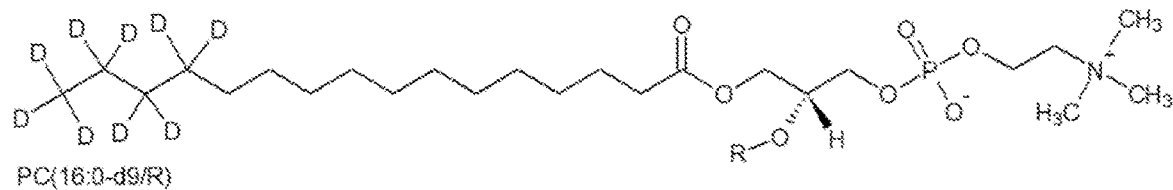
FIG. 2A shows the structure of phosphatidylcholine (PC) internal standard deuterated palmitate (16:0) in the sn-1 position and the fatty acid "R" in the sn-2 position according to one or more embodiments of the present disclosure.
Figure 2B:
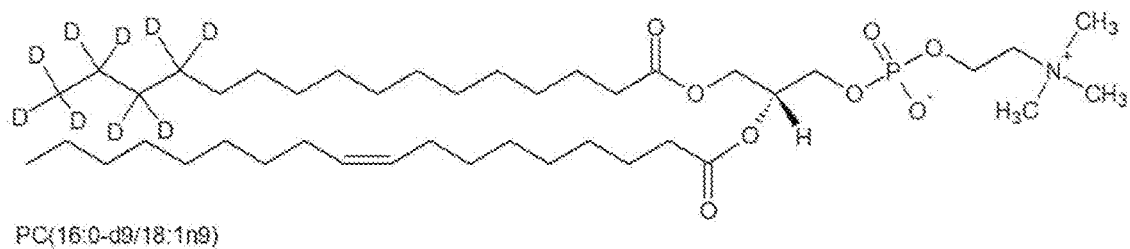
FIG. 2B shows the structure of phosphatidylcholine (PC) internal standard with the exemplary fatty acid oleate (18:1n9) in the sn-2 position.
Figure 2C:
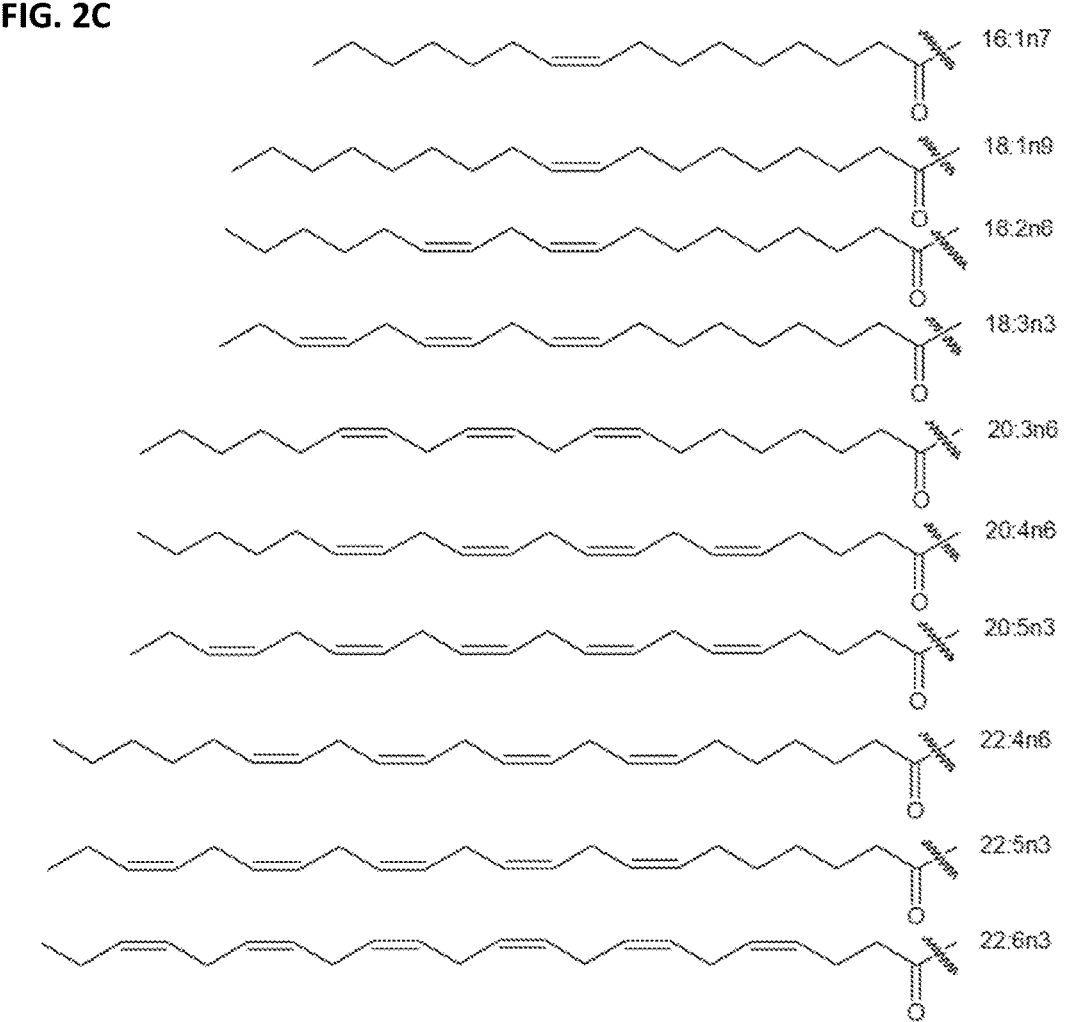
FIG. 2C shows the structure of phosphatidylcholine (PC) internal standard with ten exemplary fatty acids for acylating into the sn-2 position.

In one embodiment, exemplary internal standard components are provided for phosphatidylcholine and o-phosphatidylcholine, and the composition of fatty acids at the sn-2 position (sn-2 fatty acids) for these internal standards are displayed in Table 2. The structures of phosphatidylcholine and sn-2 fatty acids comprising the mixture are shown in FIG. 2. The structure of phosphatidylcholine with deuterated palmitate (16:0) in the sn-1 position and a fatty acid residue, denoted by "R", in the sn-2 position is shown in FIG. 2A. The structure of phosphatidylcholine with deuterated palmitate (16:0) in the sn-1 position and oleate (18:1n9), as an exemplary fatty acid, in the sn-2 position is shown in FIG. 2B. The structures of ten fatty acids (16:1n7, 18:1n9, 18:2n6, 18:3n3, 20:3n6, 20:4n6, 20:5n3, 22:4n6, 22:5n3, 22:6n3) in the fatty acid mixture for acylating into the sn-2 position of phosphatidylcholine are shown in FIG. 2C.

TABLE 2

Composition of sn-2 fatty acids for phosphatidylcholine and o-phosphatidylcholine internal standards

| sn2-FA | % | ID | Systematic Name |
|---|---|---|---|
| 16:1n7 | 5% | PC (16:0-d9/16:1n7) | 1-(hexadecanoyl-d9)-2-(9Z-hexadecenoyl)-sn-glycero-3-phosphocholine |
| 18:1n9 | 20% | PC (16:0-d9/18:1n9) | 1-(hexadecanoyl-d9)-2-(9Z-octadecenoyl)-sn-glycero-3-phosphocholine |
| 18:2n6 | 20% | PC (16:0-d9/18:2n6) | 1-(hexadecanoyl-d9)-2-(9Z,12Z-octadecadienoyl)-sn-glycero-3-phosphocholine |
| 18:3n3 | 5% | PC (16:0-d9/18:3n3) | 1-(hexadecanoyl-d9)-2-(9Z,12Z,15Z-octadecatrienoyl)-sn-glycero-3-phosphocholine |
| 20:3n6 | 5% | PC (16:0-d9/20:3n6) | 1-(hexadecanoyl-d9)-2-(8Z,11Z,14Z-eicosatrienoyl)-sn-glycero-3-phosphocholine |
| 20:4n6 | 20% | PC (16:0-d9/20:4n6) | 1-(hexadecanoyl-d9)-2-(5Z,8Z,11Z,14Z-eicosatetraenoyl)-sn-glycero-3-phosphocholine |
| 20:5n3 | 5% | PC (16:0-d9/20:5n3) | 1-(hexadecanoyl-d9)-2-(5Z,8Z,11Z,14Z,17Z-eicosapentaenoyl)-sn-glycero-3-phosphocholine |
| 22:4n6 | 5% | PC (16:0-d9/22:4n6) | 1-(hexadecanoyl-d9)-2-(7Z,10Z,13Z,16Z-docosatetraenoyl)-sn-glycero-3-phosphocholine |

TABLE 2-continued

Composition of sn-2 fatty acids for phosphatidylcholine and o-phosphatidylcholine internal standards

| sn2-FA | % | ID | Systematic Name |
|---|---|---|---|
| 22:5n3 | 5% | PC (16:0-d9/22:5n3) | 1-(hexadecanoyl-d9)-2-(7Z,10Z,13Z,16Z,19Z-docosapentaenoyl)-sn-glycero-3-phosphocholine |
| 22:6n3 | 10% | PC (16:0-d9/22:6n3) | 1-(hexadecanoyl-d9)-2-(4Z,7Z,10Z,13Z,16Z,19Z-docosahexaenoyl)-sn-glycero-3-phosphocholine |

Figure 3:
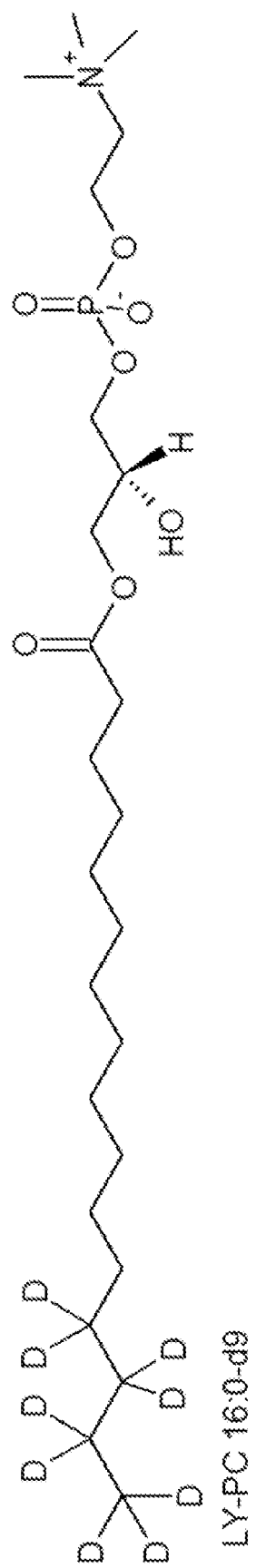
FIG. 3 shows the structure of a lysophosphatidylcholine (LPC) internal standard according to one or more embodiments of the present disclosure.

In one embodiment, exemplary internal standards are provided for lysophosphatidylcholine internal standards and the structure is shown in FIG. 3.

Figure 4A:
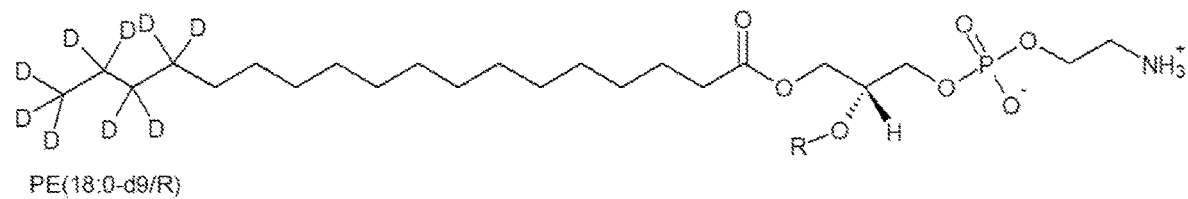
FIG. 4A shows the structure of phosphatidylethanolamine (PE) internal standard deuterated octadecanoic acid (18:0) in the sn-1 position and the fatty acid "R" in the sn-2 position according to one or more embodiments of the present disclosure.
Figure 4B:
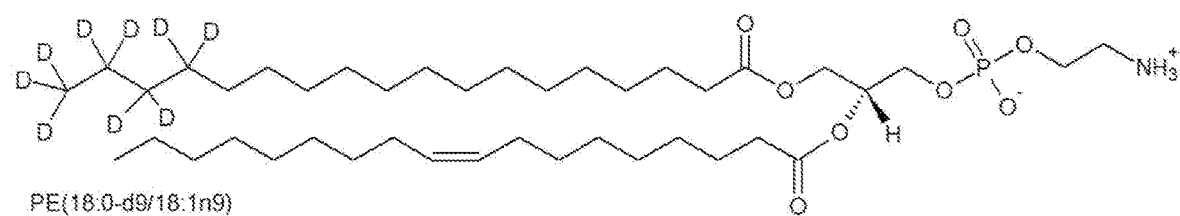
FIG. 4B shows the structure of phosphatidylethanolamine (PE) internal standard with the exemplary fatty acid oleate (18:1n9) in the sn-2 position according to one or more embodiments of the present disclosure.
Figure 4C:
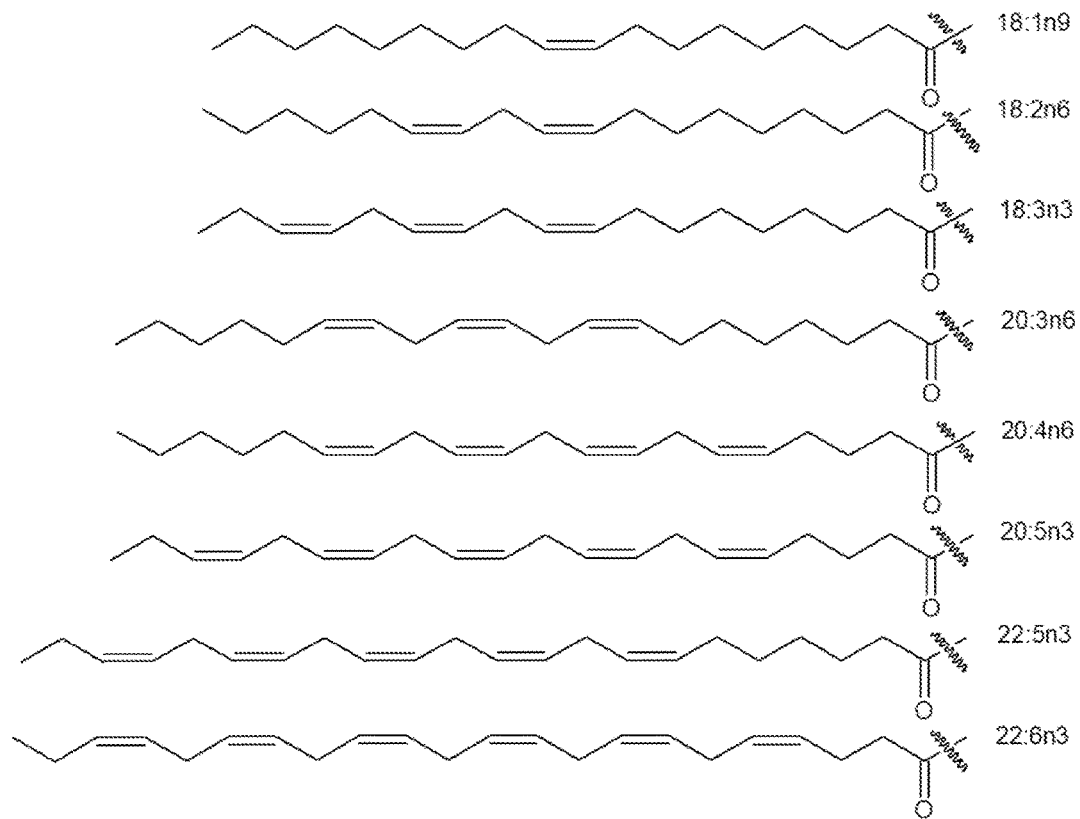
FIG. 4C shows the structure of phosphatidylethanolamine (PE) internal standard with eight exemplary fatty acids for acylating into the sn-2 position according to one or more embodiments of the present disclosure.

For the phosphatidylethanolamine and p-phosphatidylethanolamine internal standards, the composition of sn-2 fatty acids are listed in Table 3. The structures of phosphatidylethanolamine and sn-2 fatty acids comprising the mixture are shown in FIG. 4. The structure of phosphatidylethanolamine with deuterated stearate (18:0) in the sn-1 position and the fatty acid residue, denoted by "R", in the sn-2 position is shown in FIG. 4A. The structure of phosphatidylethanolamine with deuterated stearate (18:0) in the sn-1 position and oleate (18:1n9) as an exemplary fatty acid in the sn-2 position is shown in FIG. 4B. The structures of eight fatty acids (18:1n9, 18:2n6, 18:3n3, 20:3n6, 20:4n6, 20:5n3, 22:5n3, 22:6n3) in the fatty acid mix for acylating into the sn-2 position of phosphatidylethanolamine are shown in FIG. 4C.

TABLE 3

Composition of sn-2 fatty acids for phosphatidylethanolamine and p-phosphatidylethanolamine internal standards

| sn2-FA | % | ID | Systematic Name |
|---|---|---|---|
| 18:1n9 | 20% | PE (18:0-d9/18:1n9) | 1-(octadecanoyl-d9)-2-(9Z-octadecenoyl)-sn-glycero-3-phosphoethanolamine |
| 18:2n6 | 20% | PE (18:0-d9/18:2n6) | 1-(octadecanoyl-d9)-2-(9Z,12Z-octadecadienoyl)-sn-glycero-3-phosphoethanolamine |

TABLE 3-continued

Composition of sn-2 fatty acids for phosphatidylethanolamine and p-phosphatidylethanolamine internal standards

| sn2-FA | % | ID | Systematic Name |
|---|---|---|---|
| 18:3n3 | 5% | PE (18:0-d9/18:3n3) | 1-(octadecanoyl-d9)-2-(9Z,12Z,15Z-octadecatrienoyl)-sn-glycero-3-phosphoethanolamine |
| 20:3n6 | 5% | PE (18:0-d9/20:3n6) | 1-(octadecanoyl-d9)-2-(8Z,11Z,14Z-eicosatrienoyl)-sn-glycero-3-phosphoethanolamine |
| 20:4n6 | 20% | PE (18:0-d9/20:4n6) | 1-(octadecanoyl-d9)-2-(5Z,8Z,11Z,14Z-eicosatetraenoyl)-sn-glycero-3-phosphoethanolamine |
| 20:5n3 | 5% | PE (18:0-d9/20:5n3) | 1-(octadecanoyl-d9)-2-(5Z,8Z,11Z,14Z,17Z-eicosapentaenoyl)-sn-glycero-3-phosphoethanolamine |
| 22:5n3 | 5% | PE (18:0-d9/22:5n3) | 1-(octadecanoyl-d9)-2-(7Z,10Z,13Z,16Z,19Z-docosapentaenoyl)-sn-glycero-3-phosphoethanolamine |
| 22:6n3 | 20% | PE (18:0-d9/22:6n3) | 1-(octadecanoyl-d9)-2-(4Z,7Z,10Z,13Z,16Z,19Z-docosahexaenoyl)-sn-glycero-3-phosphoethanolamine |

Figure 5:
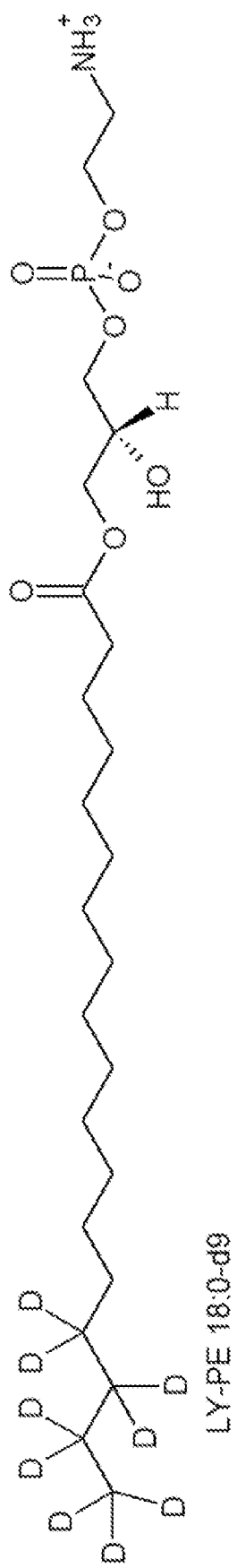
FIG. 5 shows the structure of a lysophosphatidylethanolamine internal standard according to one or more embodiments of the present disclosure.

In one embodiment, exemplary internal standards are provided for lysophosphatidylethanolamine and the structure is shown in FIG. 5.

Figure 6A:
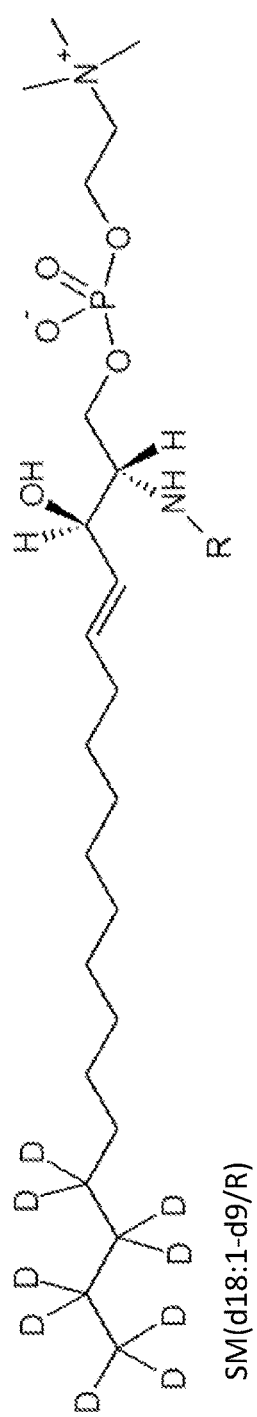
FIG. 6A shows the structure of sphingomyelin internal standard deuterium-labeled sphingosine at the first position, and the fatty acid "R" in the sn-2 position according to one or more embodiments of the present disclosure.
Figure 6B:
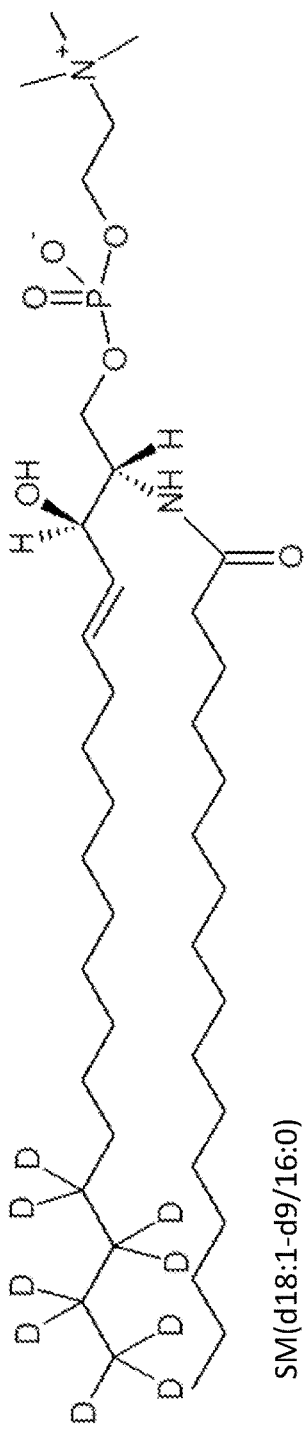
FIG. 6B shows the structure of sphingomyelin internal standard with the exemplary fatty acid palmitate (16:0) in the sn-2 position according to one or more embodiments of the present disclosure.
Figure 6C:
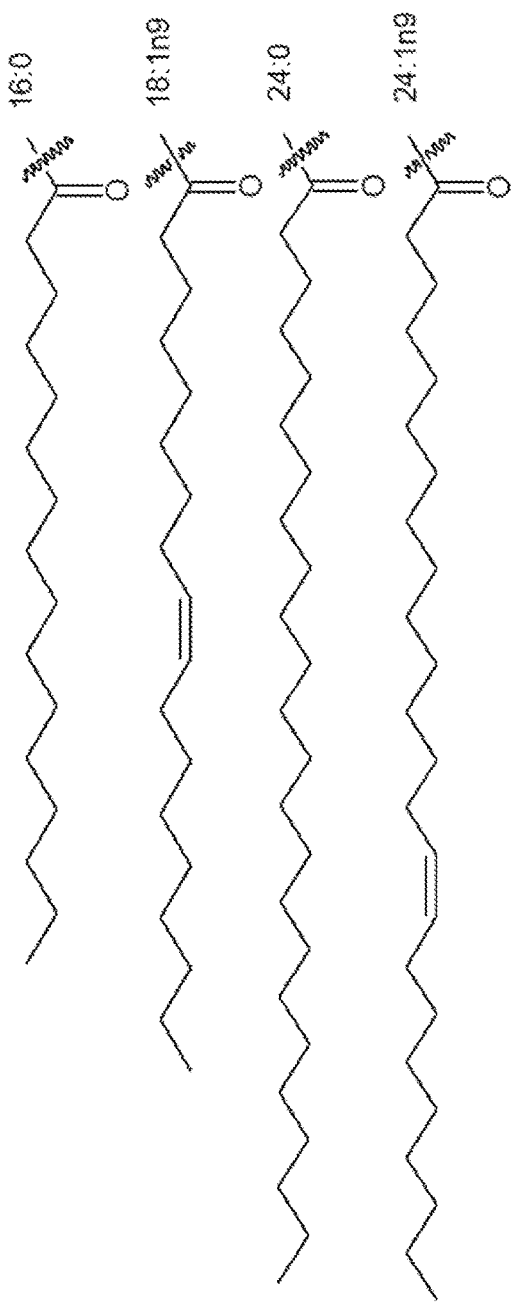
FIG. 6C shows the structure of sphingomyelin internal standard with four exemplary fatty acids for acylating into the sn-2 position according to one or more embodiments of the present disclosure.

In one embodiment, exemplary internal standards are provided for sphingomyelin and the composition of fatty acids are displayed in Table 4. The structures of sphingomyelin and sn-2 fatty acids comprising the mixture are shown in FIG. 6. The structure of sphingomyelin with deuterium-labeled sphingosine at the first position, and the fatty acid residue, denoted by "R", in the sn-2 position is shown in FIG. 6A. The structure of sphingomyelin with deuterium-labeled sphingosine at the first position, and palmitate (16:0), as an exemplary fatty acid, in the sn-2 position is shown in FIG. 6B. The structures of four fatty acids (16:0, 18:1n9, 24:0, 24:1n9) in the fatty acid mix for acylating into the sn-2 position of sphingomyelin are shown in FIG. 6C.

TABLE 4

Composition of fatty acids for sphingomyelin internal standard

| sn2-FA | % | ID | Systematic Name |
|---|---|---|---|
| 16:0 | 25% | SM (d18:1-d9/16:0) | N-(hexadecanoyl)-(sphing-d9)-4-enine-1-phosphocholine |
| 18:1n9 | 25% | SM (d18:1-d9/18:1n9) | N-(9Z-octadecenoyl)-(sphing-d9)-4-enine-1-phosphocholine |
| 24:0 | 25% | SM (d18:1-d9/24:0) | N-(tetracosanoyl)-(sphing-d9)-4-enine-1-phosphocholine |
| 24:1n9 | 25% | SM (d18:1-d9/24:1n9) | N-(15Z-tetracosenoyl)-(sphing-d9)-4-enine-1-phosphocholine |

Figure 7A:
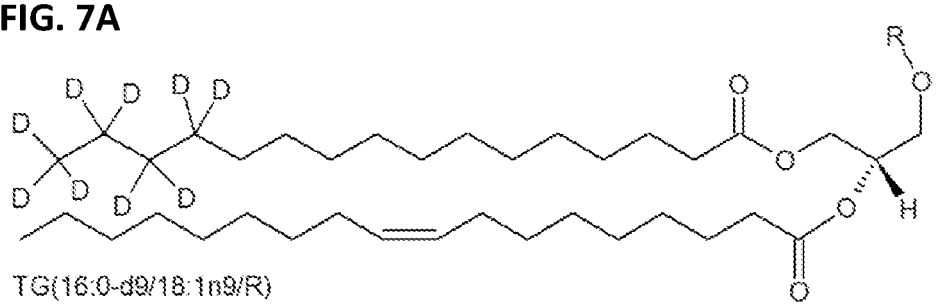
FIG. 7A shows the structure of triacylglycerol internal standard deuterium-labeled palmitate (16:0) at the sn-1 position, oleate (18:1n9) at the sn-2 position, and the fatty acid "R" in the sn-3 position according to one or more embodiments of the present disclosure.
Figure 7B:
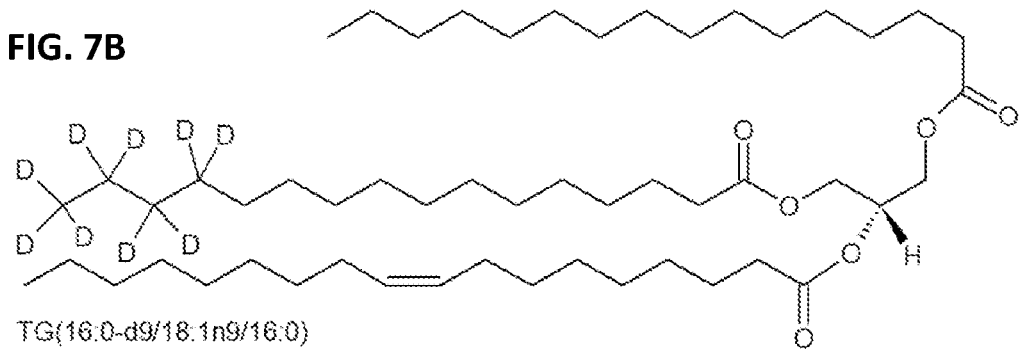
FIG. 7B shows the structure of triacylglycerol internal standard with the exemplary fatty acid palmitate (16:0) in the sn-3 position, according to one or more embodiments of the present disclosure.
Figure 7C:
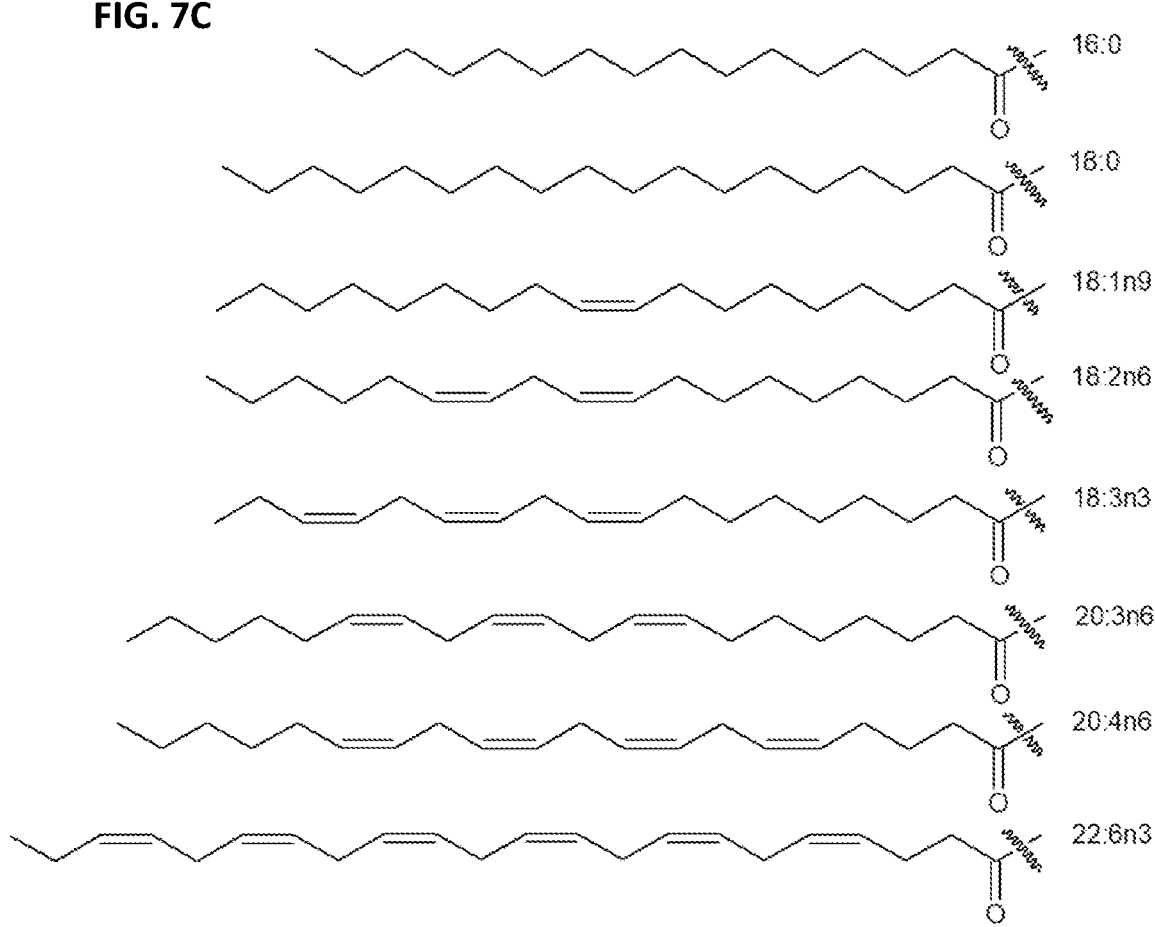
FIG. 7C shows the structure of triacylglycerol internal standard with eight exemplary fatty acids for acylating into the sn-3 position according to one or more embodiments of the present disclosure.

In one embodiment, exemplary internal standards are provided for triacylglycerol and the composition of sn-3 fatty acids are listed in Table 5. The structures of triacylglycerol and sn-3 fatty acids comprising the mixture are shown in FIG. 7. The structure of triacylglycerol with deuterium-labeled palmitate (16:0) at the sn-1 position, oleate (18:1n9) at the sn-2 position, and the fatty acid "R" in the sn-3 position is shown in FIG. 7A. The structure of triacylglycerol with deuterium-labeled palmitate (16:0) at the sn-1 position, oleate (18:1n9) at the sn-2 position, and palmitate (16:0) as an exemplary fatty acid in the sn-3 position is shown in FIG. 7B. The structures of eight fatty acids (16:0, 18:0, 18:1n9, 18:2n6, 18:3n3, 20:3n6, 20:4n6, 22:6n3) in the fatty acid mix for labeling the sn-3 position of triacylglycerol are shown in FIG. 7C.

TABLE 5

Composition of sn-3 fatty acids for triacylglycerol internal standard

| sn3-FA | % | ID | Systematic Name |
|---|---|---|---|
| 16:0 | 20% | TG (16:0-d9/18:1n9/16:0) | 1-(hexadecanoyl-d9)-2-(9Z-octadecenoyl)-3-hexadecanoyl-sn-glycerol |
| 18:0 | 20% | TG (16:0-d9/18:1n9/18:0) | 1-(hexadecanoyl-d9)-2-(9Z-octadecenoyl)-3-octadecanoyl-sn-glycerol |
| 18:1n9 | 20% | TG (16:0-d9/18:1n9/18:1n9) | 1-(hexadecanoyl-d9)-2-(9Z-octadecenoyl)-3-(9Z-octadecenoyl)-sn-glycerol |
| 18:2n6 | 20% | TG (16:0-d9/18:1n9/18:2n6) | 1-(hexadecanoyl-d9)-2-(9Z-octadecenoyl)-3-(9Z,12Z-octadecadienoyl)-sn-glycerol |
| 18:3n3 | 5% | TG (16:0-d9/18:1n9/18:3n3) | 1-(hexadecanoyl-d9)-2-(9Z-octadecenoyl)-3-(9Z,12Z,15Z-octadecatrienoyl)-sn-glycerol |
| 20:3n6 | 5% | TG (16:0-d9/18:1n9/20:3n6) | 1-(hexadecanoyl-d9)-2-(9Z-octadecenoyl)-3-(8Z,11Z,14Z-eicosatrienoyl)-sn-glycerol |
| 20:4n6 | 5% | TG (16:0-d9/18:1n9/20:4n6) | 1-(hexadecanoyl-d9)-2-(9Z-octadecenoyl)-3-(5Z,8Z,11Z,14Z-eicosatetraenoyl)-sn-glycerol |
| 22:6n3 | 5% | TG (16:0-d9/18:1n9/22:6n3) | 1-(hexadecanoyl-d9)-2-(9Z-octadecenoyl)-3-(4Z,7Z,10Z,13Z,16Z,19Z-docosahexaenoyl)-sn-glycerol |

Figure 8A:
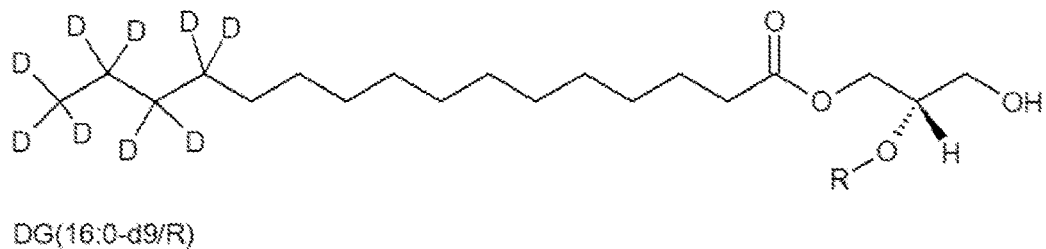
FIG. 8A shows the structure of diacylglycerol internal standard deuterium-labeled palmitate (16:0) at the sn-1 position, and the fatty acid "R" in the sn-2 position according to one or more embodiments of the present disclosure.
Figure 8B:
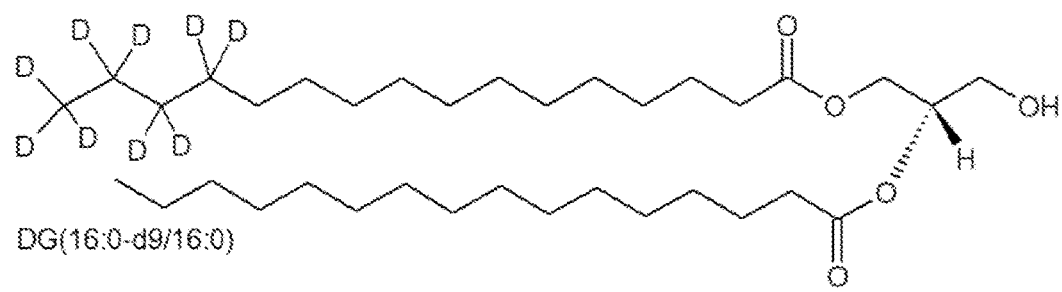
FIG. 8B shows the structure of diacylglycerol internal standard with the exemplary fatty acid palmitate (16:0) in the sn-2 position according to one or more embodiments of the present disclosure.
Figure 8C:
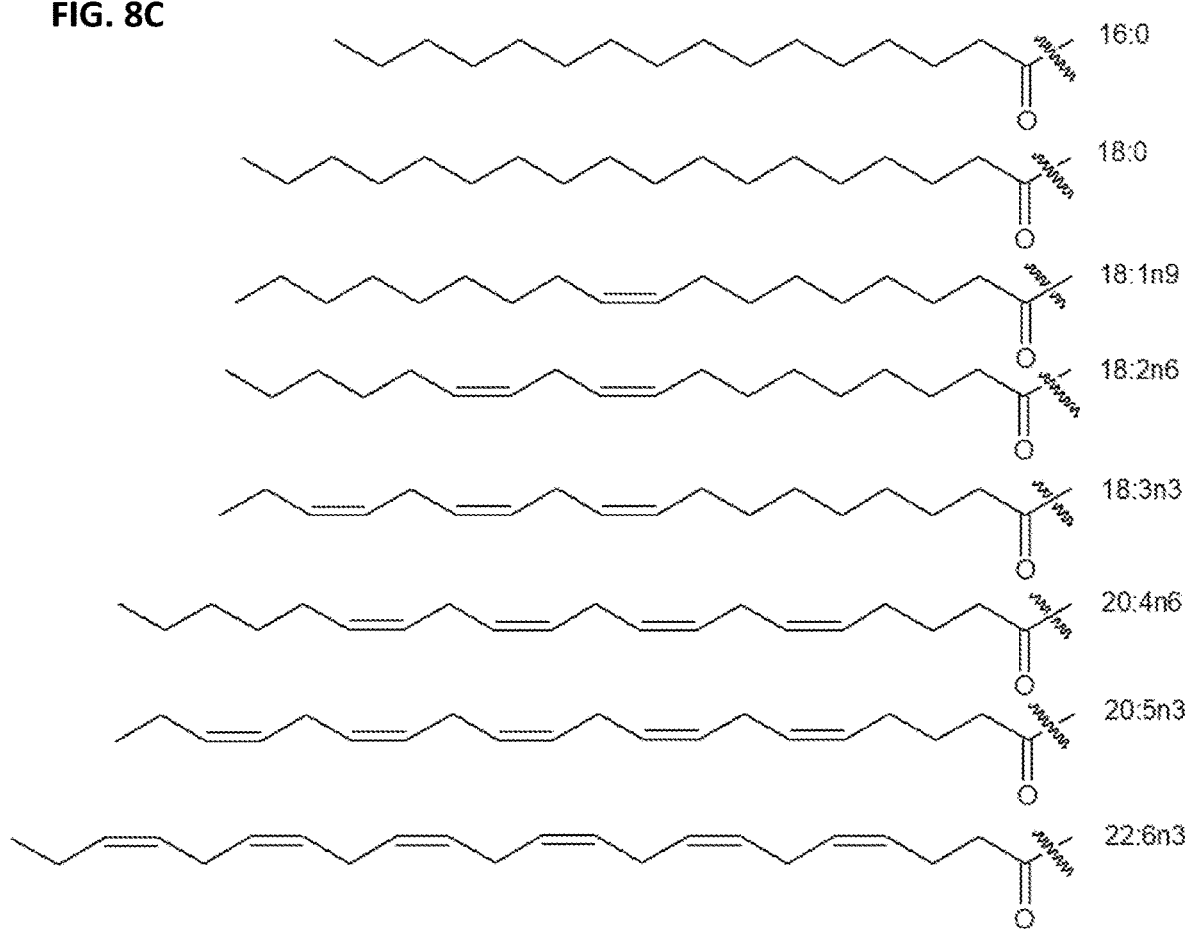
FIG. 8C shows the structure of diacylglycerol internal standard with eight exemplary fatty acids for acylating into the sn-2 position according to one or more embodiments of the present disclosure.

In one embodiment, exemplary internal standards are provided for diacylglycerol and the composition of sn-2 fatty acids are listed in Table 6. The structures of diacylglycerol and sn-2 fatty acids comprising the mixture are shown in FIG. 8. The structure of diacylglycerol with deuterium-labeled palmitate (16:0) at the sn-1 position, and a fatty acid residue, denoted by "R", in the sn-2 position is shown in FIG. 8A. The structure of diacylglycerol with deuterium-labeled palmitate (16:0) at the sn-1 position, and palmitate (16:0), as an exemplary fatty acid, in the sn-2 position is shown in FIG. 8B. The structures of eight fatty acids (16:0, 18:0, 18:1n9, 18:2n6, 18:3n3, 20:4n6, 20:5n3, 22:6n3) in the fatty acid mix for labeling the sn-2 position of diacylglycerol are shown in FIG. 8C.

TABLE 6

Composition of sn-2 fatty acids for diacylglycerol internal standard

| sn2-FA | % | ID | Systematic Name |
|---|---|---|---|
| 16:0 | 20% | DG (16:0-d9/16:0) | 1-(hexadecanoyl-d9)-2-hexadecanoyl-sn-glycerol |
| 18:0 | 20% | DG (16:0-d9/18:0) | 1-(hexadecanoyl-d9)-2-octadecanoyl-sn-glycerol |
| 18:1n9 | 20% | DG (16:0-d9/18:1n9) | 1-(hexadecanoyl-d9)-2-(9Z-octadecenoyl)-sn-glycerol |
| 18:2n6 | 20% | DG (16:0-d9/18:2n6) | 1-(hexadecanoyl-d9)-2-(9Z,12Z-octadecadienoyl)-sn-glycerol |
| 18:3n3 | 5% | DG (16:0-d9/18:3n3) | 1-(hexadecanoyl-d9)-2-(9Z,12Z,15Z-octadecatrienoyl)-sn-glycerol |
| 20:4n6 | 5% | DG (16:0-d9/20:4n6) | 1-(hexadecanoyl-d9)-2-(5Z,8Z,11Z,14Z-eicosatetraenoyl)-sn-glycerol |
| 20:5n3 | 5% | DG (16:0-d9/20:5n3) | 1-(hexadecanoyl-d9)-2-(5Z,8Z,11Z,14Z,17Z-eicosapentaenoyl)-sn-glycerol |
| 22:6n3 | 5% | DG (16:0-d9/22:6n3) | 1-(hexadecanoyl-d9)-2-(4Z,7Z,10Z,13Z,16Z,19Z-docosahexaenoyl)-sn-glycerol |

Figure 9B:
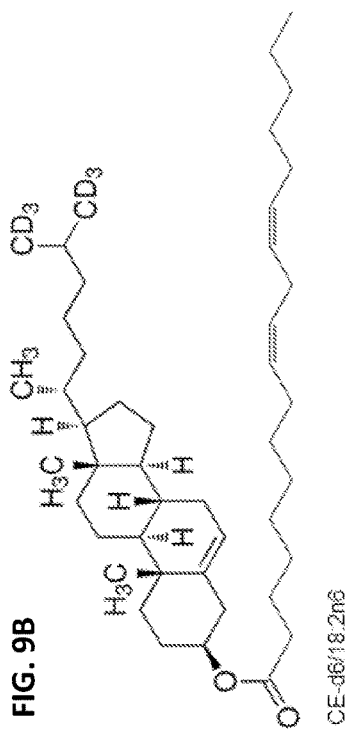
FIG. 9B shows the structure of cholesteryl ester internal standard with the exemplary fatty acid linoleate (18:2n6) acylated to the hydroxyl group according to one or more embodiments of the present disclosure.
Figure 9A:
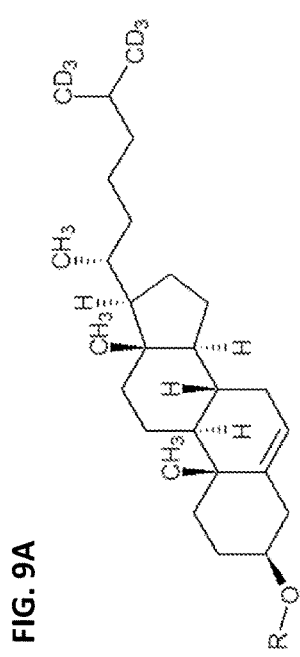
FIG. 9A shows the structure of cholesteryl ester internal standard with deuterium labels at the n6 position, and the fatty acid "R" acylated to the hydroxyl group according to one or more embodiments of the present disclosure.
Figure 9C:
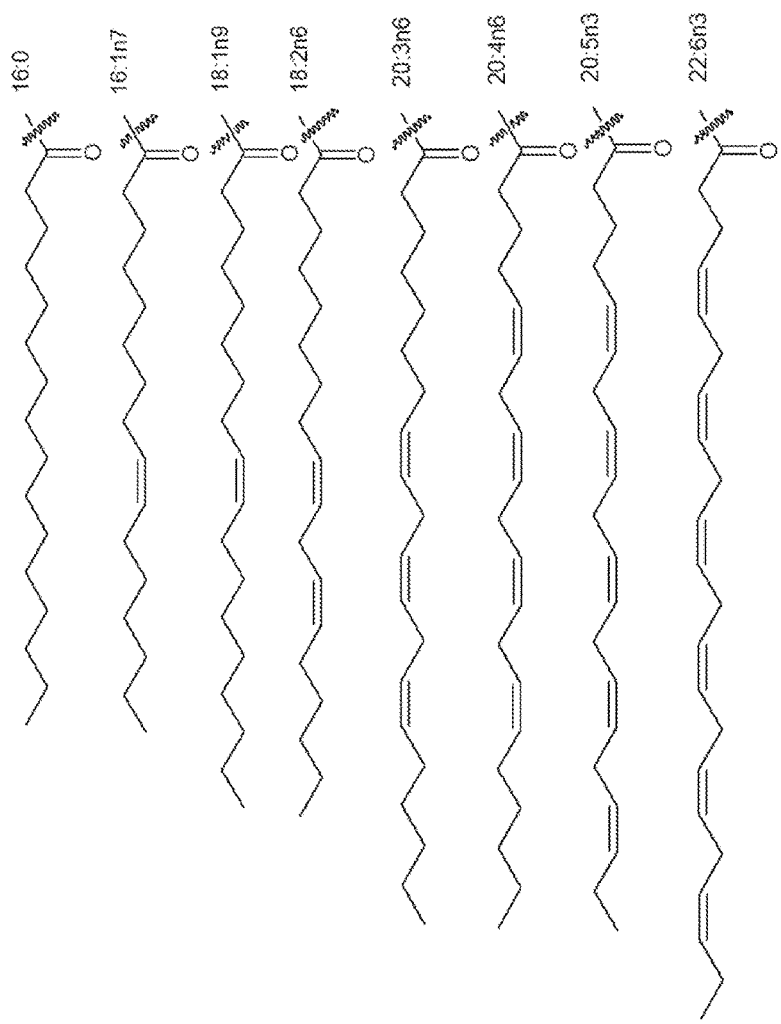
FIG. 9C shows the structure of cholesteryl ester internal standard with eight exemplary fatty acids for use in acylating to the hydroxyl group according to one or more embodiments of the present disclosure.

In one embodiment, exemplary internal standards are provided for cholesteryl ester and the composition of fatty acids is listed in Table 7. The structures of cholesteryl ester and fatty acids comprising the mixture are shown in FIG. 9. The structure of cholesteryl ester with deuterium labels at the n6 position, and the fatty acid "R" acylated to the hydroxyl group is shown in FIG. 9A. The structure of cholesteryl ester with deuterium labels at the n6 position, and linoleate (18:2n6), as the exemplary fatty acid, acylated to the hydroxyl group is shown in FIG. 9B. The structure of eight fatty acids (16:0, 16:1n7, 18:1n9, 18:2n6, 20:3n6, 20:4n6, 20:5n3, 22:6n3) in the fatty acid mix for use in acylating the hydroxyl group of cholesteryl ester are shown in FIG. 9C.

TABLE 7

Composition of fatty acids for cholesteryl ester internal standard

| Fatty Acid | % | ID | Systematic Name |
|---|---|---|---|
| 16:0 | 5% | CE-d6/16:0 | cholest-5-en-3B-yl-d6 hexadecanoate |
| 16:1n7 | 5% | CE-d6/16:1n7 | cholest-5-en-3B-yl-d6 (9Z-hexadecenoate) |
| 18:1n9 | 20% | CE-d6/18:1n9 | cholest-5-en-3B-yl-d6 (9Z-octadecenoate) |
| 18:2n6 | 50% | CE-d6/18:2n6 | cholest-5-en-3B-yl-d6 (9Z,12Z-octadecadienoate) |
| 20:3n6 | 5% | CE-d6/20:3n6 | cholest-5-en-3B-yl-d6 (8Z,11Z,14Z-eicosatrienoate) |
| 20:4n6 | 5% | CE-d6/20:4n6 | cholest-5-en-3B-yl-d6 (5Z,8Z,11Z,14Z-eicosatetraenoate) |
| 20:5n3 | 5% | CE-d6/20:5n3 | cholest-5-en-3B-yl-d6 (5Z,8Z,11Z,14Z,17Z-eicosapentaenoate) |
| 22:6n3 | 5% | CE-d6/22:6n3 | cholest-5-en-3B-yl-d6 (4Z,7Z,10Z,13Z,16Z,19Z-docosahexaenoate) |

Figure 10A:
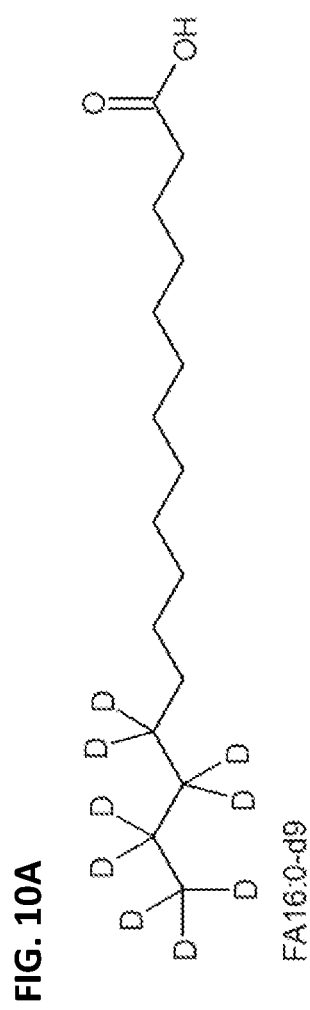
FIG. 10A shows the structure of exemplary free fatty acid deuterated palmitate according to one or more embodiments of the present disclosure.
Figure 10B:
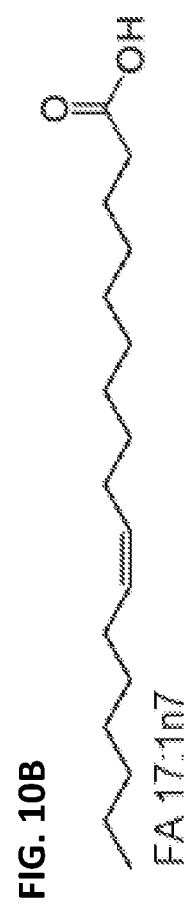
FIG. 10B shows the structure of exemplary free fatty acid 17:1n7 for the internal standard mixture according to one or more embodiments of the present disclosure.

In one embodiment, exemplary internal standards are provided for free fatty acids and the composition of fatty acids are listed in Table 8. The structures of the free fatty acids comprising the mixture are shown in FIG. 10. The structure of the free fatty acid palmitate (16:0) with deuterium labels is shown in FIG. 10A. The structure of the free fatty acid, 17:1n7, is shown in FIG. 10B.

TABLE 8

Composition of free fatty acid internal standard

| % | ID | Systematic Name |
|---|---|---|
| 50% | FA 16:0-d9 | Hexadonic-d9 acid |
| 50% | FA 17:1n7 | 10Z-heptadecenoic acid |

Methods for Generating Lipid Internal Standards

In one embodiment of the present disclosure a method is provided for synthesizing one or more mixtures of lipid molecules for use as an internal standard representative of the composition of lipid molecular species present in one or more corresponding lipid classes in a sample of interest, the method comprising one or more of: attaching a mixture of at least two different isotopically-labeled fatty acids to a lipid backbone at a single position through an acylation reaction for a lipid class having at least one acyl group; attaching a mixture of at least two different fatty acids to an isotopically-labeled lipid backbone at a single position through an acylation reaction for a lipid class having at least one acyl group; or attaching a single isotopically-labeled fatty acid to a lipid backbone at a first position through an acylation reaction for a lipid class having at least two fatty acids and attaching a mixture of at least two different fatty acids to a separate position on the lipid backbone through an acylation reaction, wherein the mixture of the at least two different fatty acids is representative of the fatty acids that occur in the corresponding lipid class in the sample of interest, and wherein each of the fatty acids in the mixture is present at a ratio representative of the ratio of occurrence of the fatty acid in the lipid molecular species present in the corresponding lipid class in the sample of interest. The corresponding lipid class can include one or more of triacylglycerols, diacylglycerols, 1-monoacylglycerol, phospholipids, phosphatidylcholine, o-phosphatidylcholine, phosphatidylethanolamine, p-phosphatidylethanolamine, cholesteryl esters, lysophosphatidylcholine, lysophosphatidylethanolamine, lysophosphatidylserine, lysophosphatidylinositol, lysophosphatidylglycerol, lysophosphatidic acid, lyso CDP-diacylglycerol, CDP-diacylglycerol, sphingomyelin, cardiolipin, phosphatidylserine, phosphatidylinositol, phosphatidylglycerol, phosphatidic acid, ceramide, lactosylceramide, glucosylceramide, phytoceramide, 6-hydroxyceramide, cerebroside, ganglioside, wax esters, or wax diesters. The one or more mixtures of fatty acids in each of the one or more mixtures of lipid molecules can include one or more of the mixtures of lipid molecular species listed in Table 1, Table 2, Table 3, Table 4, Table 5, Table 6, or Table 7. The one or more mixtures of fatty acids in each of the one or more mixtures of lipid molecules can consist of one or more of the mixtures of lipid molecular species listed in Table 1, Table 2, Table 3, Table 4, Table 5, Table 6, or Table 7.

In one embodiment of the present disclosure a method is provided for synthesizing one or more mixtures of lipid molecules representative of the composition of lipid molecular species present in one or more corresponding lipid classes in a sample of interest, the method comprising: attaching an isotopically-labeled fatty acid at a first position on a lipid backbone through an acylation reaction for a lipid class having at least two acyl groups; and attaching a mixture of at least two different fatty acids to the lipid backbone at a separate position through an acylation reaction, wherein the mixture of fatty acids is representative of the fatty acids that occur in the corresponding lipid class in the sample of interest, and wherein each of the fatty acids in the mixture is present at a ratio representative of the ratio of occurrence of the fatty acid in the lipid molecules present in the corresponding lipid class in the sample of interest. In the method, the one or more lipid classes having at least two acyl groups can include triacylglycerols, diacylglycerols, phospholipids, phosphatidylcholine, o-phosphatidylcholine, phosphatidyletanolamine, p-phosphatidylethanolamine, sphingomyelin, cardiolipin, phosphatidylserine, phosphatidylinositol, phosphatidylglycerol, phosphatidic acid, CDP-diacylglycerol, ceramide, lactosylceramide, glucosylceramide, phytoceramide, 6-hydroxyceramide, cerebroside, ganglioside, or wax diesters. The one or more mixtures of fatty acids in each of the one or more mixtures of lipid molecules can include one or more of the mixtures of lipid molecular species listed in Table 1, Table 2, Table 3, Table 4, Table 5, or Table 6. The one or more mixtures of fatty acids in each of the one or more mixtures of lipid molecules can consist of one or more of the mixtures of lipid molecular species listed in Table 1, Table 2, Table 3, Table 4, Table 5, or Table 6.

In one embodiment of the present disclosure, a method is provided for synthesizing one or more mixtures of lipid molecules representative of the composition of lipid molecular species present in one or more corresponding lipid classes in a sample of interest, the method comprising: attaching a mixture of at least two different fatty acids to an isotopically-labeled lipid backbone at a single position through an acylation reaction for a lipid class having at least one acyl group, wherein the mixture of fatty acids is representative of the fatty acids that occur in the corresponding lipid class in the sample of interest, and wherein each of the fatty acids in the mixture is present at a ratio representative of the ratio of occurrence of the fatty acid in the lipid molecules present in the one corresponding lipid class in the sample of interest. In the method, the one or more lipid classes having at least one acyl group can comprise triacylglycerols, diacylglycerols, 1-monoacylglycerol, phospholipids, phosphatidylcholine, o-phosphatidylcholine, phosphatidylethanolamine, p-phosphatidylethanolamine, cholesteryl esters, lysophosphatidylcholine, lysophosphatidylethanolamine, lysophosphatidylserine, lysophosphatidylinositol, lysophosphatidylglycerol, lysophosphatidic acid, lyso CDP-diacylglycerol, CDP-diacylglycerol, sphingomyelin, cardiolipin, phosphatidylserine, phosphatidylinositol, phosphatidylglycerol, phosphatidic acid, ceramide, lactosylceramide, glucosylceramide, phytoceramide, 6-hydroxyceramide, cerebroside, ganglioside, wax esters, or wax diesters. The one or more mixtures of fatty acids in each of the one or more mixtures of lipid molecules can include one or more of the mixtures of lipid molecular species listed in Table 1, Table 2, Table 3, Table 4, Table 5, Table 6, or Table 7. The one or more mixtures of fatty acids in each of the one or more mixtures of lipid molecules can consist of one or more of the mixtures of lipid molecular species listed in Table 1, Table 2, Table 3, Table 4, Table 5, Table 6, or Table 7.

In the methods provided above, the sample of interest can be a complex mixture comprised of lipid molecules, a biological sample such as a plant sample or an animal sample. The animal sample may be from a mammal such as, for example, a human, a mouse, a non-human primate, a rabbit or other mammal, or a non-mammal sample such as, for example, a zebra fish sample. The biological sample of interest can include blood, plasma, serum, isolated lipoprotein fraction, saliva, urine, lymph fluid, and cerebrospinal fluid, a tissue sample, a cellular sample, or a skin sample.

In the methods provided above, the methods can further include performing quantitative fatty acid analysis to quantify the amount of each of the fatty acids in the mixture.

In the methods provided above, the fatty acid can be a saturated fatty acid.

In the methods provided above, the isotopic label can include any isotopic label including $^2$H, $^{13}$C, or $^{15}$N.

In one embodiment of the methods above, the first position on the lipid backbone can be a sn-1 position. The first position on the lipid backbone can be a sn-1 position and the separate position on the lipid backbone can be a sn-2 or a sn-3 position. In an alternate embodiment, the first position on the lipid backbone can be a sn-2 position. The first position can be a sn-2 and the separate position can be a sn-1 or sn-3 position. In another embodiment, the first position on the lipid backbone can be a sn-3 position. The first position can be a sn-3 position and the separate position can be a sn-1 or sn-2 position.

In the methods provided above, the one or more lipid classes having at least two acyl groups can consist of phosphatidylcholines or o-phosphatidylcholines, wherein the first position can be a sn-1 position and the separate position can be a sn-2 position, or wherein the first position can be a sn-2 position and the separate position can be a sn-1 position, wherein a deuterium-labeled hexadecanoyl-d9 (16:0-d9) can be present at the first position, and wherein the mixture of fatty acids at the separate position can comprise 9Z-hexadecenoyl (16:1n7), 9Z-octadecenoyl (18:1n9), 9Z,12Z-octadecadienoyl (18:2n6), 9Z,12Z,15Z-octadecatrienoyl (18:3n3), 8Z,11Z,14Z-eicosatrienoyl (20:3n6), 5Z,8Z,11Z,14Z-eicosatetraenoyl (20:4n6), 5Z,8Z,11Z,14Z,17Z-eicosapentaenoyl (20:5n3), 7Z,10Z,13Z,16Z-docosatetraenoyl (22:4n6), 7Z,10Z,13Z,16Z,19Z-docosapentaenoyl (22:5n3), and 4Z,7Z,10Z,13Z,16Z,19Z-docosahexaenoyl (22:6n3). The mixture of fatty acids at the sn-2 position can be present at the ratios shown in Table 2.

In the methods provided above, the one or more lipid classes having at least two acyl groups can consist of phosphatidylethanolamines and p-phosphatidylethanolamines, wherein the first position can be a sn-1 position and the separate position can be a sn-2 position, or wherein the first position can be a sn-2 position and the separate position can be a sn-1 position, wherein a deuterium-labeled octadecanoyl-d9 (18:0-d9) can be present at the first position, and wherein the mixture of fatty acids at the separate position can comprise 9Z-octadecenoyl (18:1n9), 9Z,12Z-octadecadienoyl (18:2n6), 9Z,12Z,15Z-octadecatrienoyl (18:3n3), 8Z,11Z,14Z-eicosatrienoyl (20:3n6), 5Z,8Z,11Z,14Z-eicosatetraenoyl (20:4n6), 5Z,8Z,11Z,14Z,17Z-eicosapentaenoyl (20:5n3), 7Z,10Z,13Z,16Z,19Z-docosapentaenoyl (22:5n3), and 4Z,7Z,10Z,13Z,16Z,19Z-docosahexaenoyl (22:6n3). The mixture of fatty acids at the separate position can be present at the ratios shown in Table 3.

In the methods provided above, the one or more lipid classes having at least two acyl groups can consist of sphingomyelins, wherein deuterium-labeled sphingosine can be present at the first position, and wherein the mixture of fatty acids at the separate position can comprise hexadecanoyl (16:0), 9Z-octadecenoyl (18:1n9), tetracosanoyl (24:0), and 15Z-tetracosenoyl (24:1n9). The mixture of fatty acids at the separate position can be present at the ratios shown in Table 4.

In the methods provided above, the one or more lipid classes having at least two acyl groups can consist of diacylglycerols, wherein the first position can be a sn-1 position and the separate position can be a sn-2 position, or wherein the first position can be a sn-2 position and the separate position can be a sn-1 position, wherein deuterium-labeled palmitate (16:0-d9) can be present at the first position, and wherein the mixture of fatty acids at the separate position can comprise hexadecanoyl (16:0), octadecanoyl (18:0), 9Z-octadecenoyl (18:1n9), 9Z,12Z-octadecadienoyl (18:2n6), 9Z,12Z,15Z-octadecatrienoyl (18:3n3), 5Z,8Z,11Z,14Z-eicosatetraenoyl (20:4n6), 5Z,8Z,11Z,14Z,17Z-eicosapentaenoyl (20:5n3), and 4Z,7Z,10Z,13Z,16Z,19Z-docosahexaenoyl (22:6n3). The mixture of fatty acids at the separate position can be present at the ratios shown in Table 6.

In the methods provided above, the one or more lipid classes having at least two acyl groups can consist of triacylglycerols, wherein the first position can be a sn-1 position and the separate position can be a sn-2 or sn-3 position, or wherein the first position can be an sn-2 position and the separate position can be an sn-1 or sn-3 position, or wherein the first position can be a sn-3 position and the separate position can be a sn-1 or sn-2 position, wherein deuterium-labeled palmitate (16:0-d9) can be present at the first position, wherein oleate (18:1n9) can be present at one separate position, and wherein the mixture of fatty acids at another separate position can comprise hexadecanoyl (16:0), octadecanoyl (18:0), 9Z-octadecenoyl (18:1n9), 9Z,12Z-octadecadienoyl (18:2n6), 9Z,12Z,15Z-octadecatrienoyl (18:3n3), 8Z,11Z,14Z-eicosatrienoyl (20:3n6), 5Z,8Z,11Z, 14Z-eicosatetraenoyl (20:4n6), and 4Z,7Z,10Z,13Z,16Z, 19Z-docosahexaenoyl (22:6n3). The mixture of fatty acids at the separate position can be present at the ratios shown in Table 5.

In the methods provided above, the one or more lipid classes having at least one acyl group can consist of cholesteryl esters, wherein the single position can be a hydroxyl group, and wherein the mixture of fatty acids attached to the hydroxyl group can comprise hexadecanoate (16:0), 9Z-hexadecenoate (16:1n7), 9Z-octadecenoate (18:1n9), 9Z,12Z-octadecadienoate (18:2n6), 8Z,11Z,14Z-eicosatrienoate (20:3n6), 5Z,8Z,11Z,14Z-eicosatetraenoate (20:4n6), 5Z,8Z,11Z,14Z,17Z-eicosapentaenoate (20:5n3), and 4Z,7Z,10Z,13Z,16Z,19Z-docosahexaenoate (22:6n3). The mixture of fatty acids at the hydroxyl group can be present at the ratios shown in Table 7.

Compositions for Use as Lipid Internal Standards

In one embodiment of the present disclosure, a composition is provided for use as an internal standard comprising one or more mixtures of lipid molecules representative of the composition of lipid molecular species present in one or more corresponding lipid classes in a sample of interest, each mixture of lipid molecules comprising one or more of: a lipid backbone having a mixture of at least two different isotopically-labeled fatty acids at a single position on the lipid backbone, wherein the lipid backbone is for a lipid class having at least one acyl group; an isotopically-labeled lipid backbone having a mixture of at least two different fatty acids at a single position on the lipid backbone, wherein the lipid backbone is for a lipid class having at least one acyl group; or a lipid backbone having a single isotopically-labeled fatty acid at a first position on the lipid backbone and having a mixture of at least two different fatty acids at a separate position on the lipid backbone, wherein the lipid backbone is for a lipid class having at least two fatty acids, wherein the mixture of the at least two fatty acids is representative of the fatty acids that occur in the corresponding lipid class in the sample of interest, and wherein each of the fatty acids in the mixture is present at a ratio representative of the ratio of occurrence of the fatty acids in the lipid molecular species present in the corresponding lipid class in the sample of interest. The lipid class can include one or more of triacylglycerols, diacylglycerols, 1-monoacylglycerol, phospholipids, phosphatidylcholine, o-phosphatidylcholine, phosphatidyletanolamine, p-phosphatidylethanolamine, cholesteryl esters, lysophosphatidylcholine, lysophosphatidylethanolamine, lysophosphatidylserine, lysophosphatidylinositol, lysophosphatidylglycerol, lysophosphatidic acid, lyso CDP-diacylglycerol, CDP-diacylglycerol, sphingomyelin, cardiolipin, phosphatidylserine, phosphatidylinositol, phosphatidylglycerol, phosphatidic acid, ceramide, lactosylceramide, glucosylceramide, phytoceramide, 6-hydroxyceramide, cerebroside, ganglioside, wax esters, or wax diesters. The one or more mixtures of fatty acids in each of the one or more mixtures of lipid molecules can include one or more of the mixtures of lipid molecular species listed in Table 1, Table 2, Table 3, Table 4, Table 5, Table 6, or Table 7. The one or more mixtures of fatty acids in each of the one or more mixtures of lipid molecules can consist of one or more of the mixtures of lipid molecular species listed in Table 1, Table 2, Table 3, Table 4, Table 5, Table 6, or Table 7.

In one embodiment of the present disclosure, a composition is provided for use as an internal standard comprising one or more mixtures of lipid molecules representative of the composition of lipid molecular species present in one or more corresponding lipid classes in a sample of interest, each mixture of lipid molecules comprising: a lipid backbone having an isotopically-labeled fatty acid at a first position on the lipid backbone, wherein the lipid backbone is for a lipid class having at least two acyl groups; and a mixture of at least two different fatty acids present at a separate position on the lipid backbone, wherein the mixture of fatty acids is representative of the fatty acids that occur in the lipid class in the sample of interest, and wherein each of the fatty acids in the mixture is present at a ratio representative of the ratio of occurrence of the fatty acid in the lipid molecular species present in the corresponding lipid class in the sample of interest. In the composition, the lipid class can include one or more of triacylglycerols, diacylglycerols, phospholipids, phosphatidylcholine, o-phosphatidylcholine, phosphatidylethanolamine, p-phosphatidylethanolamine, sphingomyelin, cardiolipin, phosphatidylserine, phosphatidylinositol, phosphatidylglycerol, phosphatidic acid, CDP-diacylglycerol, ceramide, lactosylceramide, glucosylceramide, phytoceramide, 6-hydroxyceramide, cerebroside, ganglioside, or wax diesters. The one or more mixtures of fatty acids in each of the one or more mixtures of lipid molecules can include of one or more of the mixtures of lipid molecular species listed in Table 1, Table 2, Table 3, Table 4, Table 5, or Table 6. The one or more mixtures of fatty acids in each of the one or more mixtures of lipid molecules can consist of one or more of the mixtures of lipid molecular species listed in Table 1, Table 2, Table 3, Table 4, Table 5, or Table 6.

In one embodiment of the present disclosure, a composition is provided for use as an internal standard comprising one or more mixtures of lipid molecules representative of the composition of lipid molecular species present in one or more corresponding lipid classes in a sample of interest, each mixture of lipid molecules comprising: a lipid backbone having one or more isotopic labels, wherein the lipid backbone is for a lipid class having at least one acyl group; and a mixture of at least two different fatty acids present at a single position on the lipid backbone, wherein the mixture of fatty acids is representative of the fatty acids that occur in the lipid class in the sample of interest, and wherein each of the fatty acids in the mixture is present at a ratio representative of the ratio of occurrence of the fatty acids in the lipid molecular species present in the corresponding lipid class in the sample of interest. In the composition, the lipid class can include one or more of triacylglycerols, diacylglycerols, 1-monoacylglycerol, phospholipids, phosphatidylcholine, o-phosphatidylcholine, phosphatidylethanolamine, p-phosphatidylethanolamine, cholesteryl esters, lysophosphatidylcholine, lysophosphatidylethanolamine, lysophosphatidylserine, lysophosphatidylinositol, lysophosphatidylglycerol, lysophosphatidic acid, lyso CDP-diacylglycerol, CDP-diacylglycerol, sphingomyelin, cardiolipin, phosphatidylserine, phosphatidylinositol, phosphatidylglycerol, phosphatidic acid, ceramide, lactosylceramide, glucosylceramide, phytoceramide, 6-hydroxyceramide, cerebroside, ganglioside, wax esters, or wax diesters. The one or more mixtures of fatty acids in each of the one or more mixtures of lipid molecules can include of one or more of the mixtures of lipid molecular species listed in Table 1, Table 2, Table 3, Table 4, Table 5, Table 6, or Table 7. The one or more mixtures of fatty acids in each of the one or more mixtures of lipid molecules can consist of one or more of the mixtures of lipid molecular species listed in Table 1, Table 2, Table 3, Table 4, Table 5, Table 6, or Table 7.

In the compositions provided above, the sample of interest can be a complex mixture comprised of lipid molecules, a biological sample such as a plant sample or an animal sample. The animal sample may be from a mammal such as, for example, a human, a mouse, a non-human primate, a rabbit or other mammal, or a non-mammal such as, for example, a zebra fish sample. The biological sample of interest can include blood, plasma, serum, isolated lipoprotein fraction, saliva, urine, lymph fluid, and cerebrospinal fluid, a tissue sample, a cellular sample, or a skin sample.

In the compositions provided above, the isotopic label can include any isotopic label including $^2$H, $^{13}$C, or $^{15}$N.

In the compositions provided above, the fatty acid can be a saturated fatty acid.

In the compositions provided above, the first position on the lipid backbone can be a sn-1 position. The first position on the lipid backbone can be a sn-1 position and the separate position on the lipid backbone can be a sn-2 or a sn-3 position. In an alternate embodiment, the first position on the lipid backbone can be a sn-2 position. The first position can be a sn-2 and the separate position can be a sn-1 or sn-3 position. In another embodiment, the first position on the lipid backbone can be a sn-3 position. The first position can be a sn-3 position and the separate position can be a sn-1 or sn-2 position.

In the compositions provided above, one of the lipid classes can consist of phosphatidylcholines or o-phosphatidylcholines, wherein the first position can be a sn-1 position and the separate position can be a sn-2 position, or the first position can be a sn-2 position and the separate position can be a sn-1 position, wherein a deuterium-labeled hexadecanoyl-d9 (16:0-d9) can be present at the first position, and wherein the mixture of fatty acids at the separate position can comprise 9Z-hexadecenoyl (16:1n7), 9Z-octadecenoyl (18:1n9), 9Z,12Z-octadecadienoyl (18:2n6), 9Z,12Z,15Z-octadecatrienoyl (18:3n3), 8Z,11Z,14Z-eicosatrienoyl (20:3n6), 5Z,8Z,11Z,14Z-eicosatetraenoyl (20:4n6), 5Z,8Z,11Z,14Z,17Z-eicosapentaenoyl (20:5n3), 7Z,10Z,13Z,16Z-docosatetraenoyl (22:4n6), 7Z,10Z,13Z,16Z,19Z-docosapentaenoyl (22:5n3), and 4Z,7Z,10Z,13Z,16Z,19Z-docosahexaenoyl (22:6n3). The mixture of fatty acids at the separate position can be present at the ratios shown in Table 2.

In the compositions provided above, one of the lipid classes can consist of phosphatidylethanolamines and p-phosphatidylethanolamines, wherein the first position can be a sn-1 position and the separate position can be a sn-2 position, or the first position can be a sn-2 position and the separate position can be a sn-1 position, wherein a deuterium-labeled octadecanoyl-d9 (18:0-d9) can be present at the first position, and wherein the mixture of fatty acids at the separate position can comprise 9Z-octadecenoyl (18:1n9), 9Z,12Z-octadecadienoyl (18:2n6), 9Z,12Z,15Z-octadecatrienoyl (18:3n3), 8Z,11Z,14Z-eicosatrienoyl (20:3n6), 5Z,8Z,11Z,14Z-eicosatetraenoyl (20:4n6), 5Z,8Z,11Z,14Z,17Z-eicosapentaenoyl (20:5n3), 7Z,10Z,13Z,16Z,19Z-docosapentaenoyl (22:5n3), and 4Z,7Z,10Z,13Z,16Z,19Z-docosahexaenoyl (22:6n3). The mixture of fatty acids at the separate position can be present at the ratios shown in Table 3.

In the compositions provided above, one of the lipid classes can consist of sphingomyelins, wherein deuterium-labeled sphingosine can be present at the first position, and wherein the mixture of fatty acids at the separate position can comprise hexadecanoyl (16:0), 9Z-octadecenoyl (18:1n9), tetracosanoyl (24:0), and 15Z-tetracosenoyl (24:1n9). The mixture of fatty acids at the separate position can be present at the ratios shown in Table 4.

In the compositions provided above, one of the lipid classes can consist of diacylglycerols, wherein the first position can be a sn-1 position and the separate position can be a sn-2 position, or the first position can be a sn-2 position and the separate position can be a sn-1 position, wherein deuterium-labeled palmitate (16:0-d9) can be present at the first position, and wherein the mixture of fatty acids at the separate position can comprise hexadecanoyl (16:0), octadecanoyl (18:0), 9Z-octadecenoyl (18:1n9), 9Z,12Z-octadecadienoyl (18:2n6), 9Z,12Z,15Z-octadecatrienoyl (18:3n3), 5Z,8Z,11Z,14Z-eicosatetraenoyl (20:4n6), 5Z,8Z,11Z,14Z,17Z-eicosapentaenoyl (20:5n3), and 4Z,7Z,10Z,13Z,16Z,19Z-docosahexaenoyl (22:6n3). The mixture of fatty acids at the separate position can be present at the ratios shown in Table 6.

In the compositions provided above, one of the lipid classes can consist of triacylglycerols, wherein the first position can be a sn-1 position and the separate position can be a sn-2 or sn-3 position, or the first position can be a sn-2 position and the separate position can be a sn-1 or sn-3 position, or the first position can be a sn-3 position and the separate position can be a sn-1 or sn-2 position, wherein deuterium-labeled palmitate (16:0-d9) can be present at the first position, wherein oleate (18:1n9) can be present at a sn-2 position, and wherein the mixture of fatty acids at the separate position can comprise hexadecanoyl (16:0), octadecanoyl (18:0), 9Z-octadecenoyl (18:1n9), 9Z,12Z-octadecadienoyl (18:2n6), 9Z,12Z,15Z-octadecatrienoyl (18:3n3), 8Z,11Z,14Z-eicosatrienoyl (20:3n6), 5Z,8Z,11Z,14Z-eicosatetraenoyl (20:4n6), and 4Z,7Z,10Z,13Z,16Z,19Z-docosahexaenoyl (22:6n3). The mixture of fatty acids at the separate position can be present at the ratios shown in Table 5.

In the compositions provided above, one of the lipid classes can consist of cholesteryl esters, wherein the single position can be a hydroxyl group, and wherein the mixture of fatty acids attached to the hydroxyl group can comprise hexadecanoate (16:0), 9Z-hexadecenoate (16:1n7), 9Z-octadecenoate (18:1n9), 9Z,12Z-octadecadienoate (18:2n6), 8Z,11Z,14Z-eicosatrienoate (20:3n6), 5Z,8Z,11Z,14Z-eicosatetraenoate (20:4n6), 5Z,8Z,11Z,14Z,17Z-eicosapentaenoate (20:5n3), and 4Z,7Z,10Z,13Z,16Z,19Z-docosahexaenoate (22:6n3). The mixture of fatty acids at the hydroxyl group can be present at the ratios shown in Table 7.

Methods for Detection and Quantification of Lipid Molecules in Samples of Interest In one embodiment of the present disclosure, a method is provided for one of detecting and quantifying lipid molecules present in a sample of interest, the method comprising: i) adding to a sample of interest a known amount of a composition having one or more mixtures of lipid molecules representative of the composition of lipid molecular species present in one or more corresponding lipid classes in the sample of interest, the composition comprising one or more of: a) a lipid backbone having a mixture of at least two different isotopically-labeled fatty acids at a single position on the lipid backbone, wherein the lipid backbone is for a lipid class having at least one acyl group; b) an isotopically-labeled lipid backbone having a mixture of at least two different fatty acids at a single position on the lipid backbone, wherein the lipid backbone is for a lipid class having at least one acyl group; or c) a lipid backbone having a single isotopically-labeled fatty acid at a first position on the lipid backbone and having a mixture of at least two different fatty acids at a separate position on the lipid backbone, wherein the lipid backbone is for a lipid class having at least two fatty acids, wherein the mixture of the at least two fatty acids is representative of the fatty acids that occur in the corresponding lipid class in the sample of interest, and wherein each of the fatty acids in the mixture is present at a ratio representative of the ratio of occurrence of the fatty acids in the lipid molecular species present in the corresponding lipid class in the sample of interest; and ii) one of detecting and quantifying the lipid molecular species present in each of the one or more corresponding lipid classes in the sample of interest by using the composition having the one or more representative mixtures of lipid molecules as an internal standard.

In one embodiment of the present disclosure, a method is provided for one of detecting and quantifying lipid molecules present in a sample of interest, comprising: adding to a sample of interest a known amount of a composition having one or more mixtures of lipid molecules representative of the composition of lipid molecular species present in one or more corresponding lipid classes in the sample of interest, wherein each mixture of lipid molecules comprises i) a lipid backbone having an isotopically-labeled fatty acid at a first position on the lipid backbone, wherein the lipid backbone is for a lipid class having at least two acyl groups; and ii) a mixture of at least two different fatty acids present at a separate position on the lipid backbone, wherein the mixture of fatty acids is representative of the fatty acids that occur in the corresponding lipid class in the sample of interest, and wherein each of the fatty acids in the mixture is present at a ratio representative of the ratio of occurrence of the fatty acid in the lipid molecular species present in the corresponding lipid class in the sample of interest; and one of detecting and quantifying the lipid molecular species present in the corresponding lipid class in the sample of interest by using the representative mixture of lipid molecules as an internal standard.

In one embodiment of the present disclosure, a method is provided for one of detecting and quantifying lipid molecules present in a sample of interest, comprising: adding to a sample of interest a known amount of a composition having one or more mixtures of lipid molecules representative of the composition of lipid molecular species present in one or more corresponding lipid classes in the sample of interest, wherein each mixture of lipid molecules comprises i) a lipid backbone having one or more isotopic labels, wherein the lipid backbone is for a lipid class having at least one acyl group; and ii) a mixture of at least two different fatty acids present at a single position on the lipid backbone, wherein the mixture of fatty acids is representative of the fatty acids that occur in the corresponding lipid class in the sample of interest, and wherein each of the fatty acids in the mixture is present at a ratio representative of the ratio of occurrence of the fatty acids in the lipid molecular species present in the corresponding lipid class in the sample of interest; and one of detecting and quantifying the lipid molecular species present in the corresponding lipid class in the sample of interest by using the representative mixture of lipid molecules as an internal standard.

The method of detecting and/or quantifying the lipid molecular species present in the sample of interest can include one or a combination of mass spectrometry (MS), high performance liquid chromatography (HPLC), isocratic HPLC, gradient HPLC, normal phase chromatography, reverse phase HPLC, size exclusion chromatography, ion exchange chromatography, capillary electrophoresis, microfluidics, chromatography, gas chromatography (GC), thin-layer chromatography (TLC), and combinations thereof. The method for detecting and/or quantifying the lipid molecular species present in the biological sample can include the use of mass spectrometry (MS).

In the method of detecting and/or quantifying the lipid molecular species present in the sample of interest, the sample of interest can be a complex mixture comprised of lipid molecules, a biological sample such as a plant sample or an animal sample. The animal sample may be from a mammal such as, for example, a human, a mouse, a non-human primate, a rabbit or other mammal, or a non-mammal such as, for example, a zebra fish sample. The biological sample of interest can include blood, plasma, serum, isolated lipoprotein fraction, saliva, urine, lymph fluid, and cerebrospinal fluid, a tissue sample, a cellular sample, or a skin sample.

In the method of detecting and/or quantifying the lipid molecular species present in the sample of interest, the one or more mixtures of fatty acids in each of the one or more mixtures of lipid molecules can include one or more of the mixtures of lipid molecular species listed in Table 1, Table 2, Table 3, Table 4, Table 5, Table 6, or Table 7. The one or more mixtures of fatty acids in each of the one or more mixtures of lipid molecules can consist of one or more of the mixtures of lipid molecular species listed in Table 1, Table 2, Table 3, Table 4, Table 5, Table 6, or Table 7.

Kit

Generally, the kits of the present disclosure include one or more internal standards and instructions for using the internal standards to detect and/or quantify lipids in the sample of interest. The kit may further include one or more control samples and sample collection receptacles. The internal standard compositions within a kit can be packaged together in various combinations of one or more lipid classes or can be packaged in separate vials or containers. A kit may include labels and/or packaging inserts setting out instructions for preparation and use, specimen collection receptacles, a transportation container, and/or a mailer for shipping. Additional kit components in separate packaging could include buffers and other reagents for the detection and/or quantification of lipids in a sample of interest.

The kit can comprise one or more internal standard mixtures. In one embodiment, the kit can contain an internal standard mixture comprising isotopically labeled fatty acids wherein at least one isotopically labeled fatty acid is present from each lipid class in the sample of interest. In one embodiment, the kit may contain a set of internal standards comprising the lipid classes and isotopically labeled fatty acids presented in Table 1. In a further embodiment, the isotopically labeled fatty acids in the set of internal standards are present at the ratios given in Table 1.

The kit may further comprise a volumetric container. The volumetric container may be any container (i.e., a cup, vial, microfuge tube, microtiter plate etc.) suitable for holding a liquid sample. The volumetric container may optionally contain volumetric measurements which may be useful in measuring out a desirable amount of the sample or other reagents. The volumetric container may be made of any material (e.g., plastics, aluminum, stainless steel). The internal volume of the volumetric container depends on the type of sample to be collected. The volumetric container can include a body and a cap. In some embodiments, the internal standard material may be attached to the cap. In some embodiments, the internal standard material may be coated on the internal volume of the body of the volumetric container.

In some embodiments, the volumetric container may additionally be configured for the type of sample collection contemplated and used for collection of the specimen. In other aspects, a specimen collection receptacle is separately provided in the kit, and may be in the form of a cup, vial, microfuge tube.

The kit may optionally comprise a transportation container. The transportation container may be any structure suitable for transportation of samples. The container is configured such that the sample material can be packed into the container and the container may be sealed.

The kit may optionally include an extraction solution.

In one embodiment of the present disclosure, a kit is provided comprising: i) one or more mixtures of lipid molecules for use as an internal standard, wherein each of the one or more mixtures of lipid molecules is representative of the composition of lipid molecular species present in one or more corresponding lipid classes in a sample of interest, each mixture of lipid molecules comprising one or more of: a lipid backbone having a mixture of at least two different isotopically-labeled fatty acids at a single position on the lipid backbone, wherein the lipid backbone is for a lipid class having at least one acyl group; an isotopically-labeled lipid backbone having a mixture of at least two different fatty acids at a single position on the lipid backbone, wherein the lipid backbone is for a lipid class having at least one acyl group; or a lipid backbone having a single isotopically-labeled fatty acid at a first position on the lipid backbone and having a mixture of at least two different fatty acids at a separate position on the lipid backbone, wherein the lipid backbone is for a lipid class having at least two acyl groups, wherein the mixture of at least two different fatty acids is representative of the fatty acids that occur in the corresponding lipid class in the sample of interest, and wherein each of the fatty acids in the mixture is present at a ratio representative of the ratio of occurrence of the fatty acids in the lipid molecular species present in the corresponding lipid class in the sample of interest; and ii) instructions for using the one or more mixtures of lipid molecules as the internal standard for one of detecting and quantifying the lipid molecular species present in the lipid class in the sample of interest. The lipid class can include one or more of triacylglycerols, diacylglycerols, 1-monoacylglycerol, phospholipids, phosphatidylcholine, o-phosphatidylcholine, phosphatidyletanolamine, p-phosphatidylethanolamine, cholesteryl esters, lysophosphatidylcholine, lysophosphatidylethanolamine, lysophosphatidylserine, lysophosphatidylinositol, lysophosphatidylglycerol, lysophosphatidic acid, lyso CDP-diacylglycerol, CDP-diacylglycerol, sphingomyelin, cardiolipin, phosphatidylserine, phosphatidylinositol, phosphatidylglycerol, phosphatidic acid, ceramide, lactosylceramide, glucosylceramide, phytoceramide, 6-hydroxyceramide, cerebroside, ganglioside, wax esters, or wax diesters.

In one embodiment of the present disclosure, a kit is provided comprising: i) one or more mixtures of lipid molecules for use as an internal standard, wherein each of the one or more mixtures of lipid molecules is representative of the composition of lipid molecular species present in each of one or more corresponding lipid classes in a sample of interest, each mixture of lipid molecules comprising: a lipid backbone having an isotopically-labeled fatty acid at a first position on the lipid backbone and a mixture of at least two different fatty acids present at a separate position on the lipid backbone, wherein the lipid backbone is for a lipid class having at least two acyl groups, or a lipid backbone having one or more isotopic labels and a mixture of at least two different fatty acids present at a single position on the lipid backbone, wherein the lipid backbone is for a lipid class having at least one acyl group, wherein the mixture of fatty acids is representative of the fatty acids that occur in the lipid class in the sample of interest, and wherein each of the fatty acids in the mixture is present at a ratio representative of the ratio of occurrence of the fatty acids in the lipid molecular species present in the corresponding lipid class in the sample of interest; and ii) instructions for using the one or more mixtures of lipid molecules as the internal standard for one of detecting and quantifying the lipid molecular species present in the corresponding lipid class in the sample of interest. The lipid class having at least two acyl groups can include one or more of triacylglycerols, diacylglycerols, phospholipids, phosphatidylcholine, o-phosphatidylcholine, phosphatidyletanolamine, p-phosphatidylethanolamine, sphingomyelin, cardiolipin, phosphatidylserine, phosphatidylinositol, phosphatidylglycerol, phosphatidic acid, CDP-diacylglycerol, ceramide, lactosylceramide, glucosylceramide, phytoceramide, 6-hydroxyceramide, cerebroside, ganglioside, or wax diesters. The lipid class having at least one acyl group can include one or more of triacylglycerols, diacylglycerols, phospholipids, phosphatidylcholine, o-phosphatidylcholine, phosphatidylethanolamine, p-phosphatidylethanolamine, sphingomyelin, cardiolipin, phosphatidylserine, phosphatidylinositol, phosphatidylglycerol, phosphatidic acid, CDP-diacylglycerol, ceramide, lactosylceramide, glucosylceramide, phytoceramide, 6-hydroxyceramide, cerebroside, ganglioside, wax diesters cholesteryl esters, lysophosphatidylcholine, lysophosphatidylethanolamine, lysophosphatidylserine, lysophosphatidylinositol, lysophosphatidylglycerol, lysophosphatidic acid, lyso CDP-diacylglycerol, wax esters, 1-monoacylglycerol.

The kits can include two or more of the mixtures of the lipid molecules representative of the composition of lipid molecular species present in two or more of the corresponding lipid classes in the sample of interest. The two or more mixtures of the lipid molecules can be packaged as a single component. The two or more mixtures of the lipid molecules can be packaged as separate components.

The kits may further include reagents for the detecting and quantifying.

The kits may further include a control sample having a known concentration of the composition of the lipid molecular species.

The kits may further include a mixture of free fatty acids for use as an internal standard that is representative of the composition of free fatty acids in the sample of interest. The free fatty acids for use in the kit may comprise the free fatty acids shown in Table 8.

In the kits, the sample of interest can be a complex mixture comprised of lipid molecules, a biological sample such as a plant sample or an animal sample. The animal sample may be from a mammal such as, for example, a human, a mouse, a non-human primate, a rabbit or other mammal, or a non-mammal such as, for example, a zebra fish sample. The biological sample of interest can include blood, plasma, serum, isolated lipoprotein fraction, saliva, urine, lymph fluid, and cerebrospinal fluid, a tissue sample, a cellular sample, or a skin sample.

In the kits, the fatty acid can be a saturated fatty acid.

In the kits, the isotopic label can include $^2$H, $^{13}$C, or $^{15}$N.

In the kits, the mixtures of fatty acids in each of the one or more mixtures of lipid molecules can include the mixtures of lipid molecular species listed in one or more of Table 1, Table 2, Table 3, Table 4, Table 5, Table 6, Table 7, or Table 8. In the kits, the mixtures of fatty acids in each of the one or more mixtures of lipid molecules can consist of one or more of the mixtures of lipid molecular species listed in one or more of Table 1, Table 2, Table 3, Table 4, Table 5, Table 6, Table 7, or Table 8.

In the kit, the first position on the lipid backbone can be a sn-1 position. The first position on the lipid backbone can be a sn-1 position and the separate position on the lipid backbone can be a sn-2 or a sn-3 position.

In the kit, one of the lipid classes can consist of phosphatidylcholines or o-phosphatidylcholines, wherein the first position can be a sn-1 position and the separate position can be a sn-2 position, or the first position can be a sn-2 position and the separate position can be a sn-1 position, wherein a deuterium-labeled hexadecanoyl-d9 (16:0-d9) can be present at the first position, and wherein the mixture of fatty acid groups at the separate position can comprise 9Z-hexadecenoyl (16:1n7), 9Z-octadecenoyl (18:1n9), 9Z,12Z-octadecadienoyl (18:2n6), 9Z,12Z,15Z-octadecatrienoyl (18:3n3), 8Z,11Z,14Z-eicosatrienoyl (20:3n6), 5Z,8Z,11Z,14Z-eicosatetraenoyl (20:4n6), 5Z,8Z,11Z,14Z,17Z-eicosapentaenoyl (20:5n3), 7Z,10Z,13Z,16Z-docosatetraenoyl (22:4n6), 7Z,10Z,13Z,16Z,19Z-docosapentaenoyl (22:5n3), and 4Z,7Z,10Z,13Z,16Z,19Z-docosahexaenoyl (22:6n3). The mixture of fatty acid groups at the separate position can be present at the ratios shown in Table 2.

In the kit, one of the lipid classes can consist of phosphatidylethanolamines and p-phosphatidylethanolamines, wherein the first position can be a sn-1 position and the separate position can be a sn-2 position, or the first position can be a sn-2 position and the separate position can be a sn-1 position, wherein a deuterium-labeled octadecanoyl-d9 (18:0-d9) can be present at the first position, and wherein the mixture of fatty acid groups at the separate position can comprise 9Z-octadecenoyl (18:1n9), 9Z,12Z-octadecadienoyl (18:2n6), 9Z,12Z,15Z-octadecatrienoyl (18:3n3), 8Z,11Z,14Z-eicosatrienoyl (20:3n6), 5Z,8Z,11Z,14Z-eicosatetraenoyl (20:4n6), 5Z,8Z,11Z,14Z,17Z-eicosapentaenoyl (20:5n3), 7Z,10Z,13Z,16Z,19Z-docosapentaenoyl (22:5n3), and 4Z,7Z,10Z,13Z,16Z,19Z-docosahexaenoyl (22:6n3). The mixture of fatty acid groups at the separate position can be present at the ratios shown in Table 3.

In the kit, one of the lipid classes can consist of sphingomyelins, wherein deuterium-labeled sphingosine can be present at the first position, and wherein the mixture of fatty acids at the separate position can comprise hexadecanoyl (16:0), 9Z-octadecenoyl (18:1n9), tetracosanoyl (24:0), and 15Z-tetracosenoyl (24:1n9). The mixture of fatty acid groups at the separate position can be present at the ratios shown in Table 4.

In the kit, one of the lipid classes can consist of diacylglycerols, wherein the first position can be a sn-1 position and the separate position can be a sn-2 position, or the first position can be a sn-2 position and the separate position can be a sn-1 position, wherein deuterium-labeled palmitate (16:0-d9) can be present at the first position, and wherein the mixture of fatty acid groups at the separate position can comprise hexadecanoyl (16:0), octadecanoyl (18:0), 9Z-octadecenoyl (18:1n9), 9Z,12Z-octadecadienoyl (18:2n6), 9Z,12Z,15Z-octadecatrienoyl (18:3n3), 5Z,8Z,11Z,14Z-eicosatetraenoyl (20:4n6), 5Z,8Z,11Z,14Z,17Z-eicosapentaenoyl (20:5n3), and 4Z,7Z,10Z,13Z,16Z,19Z-docosahexaenoyl (22:6n3). The mixture of fatty acid groups at the separate position can be present at the ratios shown in Table 6.

In the kit, one of the lipid classes can consist of triacylglycerols, wherein the first position can be a sn-1 position and the separate position can be a sn-2 or sn-3 position, or the first position can be a sn-2 position and the separate position can be a sn-1 or sn-3 position, or the first position can be a sn-3 position and the separate position can be a sn-1 or sn-2 position, wherein deuterium-labeled palmitate (16:0-d9) can be present at the first position, wherein oleate (18:1n9) can be present at a one separate position, and wherein the mixture of fatty acid groups at another separate position can comprise hexadecanoyl (16:0), octadecanoyl (18:0), 9Z-octadecenoyl (18:1n9), 9Z,12Z-octadecadienoyl (18:2n6), 9Z,12Z,15Z-octadecatrienoyl (18:3n3), 8Z,11Z,14Z-eicosatrienoyl (20:3n6), 5Z,8Z,11Z,14Z-eicosatetraenoyl (20:4n6), and 4Z,7Z,10Z,13Z,16Z,19Z-docosahexaenoyl (22:6n3). The mixture of fatty acid groups at the separate position can be present at the ratios shown in Table 5.

In the kit, one of the lipid classes can comprise cholesteryl esters, lysophosphatidylcholine, lysophosphatidylethanolamine, lysophosphatidylserine, lysophosphatidylinositol, lysophosphatidylglycerol, lysophosphatidic acid, lyso CDP-diacylglycerol, wax esters, or 1-monoacylglycerol.

In the kit, one of the lipid classes can consist of cholesteryl esters, wherein the single position is a hydroxyl group, and wherein the mixture of acyl groups attached to the hydroxyl group comprises hexadecanoate (16:0), 9Z-hexadecenoate (16:1n7), 9Z-octadecenoate (18:1n9), 9Z,12Z-octadecadienoate (18:2n6), 8Z,11Z,14Z-eicosatrienoate (20:3n6), 5Z,8Z,11Z,14Z-eicosatetraenoate (20:4n6), 5Z,8Z,11Z,14Z,17Z-eicosapentaenoate (20:5n3), and 4Z,7Z,10Z,13Z,16Z,19Z-docosahexaenoate (22:6n3). The mixture of acyl groups at the hydroxyl group can be present at the ratios shown in Table 7.

Methods of Measurement of Lipid Molecules

Assays for lipid metabolite or lipid molecule content may be performed on any sample type including, for example, a body fluid sample (e.g., blood, blood plasma, urine, cerebral spinal fluid (CSF)), a tissue sample, a cellular sample, a skin sample, a solution, a complex mixture, in vitro cultured cells, and cell culture media. In some embodiments, the amounts of the lipid molecules are determined from sample(s) selected from the group consisting of complex mixtures of lipids, blood, plasma, serum, isolated lipoprotein fraction, saliva, urine, lymph fluid, and cerebrospinal fluid. In some embodiments, the assays may be performed on whole blood, plasma, serum, or isolated lipoprotein fractions. In some embodiments, the sample(s) are plasma or serum.

In some embodiments, multiple different lipid molecules are measured in the same sample. In other embodiments, each of multiple lipid molecules is measured from a different sample. If multiple samples are used, the samples may be from the same or different body fluids of the subject.

The lipid molecules and other biomarkers may readily be isolated and/or quantified by methods known to those of skill in the art, including, but not limited to, methods utilizing: mass spectrometry (MS), high performance liquid chromatography (HPLC), isocratic HPLC, gradient HPLC, normal phase chromatography, reverse phase HPLC, size exclusion chromatography, ion exchange chromatography, capillary electrophoresis, microfluidics, chromatography, gas chromatography (GC), thin-layer chromatography (TLC), immobilized metal ion affinity chromatography (IMAC), affinity chromatography, immunoassays, and/or colorimetric assays. In some embodiments, the methods of the invention utilize MS to determine lipid molecule content.

For fatty acid methyl ester (FAME) analysis, lipids were extracted by the method of Folch et al. (*J Biol Chem* 226:497-509) using chloroform:methanol (2:1 v/v). Neutral lipids were separated from polar lipids by solid phase chromatography. The polar lipid fraction was separated into individual lipid classes using the Agilent Technologies 1100 Series LC, and the lipid class fractions were collected for fatty acid analysis. Neutral lipids were separated into individual lipid classes by thin-layer chromatography using a solvent system consisting of petroleum ether/diethyl ether/acetic acid (80:20:1), and the lipid class fractions were collected for fatty acid analysis. Each lipid class was trans-esterified in 1% sulfuric acid in methanol in a sealed vial under a nitrogen atmosphere at 100° C. for 45 minutes. The resulting fatty acid methyl esters were extracted from the mixture with hexane containing 0.05% butylated hydroxytoluene and prepared for GC analysis by sealing the hexane extracts under nitrogen. Fatty acid methyl esters were separated and quantified by capillary GC (Agilent Technologies 6890 Series GC) equipped with a 30 m DB 88 capillary column (Agilent Technologies) and a flame ionization detector.

Various analytical methods are well known to those of skill in the art, and are further described in the following documents, which are herein incorporated by reference in their entirety: MS: Cyr D, et al. A GCIMS validated method for the nanomolar range determination of succinylacetone in amniotic fluid and plasma: an analytical tool for tyrosinemia type I. J Chromatogr B Analyt Techno) Biomed Life Sci. 2006 Feb. 17; 832(1):24-9; Vogeser M. Abstract Liquid chromatography-tandem mass spectrometry—application in the clinical laboratory. Clin Chern Lab Med. 2003 February; 41(2):117-26. HPLC: Khalil P N, et al. Validation and application of a high-performance liquid chromatographic-based assay for determination of the inosine 5'-monophosphate dehydrogenase activity in erythrocytes. J Chromatogr B Analyt Techno) Biomed Life Sci. 2006 May 23; Fouassier M, et al. Determination of serotonin release from platelets by HPLC and ELISA in the diagnosis of heparin-induced thrombocytopenia: comparison with reference method by [C)-serotonin release assay; J Thromb Haemost. 2006 May; 4(5): 1136-9; Badiou S, et al. Determination of plasma amino acids by fluorescent derivatization and reversed-phase liquid chromatographic separation. Clin Lab. 2004; 50(3-4): 153-8; Brunelli T, et al. Comparison of three methods for total homocysteine plasma determination. Clin Lab. 200 I; 47(7-8):393-7. CE: Zinellu A, et al. Assay for the simultaneous determination of guanidinoacetic acid, creatinine and creatine in plasma and urine by capillary electrophoresis UV-detection. J Sep Sci. 2006 March; 29(5):704-8; Jabeen R, et al. Capillary electrophoresis and the clinical laboratory. Electrophoresis. 2006 May 23; Gao P, et al. Rapid detection of *Staphylococcus aureus* by a combination of monoclonal antibody-coated latex and capillary electrophoresis. Electrophoresis. 2006 May; 27(9):1784-9. Microfluidics: Johannessen E A, et al. A suspended membrane nanocalorimeter for ultralow volume bioanalysis. IEEE Trans Nanobioscience. 2002 March; 1(1):29-36; Herrmann M, et al. Enzymatically-generated fluorescent detection in micro-channels with internal magnetic mixing for the development of parallel microfluidic ELISA; Lab Chip. 2006 April; 6(4):555-60. Epub 2006 Mar. 3; Yang S, et al. Blood plasma separation in microfluidic channels using flow rate control. ASAIO J. 2005 September-October; 51 (5):585-90; Dupuy A M, et al. Protein biochip systems for the clinical laboratory; Clin Chern Lab Med. 2005; 43{12):1291-302. Chromatography: Paterson S, et al. Validation of techniques to detect illicit heroin use in patients prescribed pharmaceutical heroin for the management of opioid dependence. Addiction. 2005 December; 1 00(12): 1832-9; Bottcher M, et al. Evaluation of buprenorphine CEDIA assay versus GC-MS and ELISA using urine samples from patients in substitution treatment. J Anal Toxicol. 2005 November-December; 29(8):769-76; Julak J. Chromatographic analysis in bacteriologic diagnostics of blood cultures, exudates, and bronchoalveolar lavages. Prague Med Rep. 2005; 1 06(2): 175-94; Boettcher M, et al. Precision and comparability of Abuscreen OnLine assays for drugs of abuse screening in urine on Hitachi 917 with other immunochemical tests and with GC/MS. Clin Lab. 2000; 46(1-2):49-52. Immunoassays: Boettcher M, et al. Precision and comparability of Abuscreen OnLine assays for drugs of abuse screening in urine on Hitachi 917 with other immunochemical tests and with GC/MS. Clin Lab. 2000; 46(1-2):49-52; Westermann J, et al. Simple, rapid and sensitive determination of epinephrine and norepinephrine in urine and plasma by non-competitive enzyme immunoassay, compared with HPLC method. Clin Lab. 2002; 48(1-2):61-71; Aoyagi K, et al. Performance of a conventional enzyme immunoassay for hepatitis C virus core antigen in the early phases of hepatitis C infection. Clin Lab. 200 I; 47(3-4): 119-27; Hub I W, et al. A multi-center quality control study of different CA 15-3 immunoassays. Clin Lab. 2005; 51(11-12):641-5; Haller C A, et al. Comparison of an automated and point-of-care immunoassay to GC-MS for urine oxycodone testing in the clinical laboratory. J Anal Toxicol. 2006 March; 30(2): 106-11; Bayer M, et al. Evaluation of a new enzyme-linked immunosorbent assay for the determination of neopterin. Clin Lab. 2005; 51 (9-1 0):495-504; Groche D, et al. Standardization of two immunological HbA 1 c routine assays according to the new IFCC reference method. Clin Lab. 2003; 49(11-12):657-6 1; Ivan 0, et al; German KIMS Board. Applicability of recently established reference values for serum insulin-like growth factor I: A comparison of two assays—an (automated) chemiluminescence immunoassay and an enzyme-linked immunosorbent assay. Clin Lab. 2005; 51(7-8):381-7. Colormetric assays: Kramer K A, et al. Automated spectrophotometric analysis of mitochondrial respiratory chain complex enzyme activities in cultured skin fibroblasts. Clin Chern. 2005 November; 51(11):2110-6; Groche D, et al. Standardization of two immunological HbA 1 c routine assays according to the new IFCC reference method. Clin Lab. 2003; 49(11-12):657-61; WolfPL. History of diagnostic enzymology: A review of significant investigations. Clin Chim Acta. 2006 Mar. 24.

The TRUEMASS analytical platform may also be used for the methods of the invention. TRUEMASS is an analytical platform that may be used to get quantitative data from a sample on approximately 400 individual metabolites involved in structural and energetic lipid metabolism such as triglyceride, cholesterol ester and phospholipid metabolism. This platform is useful in profiling diseases as structural and energetic lipids are central components of metabolism and integrated into virtually every biological process in the body. A data set for a sample, for example a plasma, serum or other biological sample, comprises the quantitative measurement of free cholesterol and the following fatty acids from phosphatidylcholines, phosphatidylethanolamines, lyso-phosphatidylcholines, triglycerides, diglycerides, free fatty acids, and cholesterol esters: 14:0, 15:0, 16:0, 18:0, 20:0, 22:0, 24:0, 14:1n5, 16:1n7, t16:1n7, 18:1n9, t18:1n9, 18:1n7, 18:2n6, t18:2n6, 18:3n6, 18:3n3, 18:4n3, 20:1n9, 20:2n6, 20:3n9, 20:3n6, 20:4n6, 20:3n3, 20:4n3, 20:5n3, 22:1 n9, 22:2n6, 22:4n6, 22:5n3, 22:6n3, 24:1n9, 24:6n3 and plasmalogen derivatives of 16:0, 18:0, 18:1n9 and 18:1n7. Methods for using TRUEMASS are known to those of skill in the art, and are also described in the following documents, which are herein incorporated by reference in their entirety: U.S. patent application Ser. No. 11/296,829 (filed Dec. 6, 2005); Mutch D M, et al. An integrative metabolism approach identifies stearoyl-CoA desaturase as a target for an arachidonate-enriched diet. FASEB J. 2005 April; 19(6):

599-601. Epub 2005 Jan. 24; Stone S J, et al. Lipopenia and skin barrier abnormalities in DGAT2-deficient mice. J Biol Chem. 2004 Mar. 19; 279(12):11767-76; Watkins S M, et al. Phosphatidylethanolamine-N-methyltransferase activity and dietary choline regulate liver-plasma lipid flux and essential fatty acid metabolism in mice. J Nutr. 2003 November; 133(11):3386-91; Watkins S M, et al. Lipid metabolome-wide effects of the PPARgamma agonist rosiglitazone. Lipid Res. 2002 November; 43(11):1809-17.

The following examples are offered by way of illustration and not by way of limitation.

EXAMPLES

Example 1. Synthetic Composition of Internal Standard Mixtures

In contrast to traditional lipidomic strategies which typically use only a single internal standard per broad lipid class (e.g., phospholipids), here, internal standards containing a mixture of fatty acids (up to 10 fatty acids per lipid class) were synthesized. The fatty acids in the internal standard mixture (IS mixture) were selected to represent the diversity of chemical structures (lipid molecular species) found in the lipid classes present in the sample type to be analyzed. The concentration of each fatty acid presented in Table 1 was measured for each lipid class, and all remaining fatty acids in the lipid class were assigned to the closest internal standard analogue and assigned that measured value; the total concentration for each lipid class was calculated by adding the values (measured and assigned) of all molecular species for that lipid class.

Internal standards for each of 10 lipid classes were synthesized according the composition of fatty acids shown in Table 1. The lipid classes for internal standards are shown in the first row of Table 1, and the fatty acid "R" groups are listed in column 1 of Table 1. In Table 1, "d" refers to the addition of a deuterium label. For example, 16:0-d9 refers to palmitate with 9 deuterium atoms added.

Example 2. Synthesis and Description of Internal Standards and Mixtures Thereof Exemplary phospholipid internal standards for phosphatidylcholine, o-phosphatidylcholine, phosphatidylethanolamine, and p-phosphatidylethanolamine were synthesized starting with a glycerol phosphate head group and acylating deuterium-labeled palmitate (16:0) in the sn-1 position; and acylating a mixture of unsaturated fatty acids in the sn-2 position. The labeling strategy for the phospholipids, phosphatidylcholine and phosphatidylethanolamine, is represented in FIG. 1.

For the exemplary internal standard components phosphatidylcholine and o-phosphatidylcholine, the composition of fatty acids at the sn-2 position (sn-2 fatty acids) are displayed in Table 2. The structures of phosphatidylcholine and sn-2 fatty acids comprising the mixture are shown in FIG. 2. The structure of phosphatidylcholine with deuterated palmitate (16:0) in the sn-1 position and a fatty acid residue, denoted by "R", in the sn-2 position is shown in FIG. 2A. The structure of phosphatidylcholine with deuterated palmitate (16:0) in the sn-1 position and oleate (18:1n9), as an exemplary fatty acid, in the sn-2 position is shown in FIG. 2B. The structures of ten fatty acids (16:1n7, 18:1n9, 18:2n6, 18:3n3, 20:3n6, 20:4n6, 20:5n3, 22:4n6, 22:5n3, 22:6n3) in the fatty acid mixture for acylating into the sn-2 position of phosphatidylcholine are shown in FIG. 2C.

Exemplary lysophosphatidylcholine internal standards were synthesized starting with the phospholipid head group and acylating deuterium-labeled palmitate (16:0). The structure is shown in FIG. 3.

For phosphatidylethanolamine and p-phosphatidylethanolamine internal standards, the composition of sn-2 fatty acids are listed in Table 3. The structures of phosphatidylethanolamine and sn-2 fatty acids comprising the mixture are shown in FIG. 4. The structure of phosphatidylethanolamine with deuterated stearate (18:0) in the sn-1 position and the fatty acid residue, denoted by "R", in the sn-2 position is shown in FIG. 4A. The structure of phosphatidylethanolamine with deuterated stearate (18:0) in the sn-1 position and oleate (18:1n9) as an exemplary fatty acid in the sn-2 position is shown in FIG. 4B. The structures of eight fatty acids (18:1n9, 18:2n6, 18:3n3, 20:3n6, 20:4n6, 20:5n3, 22:5n3, 22:6n3) in the fatty acid mix for acylating into the sn-2 position of phosphatidylethanolamine are shown in FIG. 4C.

Lysophosphatidylethanolamine internal standards were synthesized starting with the phospholipid head group and acylating deuterium-labeled stearate (18:0). The structure is shown in FIG. 5.

Sphingomyelin internal standards were synthesized starting with a phosphocholine head group, acylating a deuterium-labeled sphingosine to the sn-1 position, and acylating a mixture of fatty acids into the sn-2 position. The acylated mixture of fatty acids in the sn-2 position may comprise, for example, 16:0, 18:1n9, 24:0, and 24:1n9.

For the exemplary internal standard component, sphingomyelin, the composition of fatty acids are displayed in Table 4. The structures of sphingomyelin and sn-2 fatty acids comprising the mixture are shown in FIG. 6. The structure of sphingomyelin with deuterium-labeled sphingosine at the first position, and the fatty acid residue, denoted by "R", in the sn-2 position is shown in FIG. 6A. The structure of sphingomyelin with deuterium-labeled sphingosine at the first position, and palmitate (16:0), as an exemplary fatty acid, in the sn-2 position is shown in FIG. 6B. The structures of four fatty acids (16:0, 18:1n9, 24:0, 24:1n9) in the fatty acid mix for acylating into the sn-2 position of sphingomyelin are shown in FIG. 6C.

Triacylglycerol internal standards were synthesized starting with a diacylglycerol backbone, acylating deuterium-labeled palmitate (16:0) at the sn-1 position, acylating oleate (18:1n9) at the sn-2 position and acylating a mixture of fatty acids into the sn-3 position. The acylated mixture of fatty acids at the sn-3 position may comprise, for example, 16:0, 18:0, 18:1n9, 18:2n6, 18:3n3, 20:3n6, 20:4n6 and 22:6n3.

For the exemplary internal standard component, triacylglycerol, the composition of sn-3 fatty acids are listed in Table 5. The structures of triacylglycerol and sn-3 fatty acids comprising the mixture are shown in FIG. 7. The structure of triacylglycerol with deuterium-labeled palmitate (16:0) at the sn-1 position, oleate (18:1n9) at the sn-2 position, and the fatty acid "R" in the sn-3 position is shown in FIG. 7A. The structure of triacylglycerol with deuterium-labeled palmitate (16:0) at the sn-1 position, oleate (18:1n9) at the sn-2 position, and palmitate (16:0) as an exemplary fatty acid in the sn-3 position is shown in FIG. 7B. The structures of eight fatty acids (16:0, 18:0, 18:1n9, 18:2n6, 18:3n3, 20:3n6, 20:4n6, 22:6n3) in the fatty acid mix for labeling the sn-3 position of triacylglycerol are shown in FIG. 7C.

Exemplary diacylglycerol internal standards were synthesized starting with a glycerol backbone, acylating deuterium-labeled palmitate (16:0) at the sn-1 position, and acylating a mixture of fatty acids into the sn-2 position. The acylated mixture of fatty acids at the sn-2 position may comprise, for example, 16:0, 18:0, 18:1n9, 18:2n6, 18:3n3, 20:4n6, 20:5n3, and 22:6n3.

For example, for diacylglycerol, the composition of sn-2 fatty acids are listed in Table 6. The structures of diacylglycerol and sn-2 fatty acids comprising the mixture are shown in FIG. 8. The structure of diacylglycerol with deuterium-labeled palmitate (16:0) at the sn-1 position, and a fatty acid residue, denoted by "R", in the sn-2 position is shown in FIG. 8A. The structure of diacylglycerol with deuterium-labeled palmitate (16:0) at the sn-1 position, and palmitate (16:0), as an exemplary fatty acid, in the sn-2 position is shown in FIG. 8B. The structures of eight fatty acids (16:0, 18:0, 18:1n9, 18:2n6, 18:3n3, 20:4n6, 20:5n3, 22:6n3) in the fatty acid mix for labeling the sn-2 position of diacylglycerol are shown in FIG. 8C.

Exemplary cholesteryl ester internal standards were synthesized starting with a cholesterol backbone, adding deuterium labels in the n6 position, and acylating a mixture of fatty acids to the hydroxyl group. The acylated mixture of fatty acids acylated to the hydroxyl group may comprise, for example, 16:0, 16:1n7, 18:1n9, 18:2n6, 20:3n6, 20:4n6, 20:5n3, and 22:6n3.

For example, for cholesteryl ester, the composition of fatty acids is listed in Table 7. The structures of cholesteryl ester and fatty acids comprising the mixture are shown in FIG. 9. The structure of cholesteryl ester with deuterium labels at the n6 position, and the fatty acid "R" acylated to the hydroxyl group is shown in FIG. 9A. The structure of cholesteryl ester with deuterium labels at the n6 position, and linoleate (18:2n6), as the exemplary fatty acid, acylated to the hydroxyl group is shown in FIG. 9B. The structure of eight fatty acids (16:0, 16:1n7, 18:1n9, 18:2n6, 20:3n6, 20:4n6, 20:5n3, 22:6n3) in the fatty acid mix for use in acylating the hydroxyl group of cholesteryl ester are shown in FIG. 9C.

Free fatty acid internal standards were produced by synthesizing a 50:50 mixture consisting of 50% deuterium-labeled fatty acid and 50% single odd-chain fatty acid. The deuterium-labeled fatty acid may be, for example, palmitate (16:0), and the odd-chain fatty acid may be, for example, 17:1n7.

For example, for free fatty acids, the composition of fatty acids are listed in Table 8. The structures of the free fatty acids comprising the mixture are shown in FIG. 10. The structure of the free fatty acid palmitate (16:0) with deuterium labels is shown in FIG. 10A. The structure of the free fatty acid, 17:1n7, is shown in FIG. 10B.

Example 3. Validating and Assessing Performance of Lipid Internal Standard Mixtures Lipids were extracted from samples using a methanol:dichloromethane extraction procedure. Internal standards in dichloromethane:methanol (50:50) were added to the extract solution, followed by a series of centrifugation and bottom layer recovery steps. The combined bottom layer aliquots were concentrated under nitrogen and reconstituted in 0.25 mL of 10 mM ammonium acetate dichloromethane:methanol (50:50). The extracts were transferred to inserts and placed in vials for analysis using infusion-MS. Infusion-MS analysis is performed on a Shimazdu LC with nano PEEk tubing combined with the Sciex Selexlon and 5500 QTRAP. The samples were analyzed via both positive and negative mode electrospray. The 5500 QTRAP scan is performed in MRM mode with the total of +1100 MRMs including internal standards.

An exemplary internal standard mixture containing the components indicated in Table 9 was synthesized, and the synthetic internal standards mixture was evaluated to determine the concentrations and purity of the mixture. Labeled and unlabeled standard mixtures were reported to be 10.3 mgs/mL. Actual concentrations of the internal standards in the mixture were determined based on NMR and quantitative fatty acid analysis; results of these two analyses were within 2% of each other. Column 2 of Table 9 indicates the target concentration for each internal standard component of the mixture, and Columns 3 and 4 of Table 9 shows the actual concentration for each indicated component. Column 3 shows the concentration obtained for the labeled standards and Column 4 shows the concentration obtained for the unlabeled standards. A complete fatty acid analysis of the samples determined that the internal standard mixture was >99% pure.

TABLE 9

Composition of one exemplary internal standard mixture

| Component | Target Concentration | Actual Concentration (Labeled) | Actual Concentration (Unlabeled) |
|---|---|---|---|
| PCd16:0/16:1 | 5% | 5.7% | 5.7% |
| PCd16:0/18:1 | 20% | 17.9% | 18.1% |
| PCd16:0/18:2 | 20% | 20.9% | 20.0% |
| PCd16:0/18:3 | 5% | 5.7% | 6.0% |
| PCd16:0/20:3 | 5% | 4.6% | 4.5% |
| PCd16:0/20:4 | 20% | 19.7% | 19.2% |
| PCd16:0/20:5 | 5% | 5.2% | 4.3% |
| PCd16:0/22:4 | 5% | 4.1% | 4.9% |
| PCd16:0/22:5 | 5% | 5.3% | 5.6% |
| PCd16:0/22:6 | 10% | 11.0% | 11.7% |

The performance of the exemplary labeled and unlabeled internal standard mixtures was assessed to determine if the presence of the label caused a shift in chromatographic retention time. The labeled standards did not substantially shift retention time compared to unlabeled analogs.

The quantification performance of the labeled and unlabeled internal standard mixtures was assessed experimentally in a solution of unlabeled standards and in serum. Lipids were extracted from an unlabeled internal standard mixture sample and a serum sample, each in the presence of labeled internal standard mixture and PC17:0/17:0 (a traditional lipidomics internal standard). The samples were extracted five times to produce a total of ten samples (5 serum and 5 unlabeled standard mixture). The lipids extracted from the samples were analyzed using described methods. The concentration of each phosphatidylcholine species was calculated in nMoles per mL of starting material. Concentrations were calculated using both the internal standard mixture and the traditional internal standard PC17:0/17:0. In serum, the precision as determined by calculating the analytical CV was 20% and 11% for the traditional PC17:0/17:0 IS and the IS mixture respectively. In samples of the unlabeled internal standard mixture, the overall precision as determined by calculating the analytical CV was 11% and 3% for the traditional PC17:0/17:0 IS and the IS mixture respectively.

Figure 11:
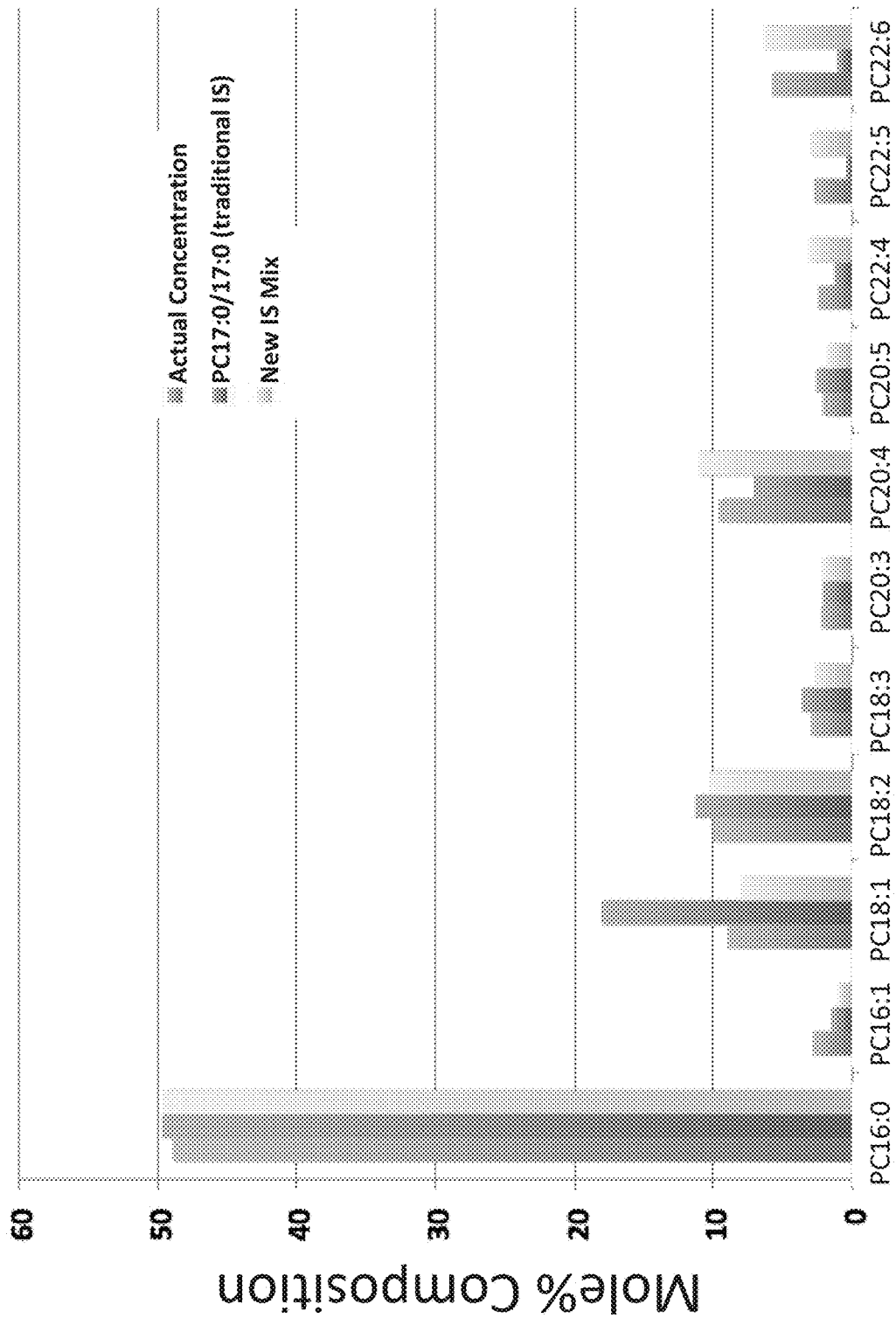
FIG. 11 is a graph showing the actual concentrations of the indicated phosphatidylcholine species in an unlabeled internal standard mix sample compared to the concentrations calculated using a traditional internal standard (IS) PC17:0/17:0 and an exemplary IS mix according to one or more embodiments of the present disclosure. Concentrations are displayed in mole % composition.

The Mole % composition for the fatty acids was calculated using the IS mixture and the traditional IS and compared to the actual concentration of the fatty acids in the sample. The calculated values obtained with the IS mixture were closer to the actual values than those values calculated using the traditional IS. The results are graphically presented in FIG. 11.

Example 4. Assessing Internal Standard Mixture in Human Samples

Figure 12:
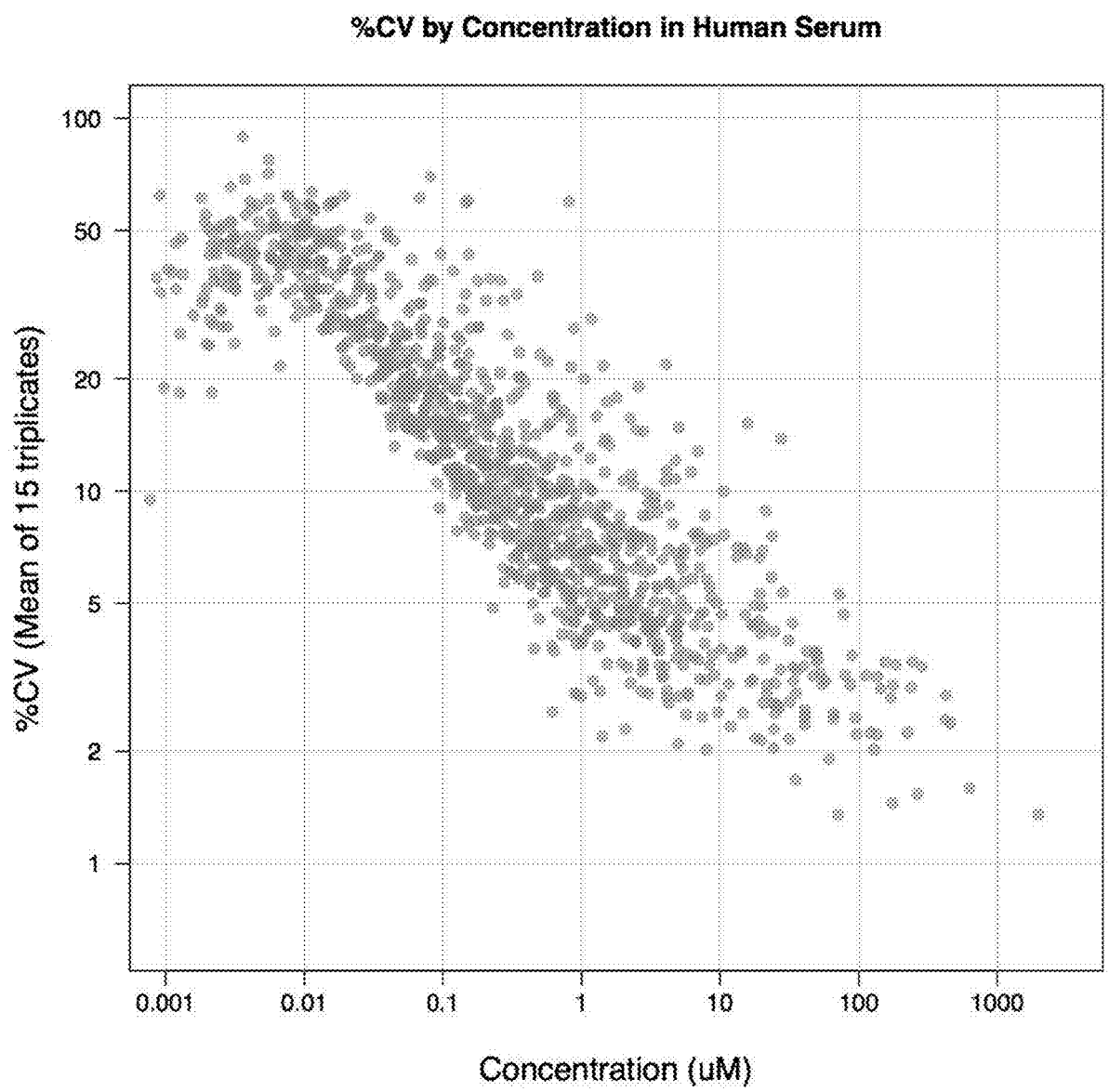
FIG. 12 is a graph showing the concentration calculated using the internal standard mixture and the precision of the calculations (in % CV) for 15 human serum samples according to one or more embodiments of the present disclosure.

To assess the quantification performance of the internal standard mixture, the lipid molecular species in 15 human serum samples, run in triplicate, were measured using the mixture of internal standards described in Table 1. Lipids were extracted from the serum samples in the presence of the labeled internal standard mixture and the lipid extracts were analyzed using the described methods. The mean concentration of each of the 1,100 measured lipid molecular species in the triplicate samples was calculated using the internal standard mixture, and the precision was determined by calculating the analytical CV. The average concentration and CV values for the 15 triplicate samples were plotted for all 1,100 measured lipid molecular species. The scatterplot showing the relationship of the % CV to the concentration of lipid molecular species is graphically presented in FIG. 12. The CV was lower for lipid molecular species at the highest concentrations, however CV as low as 10% was obtained for certain molecular species at very low concentrations (e.g., 0.001 uM).

Figure 13:
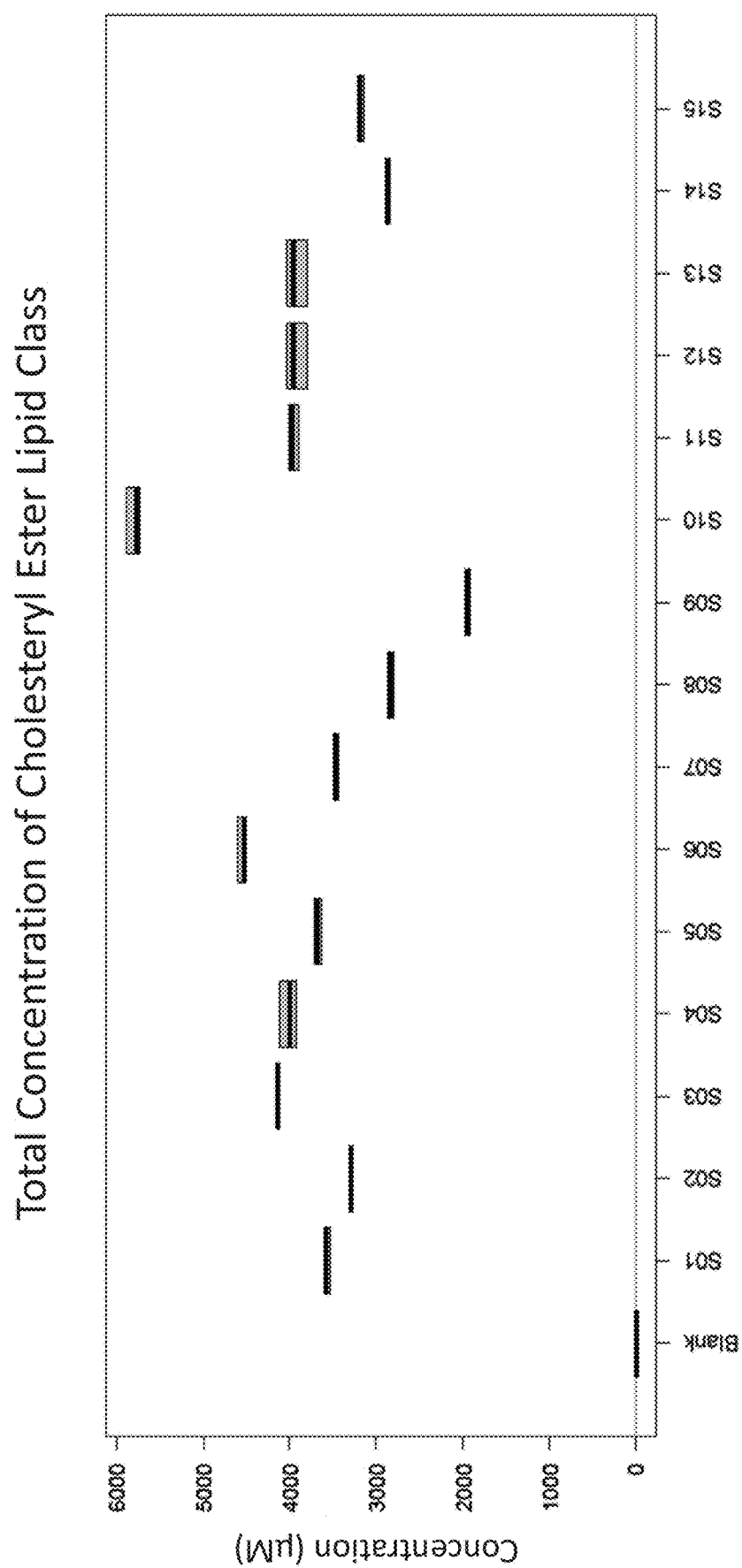
FIG. 13 shows box plots of the total concentration of the cholesteryl ester (CE) lipid class, calculated using the internal standard mixture, for 15 human serum samples run in triplicate according to one or more embodiments of the present disclosure.
Figure 14:
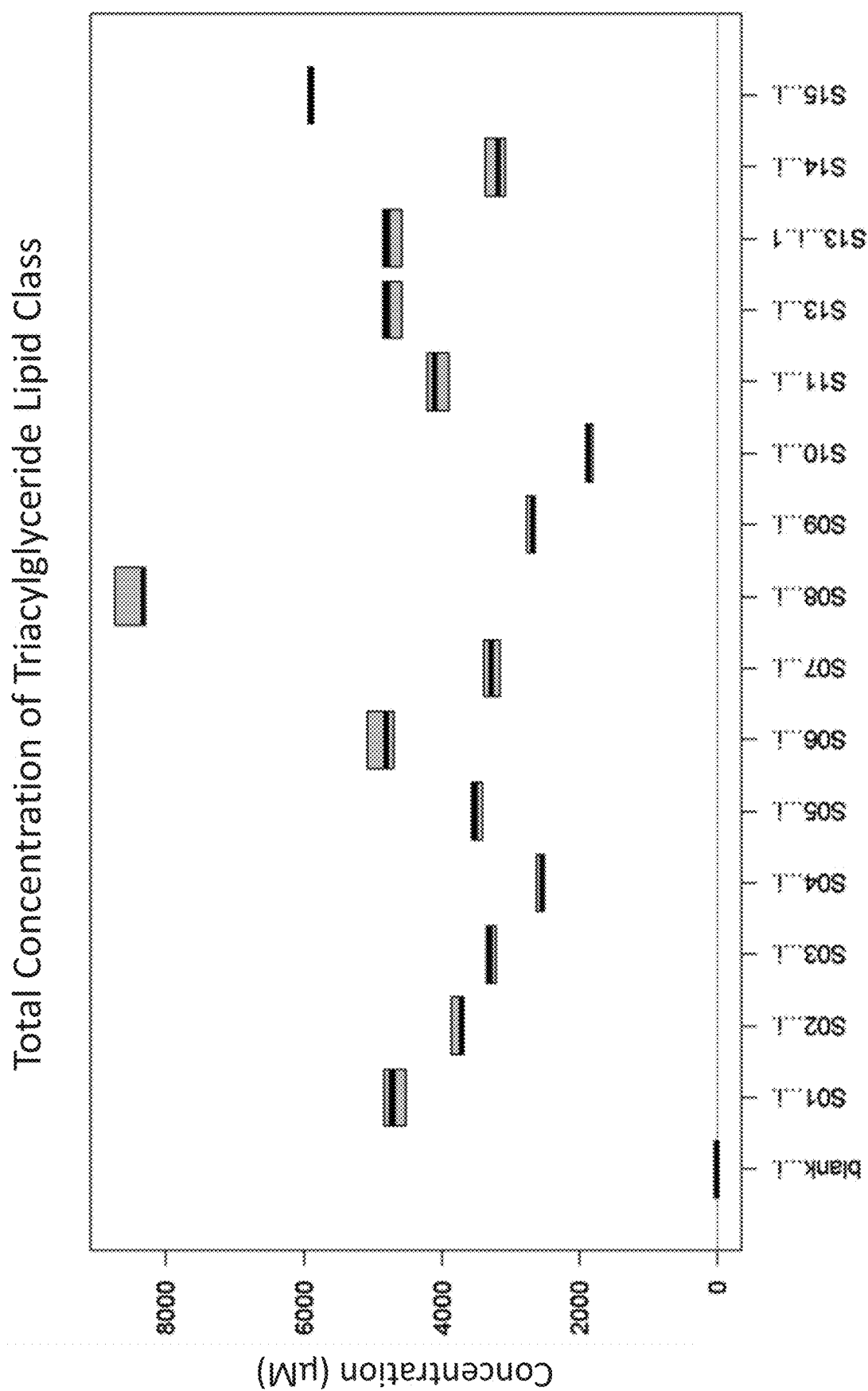
FIG. 14 shows box plots of the total concentration of the triacylglycerol (TAG) lipid class, calculated using the internal standard mixture, for 15 human serum samples run in triplicate according to one or more embodiments of the present disclosure.

The average concentration of the CE lipid class from all serum samples was 3676.72, and the average CV was 1.22%. These results are presented in box plot format in FIG. 13. The signal, which is the ratio of the concentration of CE lipid class in the serum samples to the blanks, was 1729.02. The average concentration of the TAG lipid class was 4105.8, and the average CV was 2.79%. These results are presented in box plot format in FIG. 14. The signal for the TAG lipid class was 1348.33.

In another example, the performance of the internal standard mixture compared to a traditional internal standard was evaluated in 25 human plasma samples. Using the methods described herein and the composition of internal standards described in Table 1, the fatty acid composition of three exemplary lipid classes (CE, PC, and PE) was calculated. These results were compared to calculations done using the traditional method of a single internal standard per lipid class and were also compared to quantitative values.

For quantitation using a single internal standard for each lipid class (traditional method), the dCE(16:0) internal standard was used for cholesteryl ester, the dPC(16:0/18:1) internal standard was used for phosphatidylcholine, and the dPE(18:0/18:1) internal standard was used for phosphatidylethanolamine. For single internal standard quantitation, fatty acids within CE, PC or PE lipid classes were assigned to the single CE, PC or PE internal standard, respectively.

For quantitation using an exemplary mixture of internal standards, the full complement of internal standards for each lipid class was used (Table 1). In all cases, the lipid molecular species to be quantified was assigned to an internal standard with the same number of double bonds in the fatty acid composition. For instance, the molecular species PC(16:0/22:5), PC(18:0/22:5) and PC(14:0/22:5) were all assigned to the internal standard dPC(16:0/22:5).

Figure 15A:
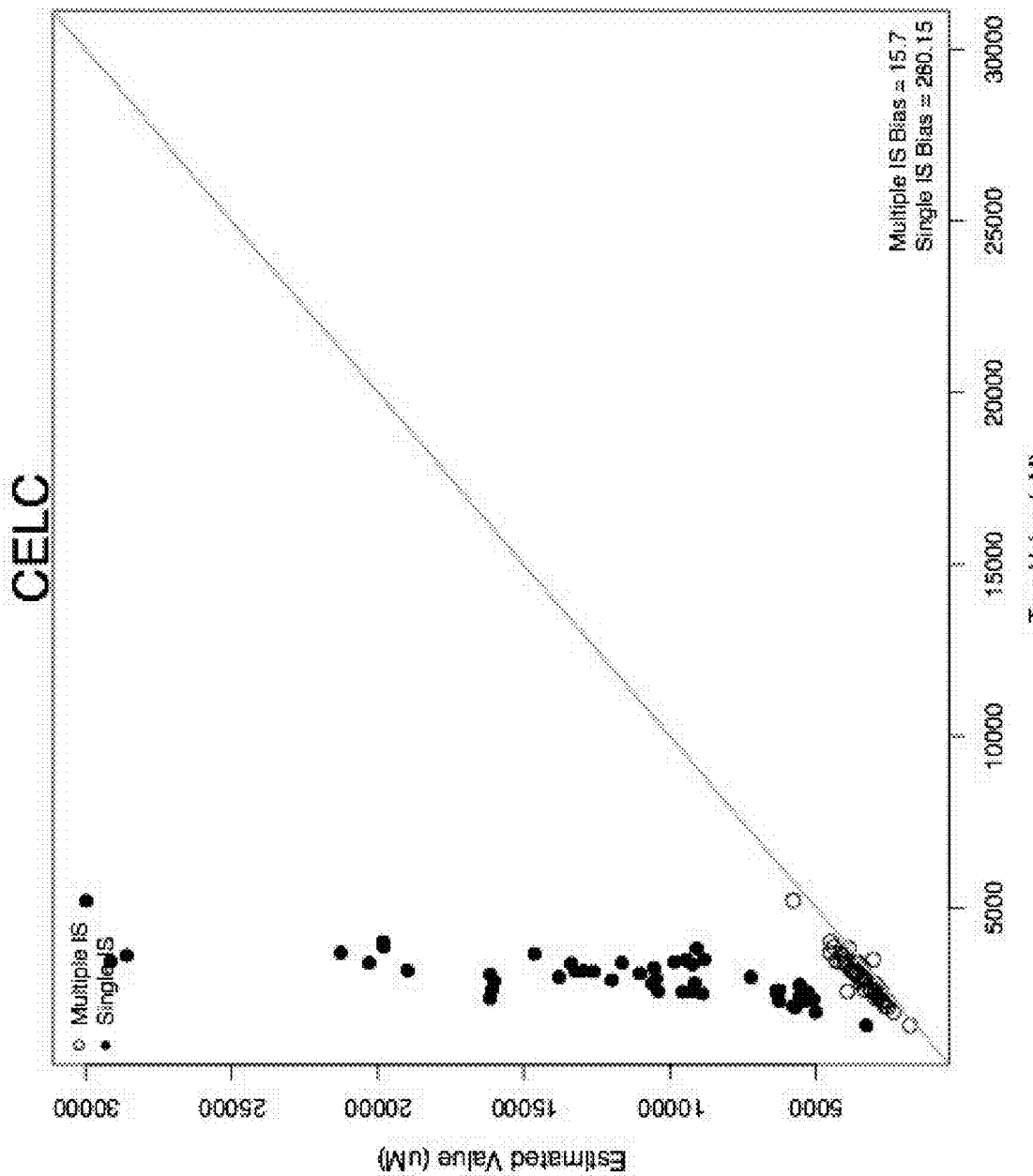
FIG. 15A is a plot showing the total concentration of cholesteryl ester (CE); lipid class calculated using a single internal standard and multiple internal standards according to one or more embodiments of the present disclosure.
Figure 15B:
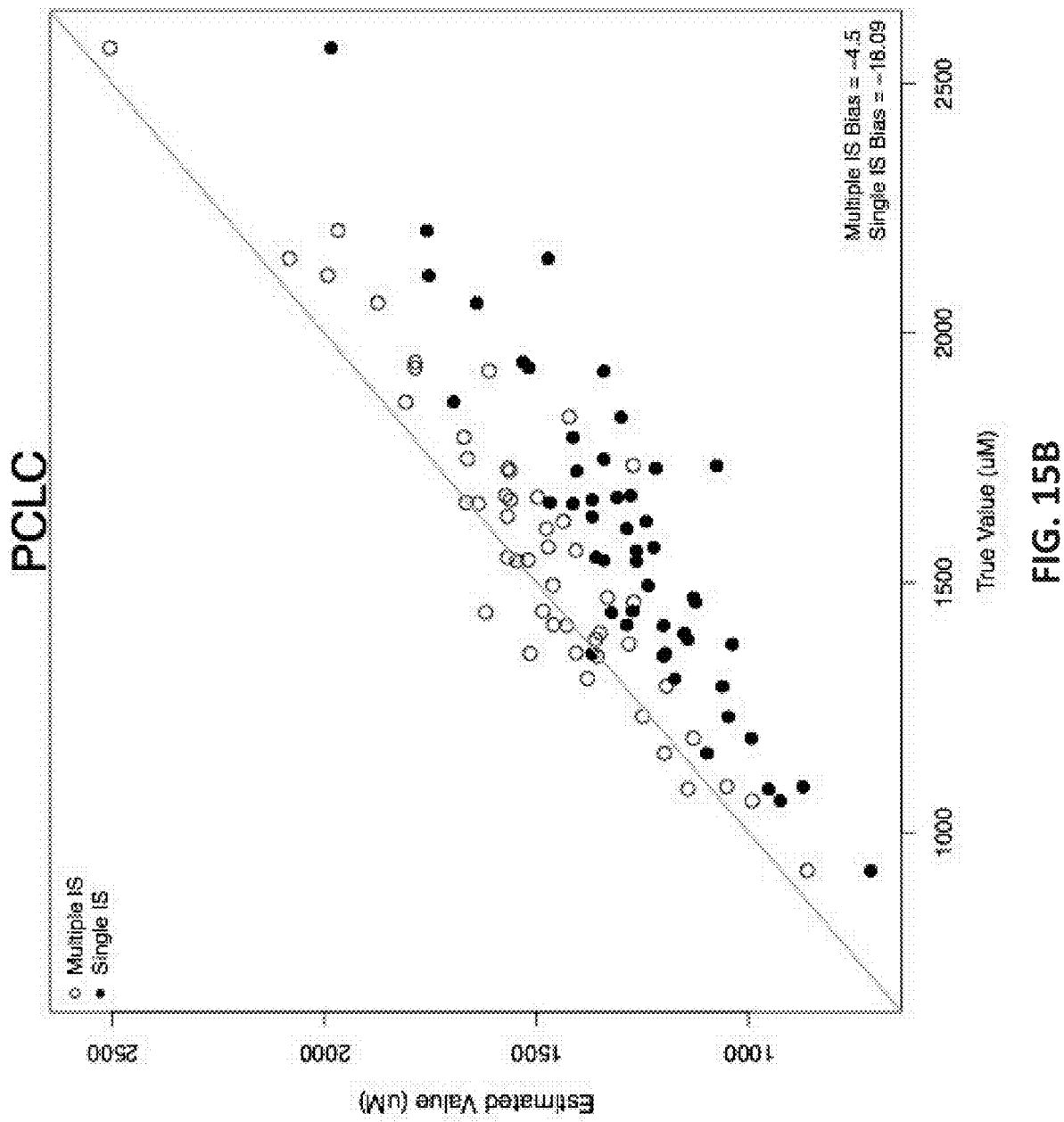
FIG. 15B is a plot showing the total concentration of phosphatidylcholine (PC) lipid class calculated using a single internal standard and multiple internal standards according to one or more embodiments of the present disclosure.
Figure 15C:
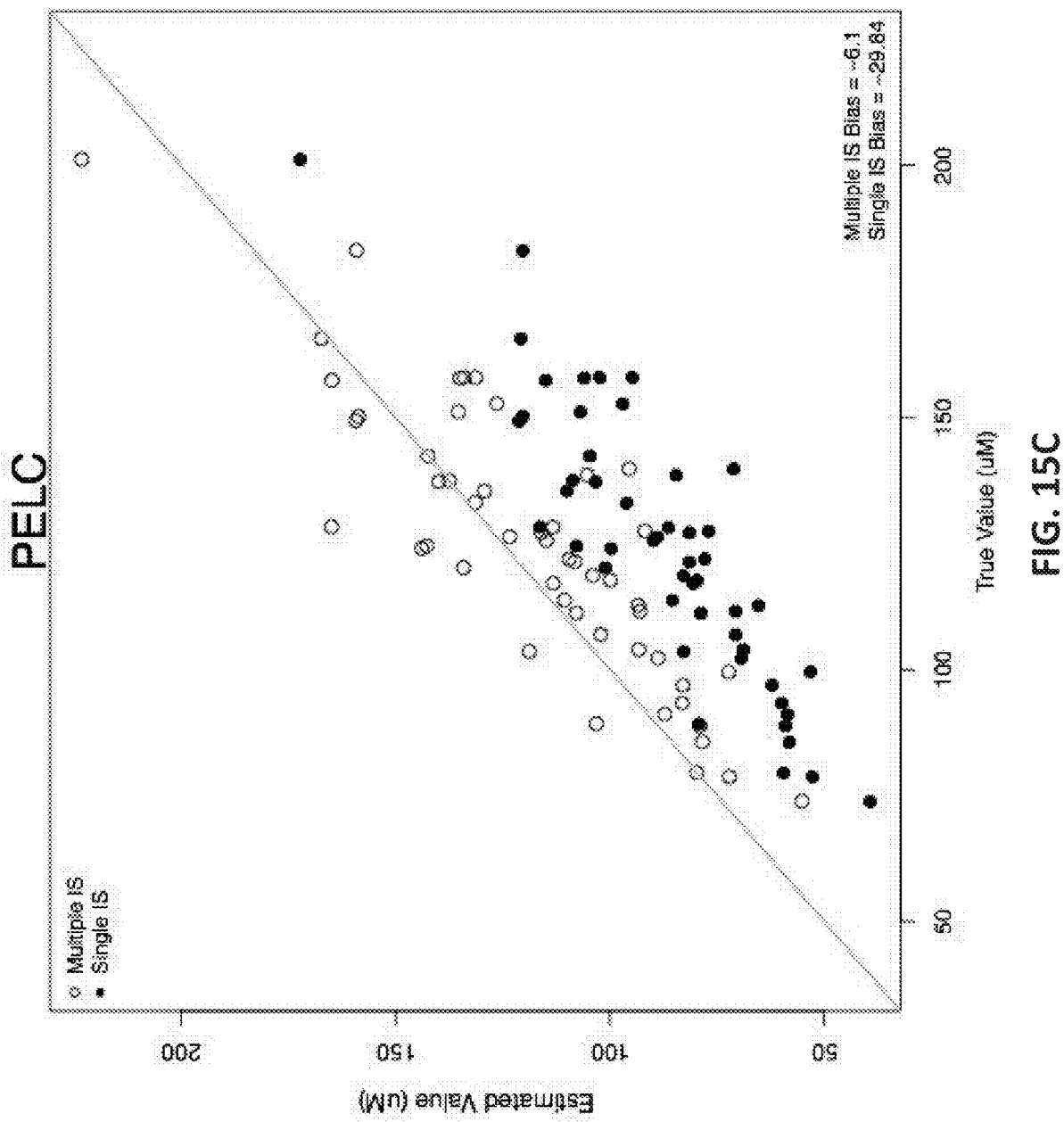
FIG. 15C is a plot showing the total concentration of phosphatidylethanolamine (PE) lipid class calculated using a single internal standard and multiple internal standards according to one or more embodiments of the present disclosure.

Total concentrations of cholesteryl ester (CELC), phosphatidylcholine (PCLC) and phosphatidylethanolamine (PELC) lipid classes were determined from the 25 human plasma samples with calculations using both a single internal standard and a mixture of internal standards (Multiple IS) per lipid class (FIG. 15). Results were compared to values obtained by quantitative GC-FID analysis (True-Mass, described elsewhere). Bias was calculated as:

((Calculated value−TrueMass value)/TrueMass value)*100

Bias was calculated for the single internal standard method and the multiple internal standard method. The results are presented in Table 10.

TABLE 10

| Bias for total concentration calculated for three exemplary lipid classes | | |
|---|---|---|
| | Single IS | Multiple IS |
| Cholesteryl Ester (CELC) | 280.2% | 15% |
| Phosphatidylcholine (PCLC) | −18.1% | −4.5% |
| Phosphatidylethanolamine (PELC) | −29.8% | −6.1% |

Figure 16:
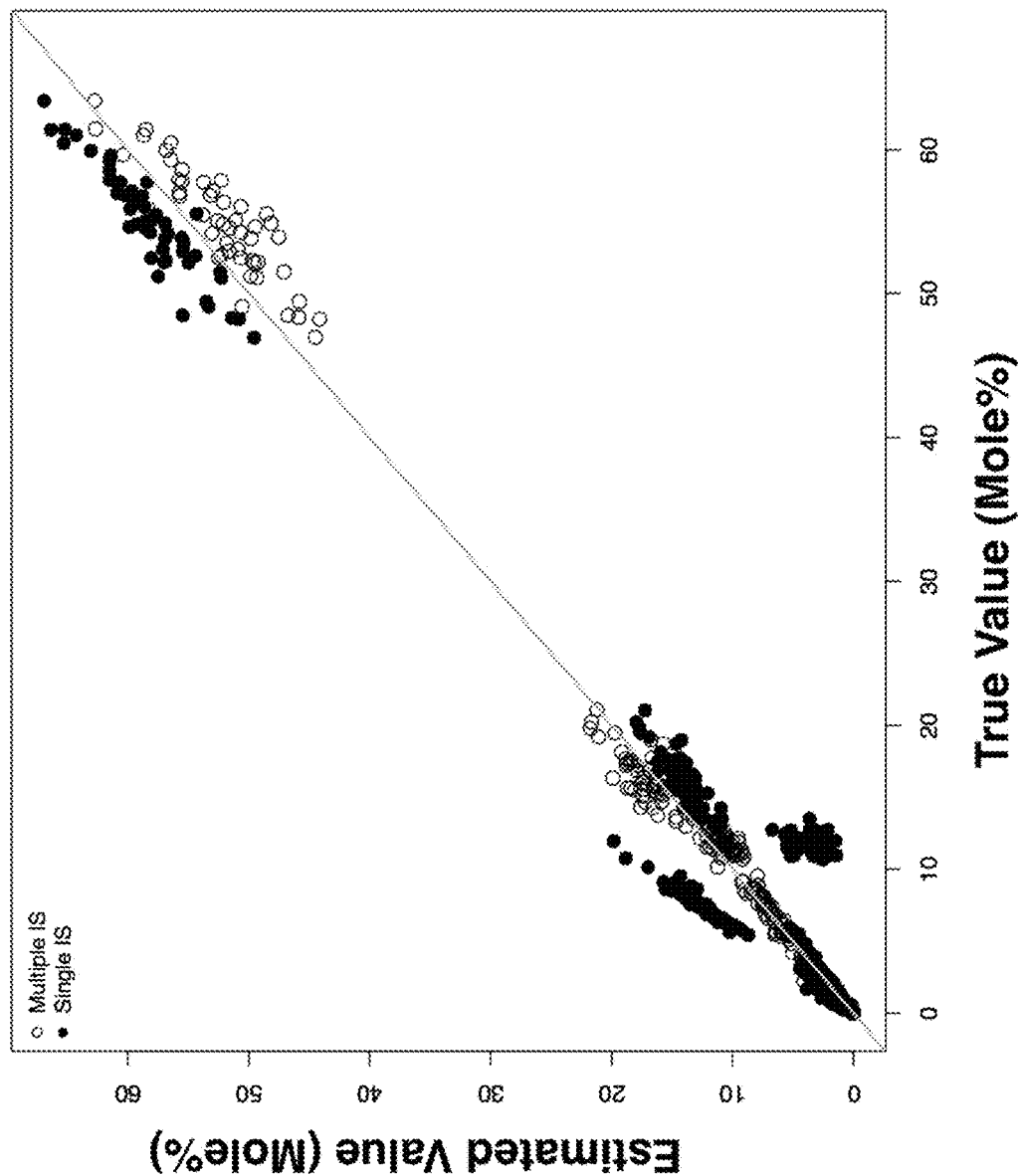
FIG. 16 is a plot showing the relative amount of the 22 fatty acids measured in the cholesteryl ester (CE) lipid class calculated using a single internal standard and multiple internal standards according to one or more embodiments of the present disclosure.
Figure 17A:
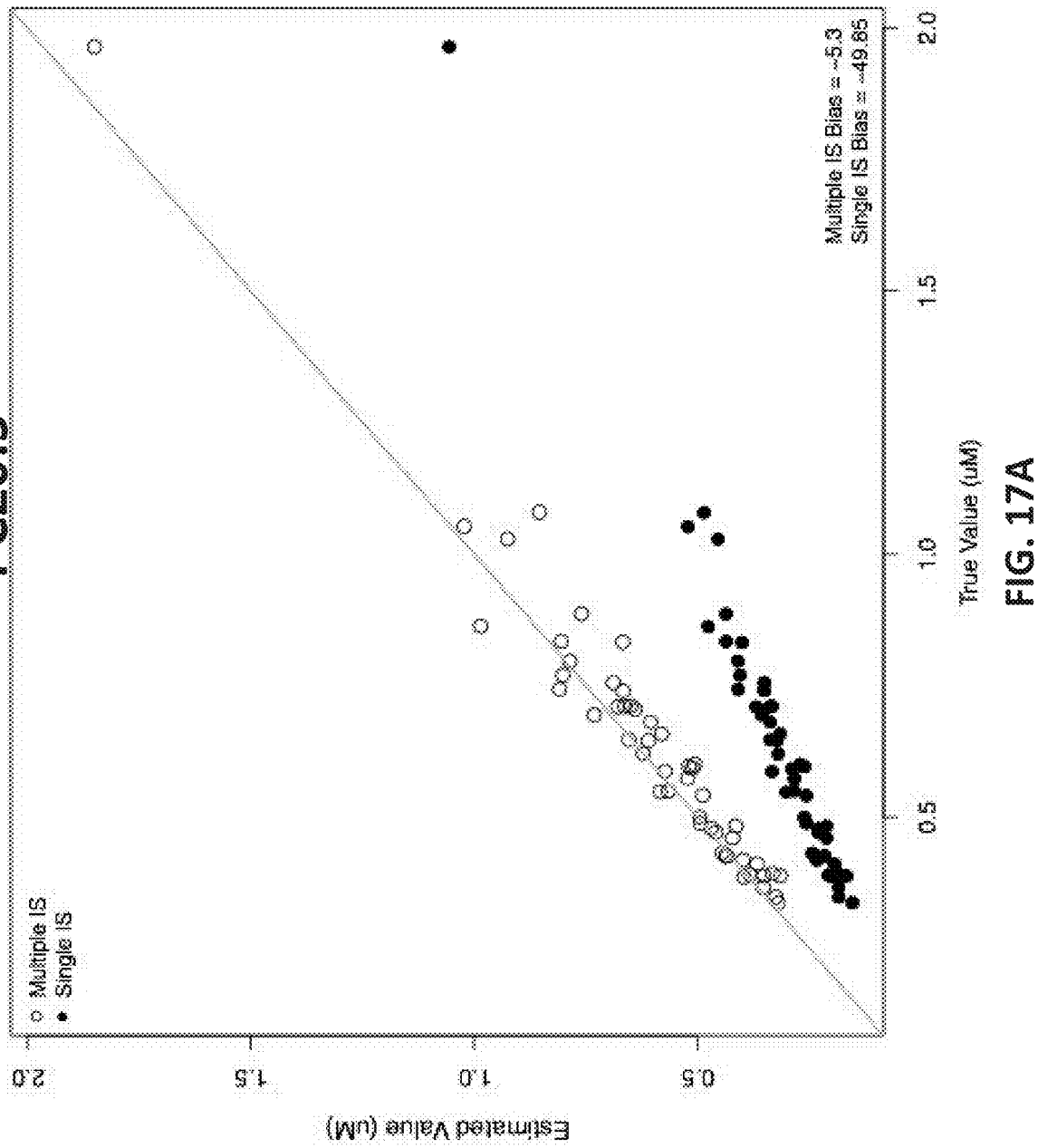
FIG. 17A shows the concentration of exemplary polyunsaturated fatty acid in the phosphatidylcholine (PC) lipid class PC20:5 calculated using a single internal standard and multiple internal standards according to one or more embodiments of the present disclosure.
Figure 17B:
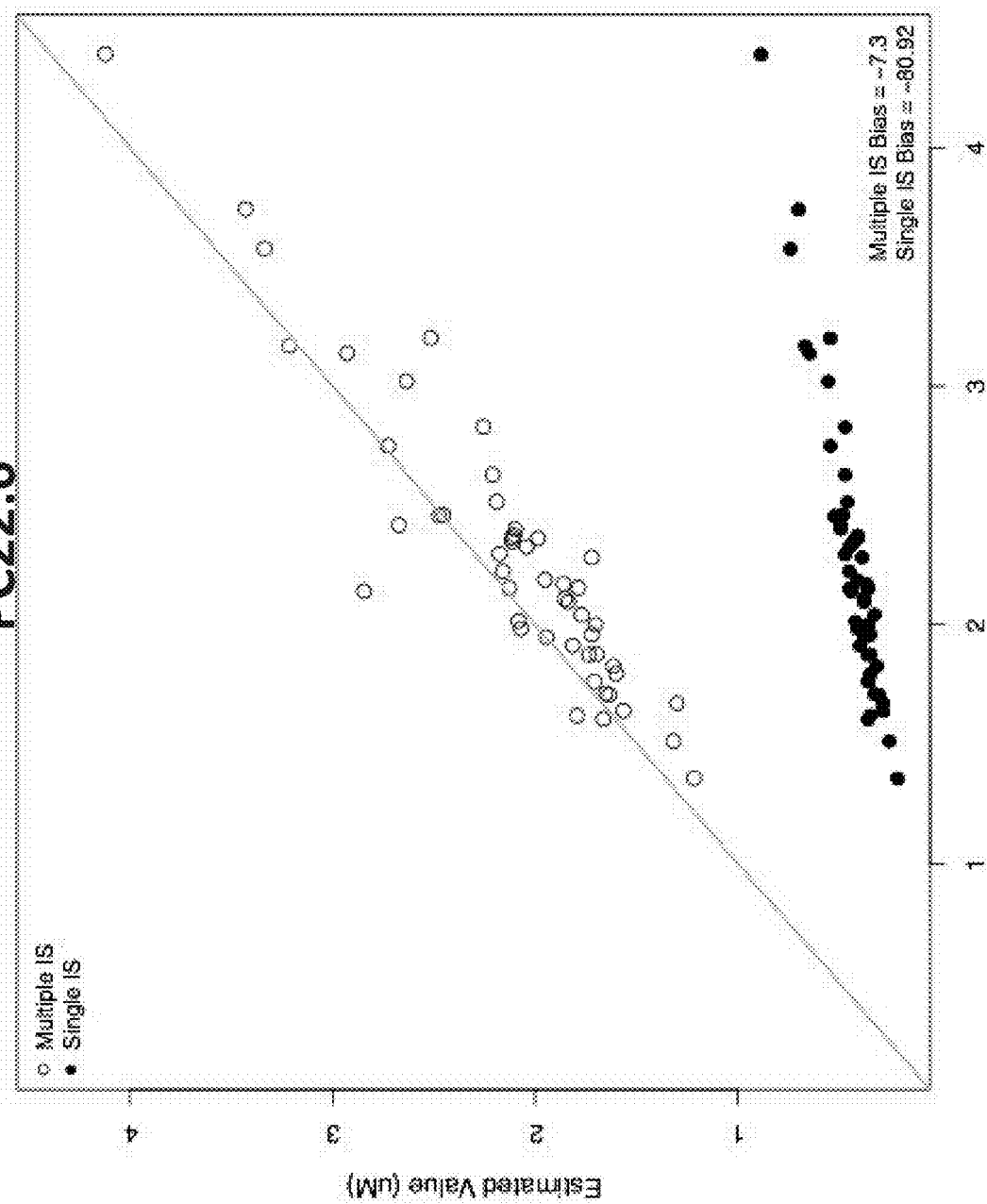
FIG. 17B shows the concentration of exemplary polyunsaturated fatty acid in the phosphatidylcholine (PC) lipid class PC22:6 calculated using a single internal standard and multiple internal standards according to one or more embodiments of the present disclosure.
Figure 17C:
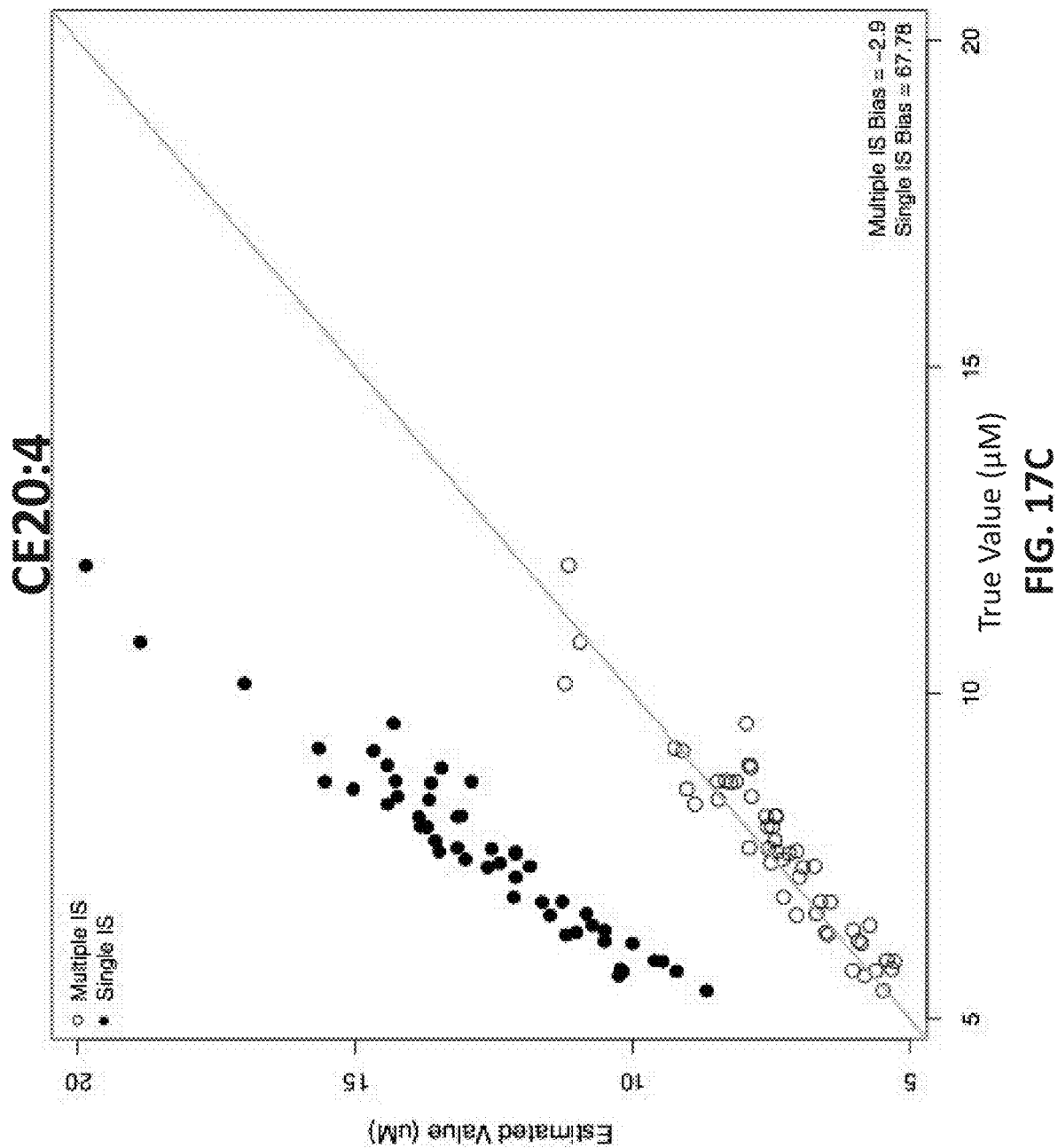
FIG. 17C shows the concentration of exemplary polyunsaturated fatty acid in the cholesteryl ester (CE) lipid class CE40:4 calculated using a single internal standard and multiple internal standards according to one or more embodiments of the present disclosure.
Figure 17D:
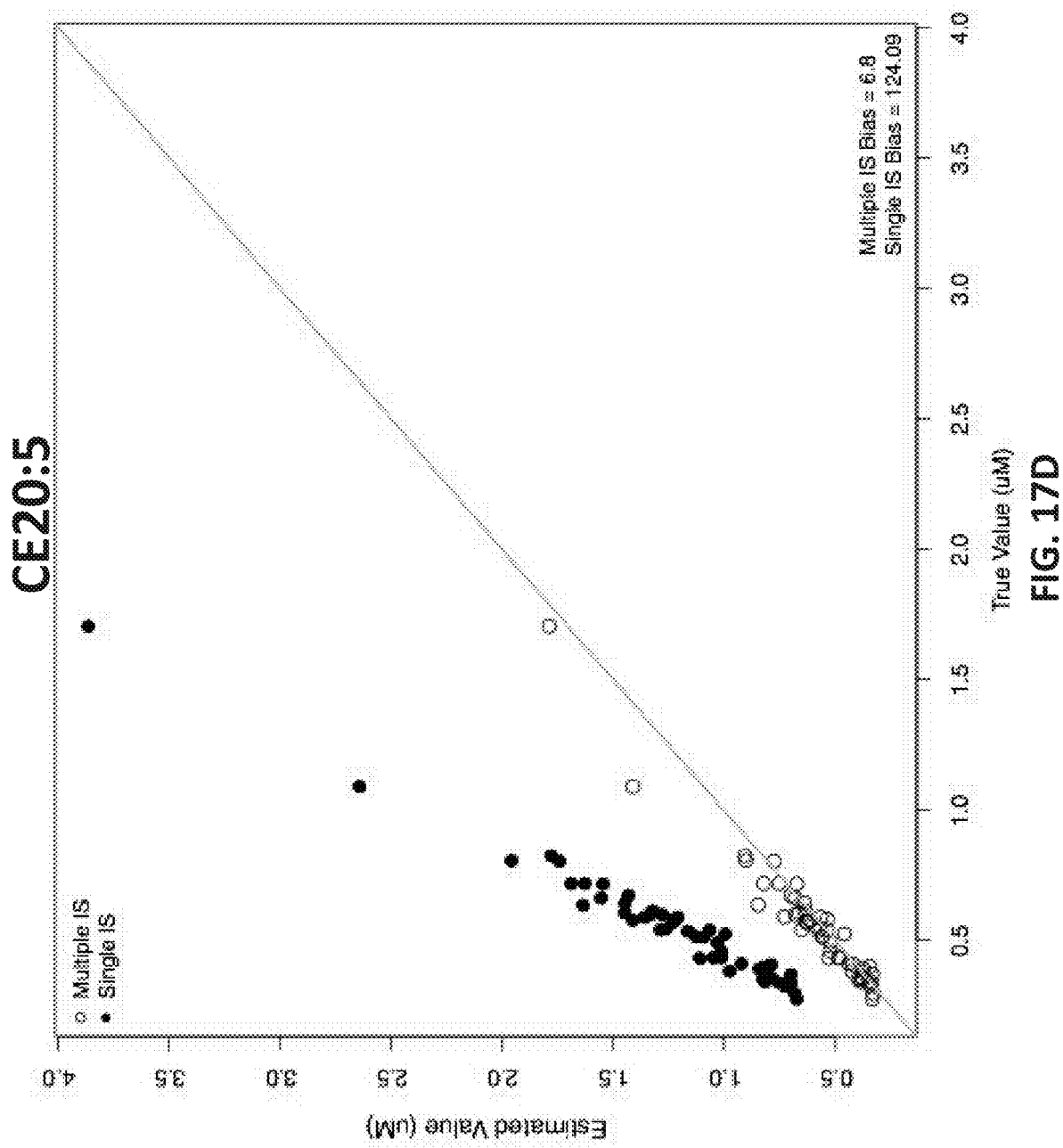
FIG. 17D shows the concentration of exemplary polyunsaturated fatty acid in the cholesteryl ester (CE) lipid class CE20:5 calculated using a single internal standard and multiple internal standards according to one or more embodiments of the present disclosure.

Next, the fatty acid composition of CE, PC, and PE lipid classes was determined. All values were expressed in Mole %, a form of data that provides the relative amount of a fatty acid present in each class relative to all fatty acids. As one example, a comparison of the fatty acid composition of cholesteryl ester (CE) for the single IS (dCE(16:0)) and multiple IS methods relative to quantitative (TrueMass) values is shown in FIG. 16. The y=x line indicates a value with a bias equal to zero. All 25 subjects are plotted for each of the 22 fatty acids measured in the CE lipid class. Although some fatty acids are measured effectively using a single internal standard, others show significant bias, however, the bias is lower when the multiple IS were used.

In particular, the polyunsaturated fatty acids appeared to be substantially biased using the single IS method. Specific examples of the bias against polyunsaturated fatty acids from the CE and PC lipid classes are shown below. The bias was calculated as described above and is presented in Table 11. The true (quantitative) value (µM) and the estimated value (calculated using an internal standard) (µM) for the exemplary fatty acids of the PC and CE lipid classes were plotted for each of the 25 plasma samples. The results are shown in FIG. 17.

TABLE 11

| Bias for relative amount of exemplary fatty acids in the given lipid class | | |
|---|---|---|
| | Single IS | Multiple IS |
| PC20:5 | −49.8% | −5.3% |
| PC22:6 | −80.9% | −7.3% |
| CE20:4 | 67.7% | −2.9% |
| CE20:5 | 124.1% | 6.8% |

Here we show that using a single internal standard per class can cause quantitative and compositional biases in the results, because the single internal standard was not able to accurately quantify all molecular species within a class. Using the methods described herein, the quantitative and compositional bias in lipidomics assays was significantly and substantially reduced.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed:

1. An isotopically-labeled internal standard composition comprising eight lipid molecular species, wherein each of the eight lipid molecular species in the composition consists essentially of:
   a cholesteryl ester lipid backbone (CE) having one or more isotopic labels and
   a fatty acid residue present at a single position on the lipid backbone,
   wherein the fatty acid residue is selected from the group consisting of 16:0, 16:1, 18:1, 18:2, 20:3, 20:4, 20:5, and 22:6.

2. The composition of claim 1, wherein the one or more isotopic labels comprise $^2H$ or $^{13}C$.

3. The composition of claim 1, wherein the lipid molecular species are present in the composition as follows:
   5% CE16:0,
   5% CE16:1,
   20% CE18:1,
   50% CE18:2,
   5% CE20:3,
   5% CE20:4,
   5% CE20:5, and
   5% CE22:6.

4. A kit comprising the composition of claim 1 and instructions for using the composition as an internal standard.

* * * * *